(12) United States Patent
Ansell et al.

(10) Patent No.: US 9,738,593 B2
(45) Date of Patent: Aug. 22, 2017

(54) LIPIDS AND LIPID NANOPARTICLE FORMULATIONS FOR DELIVERY OF NUCLEIC ACIDS

(71) Applicant: Acuitas Therapeutics Inc., Vancouver (CA)

(72) Inventors: Steven M. Ansell, Vancouver (CA); Xinyao Du, Richmond (CA)

(73) Assignee: Acuitas Therapeutics Inc., Vancouver, B.C. (CA)

( * ) Notice: Subject to any disclaimer, the term of this patent is extended or adjusted under 35 U.S.C. 154(b) by 0 days.

(21) Appl. No.: 14/732,218

(22) Filed: Jun. 5, 2015

(65) Prior Publication Data

US 2015/0376115 A1     Dec. 31, 2015

Related U.S. Application Data

(60) Provisional application No. 62/016,839, filed on Jun. 25, 2014.

(51) Int. Cl.
*C07C 219/06* (2006.01)
*A61K 47/18* (2017.01)
(Continued)

(52) U.S. Cl.
CPC ......... *C07C 219/06* (2013.01); *A61K 9/1272* (2013.01); *A61K 47/18* (2013.01);
(Continued)

(58) Field of Classification Search
None
See application file for complete search history.

(56) References Cited

U.S. PATENT DOCUMENTS 2,856,420 A  * 10/1958 Crawford, Jr. .......... C08L 75/04
                                                            524/239
3,729,564 A     4/1973 Chang et al.
(Continued)

FOREIGN PATENT DOCUMENTS

GB       1 277 947        7/1969
JP       4681425 B2       2/2011
(Continued)

OTHER PUBLICATIONS

Database Caplus Chemical Abstracts Service, Columbus, Ohio, US; Database Accession No. 1994:507994, Abstract of JP 05331118, Kao Corp, Japan, Tomifuji et al., Dec. 14, 1993.*
(Continued)

*Primary Examiner* — Karl J Puttlitz
(74) *Attorney, Agent, or Firm* — Seed IP Law Group LLP

(57) ABSTRACT

Compounds are provided having the following structure:

(I)

or a pharmaceutically acceptable salt, tautomer or stereoisomer thereof, wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^7$, $R^8$, $R^9$, $L^1$, $L^2$, a, b, c, d and e are as defined herein. Use of the compounds as a component of lipid nanoparticle formulations for delivery of a therapeutic
(Continued)

agent, compositions comprising the compounds and methods for their use and preparation are also provided.

47 Claims, 4 Drawing Sheets

(51) Int. Cl.
 A61K 47/22  (2006.01)
 C07C 219/08  (2006.01)
 C07C 229/16  (2006.01)
 C07D 295/13  (2006.01)
 C08G 65/333  (2006.01)
 A61K 9/127  (2006.01)
 C07C 219/10  (2006.01)

(52) U.S. Cl.
 CPC ............ *A61K 47/22* (2013.01); *C07C 219/08* (2013.01); *C07C 219/10* (2013.01); *C07C 229/16* (2013.01); *C07D 295/13* (2013.01); *C08G 65/33306* (2013.01)

(56) References Cited

U.S. PATENT DOCUMENTS

| | | | |
|---|---|---|---|
| 3,931,430 A * | 1/1976 | Tada | B41M 5/128 427/146 |
| 4,121,898 A | 10/1978 | Kirschnek et al. | |
| 5,705,385 A | 1/1998 | Bally et al. | |
| 5,756,785 A | 5/1998 | O'Lenick, Jr. | |
| 5,919,743 A | 7/1999 | O'Lenick, Jr. | |
| 5,965,542 A | 10/1999 | Wasan et al. | |
| 5,976,567 A | 11/1999 | Wheeler et al. | |
| 5,981,501 A | 11/1999 | Wheeler et al. | |
| 6,013,813 A | 1/2000 | O'Lenick, Jr. | |
| 6,107,286 A | 8/2000 | Byk et al. | |
| 6,300,321 B1 | 10/2001 | Scherman et al. | |
| 6,410,328 B1 | 6/2002 | Maclachlan et al. | |
| 6,534,484 B1 | 3/2003 | Wheeler et al. | |
| 6,586,410 B1 | 7/2003 | Wheeler et al. | |
| 6,620,794 B1 | 9/2003 | O'Lenick, Jr. et al. | |
| 6,815,432 B2 | 11/2004 | Wheeler et al. | |
| 6,858,224 B2 | 2/2005 | Wheeler et al. | |
| 6,986,902 B1 | 1/2006 | Chen et al. | |
| 7,470,781 B2 | 12/2008 | Crouzet et al. | |
| 7,745,651 B2 | 6/2010 | Heyes et al. | |
| 7,799,565 B2 | 9/2010 | MacLachlan et al. | |
| 7,803,397 B2 | 9/2010 | Heyes et al. | |
| 7,811,602 B2 | 10/2010 | Cullis et al. | |
| 7,901,708 B2 | 3/2011 | MacLachlan et al. | |
| 7,982,027 B2 | 7/2011 | MacLachlan et al. | |
| 8,034,376 B2 | 10/2011 | Manoharan et al. | |
| 8,158,601 B2 | 4/2012 | Chen et al. | |
| 8,283,333 B2 | 10/2012 | Yaworski et al. | |
| 8,329,070 B2 | 12/2012 | MacLachlan et al. | |
| 8,466,122 B2 | 6/2013 | Heyes et al. | |
| 8,569,256 B2 | 10/2013 | Heyes et al. | |
| 8,575,123 B2 | 11/2013 | Manoharan et al. | |
| 8,642,076 B2 | 2/2014 | Manoharan et al. | |
| 8,691,750 B2 | 4/2014 | Constien et al. | |
| 8,722,082 B2 | 5/2014 | Manoharan et al. | |
| 8,802,644 B2 | 8/2014 | Chen et al. | |
| 8,822,668 B2 | 9/2014 | Yaworski et al. | |
| 2004/0142025 A1 | 7/2004 | MacLachlan et al. | |
| 2005/0064595 A1 | 3/2005 | MacLachlan et al. | |
| 2007/0042031 A1 | 2/2007 | MacLachlan et al. | |
| 2009/0247608 A1 | 10/2009 | Manoharan et al. | |
| 2010/0285112 A1 | 11/2010 | Novobrantseva et al. | |
| 2011/0045473 A1 | 2/2011 | De Fougerolles et al. | |
| 2011/0091525 A1 | 4/2011 | Heyes et al. | |
| 2011/0097720 A1 | 4/2011 | Ciufolini et al. | |
| 2011/0262527 A1 | 10/2011 | Heyes et al. | |
| 2011/0300205 A1 | 12/2011 | Geall et al. | |
| 2011/0311582 A1 | 12/2011 | Manoharan et al. | |
| 2011/0311583 A1 | 12/2011 | Manoharan et al. | |
| 2012/0027796 A1 | 2/2012 | Manoharan et al. | |
| 2012/0027803 A1 | 2/2012 | Manoharan et al. | |
| 2012/0046478 A1 | 2/2012 | Manoharan et al. | |
| 2012/0058144 A1 | 3/2012 | Manoharan et al. | |
| 2012/0058188 A1 | 3/2012 | Maclachlan et al. | |
| 2012/0095075 A1 | 4/2012 | Manoharan et al. | |
| 2012/0101148 A1 | 4/2012 | Aking et al. | |
| 2012/0128760 A1 | 5/2012 | Manoharan et al. | |
| 2012/0172411 A1 | 7/2012 | Heyes et al. | |
| 2012/0183602 A1 | 7/2012 | Chen et al. | |
| 2012/0225434 A1 | 9/2012 | Ciufolini et al. | |
| 2012/0244207 A1 | 9/2012 | Fitzgerald et al. | |
| 2012/0251618 A1 | 10/2012 | Schrum et al. | |
| 2012/0295832 A1 | 11/2012 | Constien et al. | |
| 2013/0017223 A1 | 1/2013 | Hope et al. | |
| 2013/0022649 A1 | 1/2013 | Yaworski et al. | |
| 2013/0108685 A1 | 5/2013 | Kuboyama et al. | |
| 2013/0122104 A1 | 5/2013 | Yaworski et al. | |
| 2013/0123338 A1 | 5/2013 | Heyes et al. | |
| 2013/0129811 A1 | 5/2013 | Kuboyama et al. | |
| 2013/0261172 A1 | 10/2013 | Kariko et al. | |
| 2013/0280305 A1 | 10/2013 | Kuboyama et al. | |
| 2013/0323269 A1 | 12/2013 | Manoharan et al. | |
| 2013/0338210 A1 | 12/2013 | Manoharan et al. | |
| 2014/0044772 A1 | 2/2014 | MacLachlan et al. | |
| 2014/0121393 A1 | 5/2014 | Manoharan et al. | |
| 2014/0134260 A1 | 5/2014 | Heyes et al. | |
| 2014/0179761 A1 | 6/2014 | Manoharan et al. | |
| 2014/0256785 A1 | 9/2014 | Manoharan et al. | |
| 2014/0294937 A1 | 10/2014 | MacLachlan et al. | |
| 2014/0295449 A1 | 10/2014 | Ciufolini et al. | |
| 2014/0323548 A1 | 10/2014 | Budzik et al. | |
| 2016/0376224 A1 | 12/2016 | Du et al. | |

FOREIGN PATENT DOCUMENTS

| | | |
|---|---|---|
| WO | 97/30024 A2 | 8/1997 |
| WO | 98/16599 A1 | 4/1998 |
| WO | 99/33493 A1 | 7/1999 |
| WO | 01/07548 A1 | 2/2001 |
| WO | 2006/138380 A2 | 12/2006 |
| WO | 2009/132131 A1 | 10/2009 |
| WO | 2010/048536 A2 | 4/2010 |
| WO | 2010/054405 A1 | 5/2010 |
| WO | 2010/054406 A1 | 5/2010 |
| WO | 2011/075656 A1 | 6/2011 |
| WO | 2011/141703 A1 | 11/2011 |
| WO | 2011/141705 A1 | 11/2011 |
| WO | 2012/000104 A1 | 1/2012 |
| WO | 2013/014073 A1 | 1/2013 |
| WO | 2013/016058 A1 | 1/2013 |
| WO | 2013/059496 A1 | 4/2013 |
| WO | 2013/086373 * | 6/2013 |
| WO | 2013/086373 A1 | 6/2013 |
| WO | 2014/008334 A1 | 1/2014 |
| WO | 2014/153163 A1 | 9/2014 |
| WO | 2015/074085 A1 | 5/2015 |

OTHER PUBLICATIONS

Database Caplus Chemical Abstracts Service, Columbus, Ohio, US; Database Accession No. 1959:6545, Abstract of U.S. 2856420, Minnesota Mining and Manufacturing Co., Crawford, Oct. 14, 1958.*
Torrecilla et al., "Lipid Nanoparticles as Carriers for RNAi against Viral Infections: Current Status and Future Perspectives," *BioMed Research International 2014:*Article ID 161794, 17 pages.
Alabi et al., "Multiparametric approach for the evaluation of lipid nanoparticles for siRNA delivery,"*PNAS* 110(32):12881-12886, Aug. 6, 2013.
Alexidis et al., "Novel 1,4 Substituted Piperidine Derivatives. Synthesis and Correlation of Antioxidant Activity with Structure and Lipophilicity," *J. Pharm. Pharmacol.* 47:131-137, 1995.
Cattanach et al., "Studies in the Indole Series. Part IV. Tetrahydro-1H-pyrido[4,3-b]-indoles as Serotonin Antagonists," *J. Chem. Soc. Perkin* 1. 10:1235-1243, 1968.

(56) References Cited

OTHER PUBLICATIONS

Cook et al., "Synthesis and Characterization of cis-Dioxomolybdenum(IV) Complexes with Sterically Bulky Tripodal Tetradentate Ligands," *Inorganica Chimica Acta* 144:81-87, 1988.
Frisch et al., "A New Triantennary Galactose-Targeted PEGylated Gene Carrier, Characterization of Its Complex with DNA, and Transfection of Hepatoma Cells," *Bioconjugate Chem.* 15:754-764, 2004.
Hafez et al., "On the mechanism whereby cationic lipids promote intracellular delivery of polynucleic acids," *Gene Therapy* 8:1188-1196, 2001.
Jayaraman et al., "Maximizing the Potency of siRNA Lipid Nanoparticles for Hepatic Gene Silencing In Vivo," *Angew. Chem. Int. Ed.* 51:8529-8533, 2012.
MacLachlan, "Lipid Nanoparticle-Mediated Delivery of Messenger RNA," 1st International mRNA Health Conference, Oct. 24, 2013, Tubingen, Germany, 32 pages.
Maier et al., "Biodegradable Lipids Enabling Rapidly Eliminated Lipid Nanoparticles for Systemic Delivery of RNAi Therapeutics," *Molecular Therapy* 21(8):1570-1578, Aug. 2013.
Novobrantseva et al., "Systemic RNAi-mediated Gene Silencing in Nonhuman Primate and Rodent Myeloid Cells,"*Molecular Therapy—Nucleic Acids* 1(e4), 2012, 13 pages.
Schar et al., "Long Chain Linear Fatty Alcohols from Ziegler—Synthesis, their Mixtures, Derivatives and Use," IP.com Prior Art Database Technical Disclosure, Jan. 17, 2011, 39 pages.
Semple et al., "Interactions of liposomes and lipid-based carrier systems with blood proteins: Relation to clearance behaviour in vivo," *Advanced Drug Delivery Reviews* 32:3-17, 1998.
Semple et al., "Rational design of cationic lipids for siRNA delivery," *Nature Biotechnology* 28(2):172-176, Feb. 2010, 26 pages.
Tekmira Pharmaceuticals Corp, Form 20-F, Edgar Online, filed Mar. 27, 2013, 298 pages.
Tekmira, "Tekmira and Alnylam Restructure Relationship and Settle All Litigation," Tekmira Pharmaceuticals Corporation, Nov. 12, 2012, 3 pages.
Yoshimura et al., "Solution Properties of Tadpole-type Cationic Amphiphilic Dendrimers Consisting of an Alkyl Chain, a Quaternary Ammonium, and a Poly(amidoamine) Dendron," *J. Oleo Sci.* 62(4):213-221, 2013.

\* cited by examiner

LIPIDS AND LIPID NANOPARTICLE FORMULATIONS FOR DELIVERY OF NUCLEIC ACIDS

BACKGROUND

Technical Field

The present invention generally relates to novel cationic lipids that can be used in combination with other lipid components, such as neutral lipids, cholesterol and polymer conjugated lipids, to form lipid nanoparticles with oligonucleotides, to facilitate the intracellular delivery of therapeutic nucleic acids (e.g. oligonucleotides, messenger RNA) both in vitro and in vivo.

Description of the Related Art

There are many challenges associated with the delivery of nucleic acids to effect a desired response in a biological system. Nucleic acid based therapeutics have enormous potential but there remains a need for more effective delivery of nucleic acids to appropriate sites within a cell or organism in order to realize this potential. Therapeutic nucleic acids include, e.g., messenger RNA (mRNA), antisense oligonucleotides, ribozymes, DNAzymes, plasmids, immune stimulating nucleic acids, antagomir, antimir, mimic, supermir, and aptamers. Some nucleic acids, such as mRNA or plasmids, can be used to effect expression of specific cellular products as would be useful in the treatment of, for example, diseases related to a deficiency of a protein or enzyme. The therapeutic applications of translatable nucleotide delivery are extremely broad as constructs can be synthesized to produce any chosen protein sequence, whether or not indigenous to the system. The expression products of the nucleic acid can augment existing levels of protein, replace missing or non-functional versions of a protein, or introduce new protein and associated functionality in a cell or organism.

Some nucleic acids, such as miRNA inhibitors, can be used to effect expression of specific cellular products that are regulated by miRNA as would be useful in the treatment of, for example, diseases related to deficiency of protein or enzyme. The therapeutic applications of miRNA inhibition are extremely broad as constructs can be synthesized to inhibit one or more miRNA that would in turn regulate the expression of mRNA products. The inhibition of endogenous miRNA can augment its downstream target endogenous protein expression and restore proper function in a cell or organism as a means to treat disease associated to a specific miRNA or a group of miRNA.

Other nucleic acids can down-regulate intracellular levels of specific mRNA and, as a result, down-regulate the synthesis of the corresponding proteins through processes such as RNA interference (RNAi) or complementary binding of antisense RNA. The therapeutic applications of antisense oligonucleotide and RNAi are also extremely broad, since oligonucleotide constructs can be synthesized with any nucleotide sequence directed against a target mRNA. Targets may include mRNAs from normal cells, mRNAs associated with disease-states, such as cancer, and mRNAs of infectious agents, such as viruses. To date, antisense oligonucleotide constructs have shown the ability to specifically down-regulate target proteins through degradation of the cognate mRNA in both in vitro and in vivo models. In addition, antisense oligonucleotide constructs are currently being evaluated in clinical studies.

However, two problems currently face using oligonucleotides in therapeutic contexts. First, free RNAs are susceptible to nuclease digestion in plasma. Second, free RNAs have limited ability to gain access to the intracellular compartment where the relevant translation machinery resides. Lipid nanoparticles formed from cationic lipids with other lipid components, such as neutral lipids, cholesterol, PEG, PEGylated lipids, and oligonucleotides have been used to block degradation of the RNAs in plasma and facilitate the cellular uptake of the oligonucleotides.

There remains a need for improved cationic lipids and lipid nanoparticles for the delivery of oligonucleotides. Preferably, these lipid nanoparticles would provide optimal drug:lipid ratios, protect the nucleic acid from degradation and clearance in serum, be suitable for systemic delivery, and provide intracellular delivery of the nucleic acid. In addition, these lipid-nucleic acid particles should be well-tolerated and provide an adequate therapeutic index, such that patient treatment at an effective dose of the nucleic acid is not associated with unacceptable toxicity and/or risk to the patient. The present invention provides these and related advantages.

BRIEF SUMMARY

In brief, the present invention provides lipid compounds, including stereoisomers, pharmaceutically acceptable salts or tautomers thereof, which can be used alone or in combination with other lipid components such as neutral lipids, charged lipids, steroids (including for example, all sterols) and/or their analogs, and/or polymer conjugated lipids to form lipid nanoparticles for the delivery of therapeutic agents. In some instances, the lipid nanoparticles are used to deliver nucleic acids such as antisense and/or messenger RNA. Methods for use of such lipid nanoparticles for treatment of various diseases or conditions, such as those caused by infectious entities and/or insufficiency of a protein, are also provided.

In one embodiment, compounds having the following Formula (I) are provided:

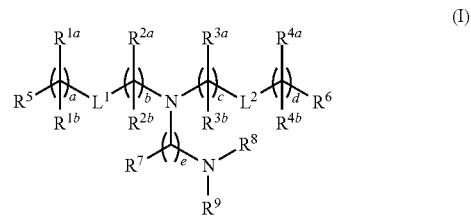

(I)

or a pharmaceutically acceptable salt, tautomer or stereoisomer thereof, wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^7$, $R^8$, $R^9$, $L^1$, $L^2$, a, b, c, d and e are as defined herein.

Pharmaceutical compositions comprising one or more of the foregoing compounds of Formula (I) and a therapeutic agent are also provided. In some embodiments, the pharmaceutical compositions further comprise one or more components selected from neutral lipids, charged lipids, steroids and polymer conjugated lipids. Such compositions are useful for formation of lipid nanoparticles for the delivery of the therapeutic agent.

In other embodiments, the present invention provides a method for administering a therapeutic agent to a patient in need thereof, the method comprising preparing a composition of lipid nanoparticles comprising the compound of Formula (I) and a therapeutic agent and delivering the composition to the patient.

In still more embodiments, the invention is directed to a pegylated lipid having the following structure (II):

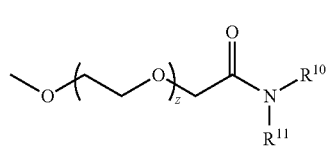

(II)

or a pharmaceutically acceptable salt, tautomer or stereoisomer thereof, wherein $R^{10}$, $R^{11}$ and z are as defined herein.

These and other aspects of the invention will be apparent upon reference to the following detailed description.

BRIEF DESCRIPTION OF THE SEVERAL VIEWS OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
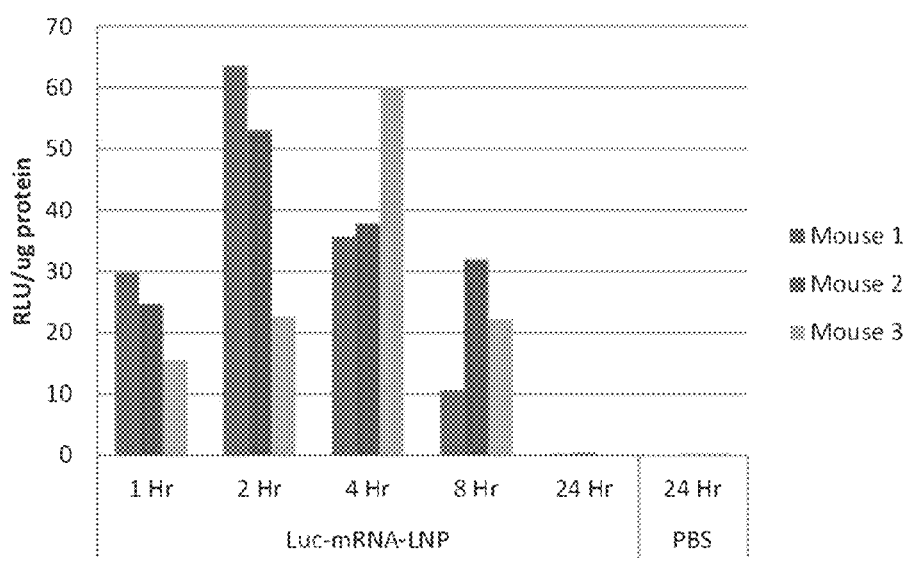
FIG. 1 shows time course of luciferase expression in mouse liver.

In the following description, certain specific details are set forth in order to provide a thorough understanding of various embodiments of the invention. However, one skilled in the art will understand that the invention may be practiced without these details.

The present invention is based, in part, upon the discovery of novel cationic (amino) lipids that provide advantages when used in lipid nanoparticles for the in vivo delivery of an active or therapeutic agent such as a nucleic acid into a cell of a mammal. In particular, embodiments of the present invention provide nucleic acid-lipid nanoparticle compositions comprising one or more of the novel cationic lipids described herein that provide increased activity of the nucleic acid and improved tolerability of the compositions in vivo, resulting in a significant increase in the therapeutic index as compared to nucleic acid-lipid nanoparticle compositions previously described.

In particular embodiments, the present invention provides novel cationic lipids that enable the formulation of improved compositions for the in vitro and in vivo delivery of mRNA and/or other oligonucleotides. In some embodiments, these improved lipid nanoparticle compositions are useful for expression of protein encoded by mRNA. In other embodiments, these improved lipid nanoparticles compositions are useful for upregulation of endogenous protein expression by delivering miRNA inhibitors targeting one specific miRNA or a group of miRNA regulating one target mRNA or several mRNA. In other embodiments, these improved lipid nanoparticle compositions are useful for down-regulating (e.g., silencing) the protein levels and/or mRNA levels of target genes. In some other embodiments, the lipid nanoparticles are also useful for delivery of mRNA and plasmids for expression of transgenes. In yet other embodiments, the lipid nanoparticle compositions are useful for inducing a pharmacological effect resulting from expression of a protein, e.g increased production of red blood cells through the delivery of a suitable erythropoietin mRNA, or protection against infection through delivery of mRNA encoding for a suitable antibody.

The lipid nanoparticles and compositions of the present invention may be used for a variety of purposes, including the delivery of encapsulated or associated (e.g., complexed) therapeutic agents such as nucleic acids to cells, both in vitro and in vivo. Accordingly, embodiments of the present invention provide methods of treating or preventing diseases or disorders in a subject in need thereof by contacting the subject with a lipid nanoparticle that encapsulates or is associated with a suitable therapeutic agent, wherein the lipid nanoparticle comprises one or more of the novel cationic lipids described herein.

As described herein, embodiments of the lipid nanoparticles of the present invention are particularly useful for the delivery of nucleic acids, including, e.g., mRNA, antisense oligonucleotide, plasmid DNA, microRNA (miRNA), miRNA inhibitors (antagomirs/antimirs), messenger-RNA-interfering complementary RNA (micRNA), DNA, multivalent RNA, dicer substrate RNA, complementary DNA (cDNA), etc. Therefore, the lipid nanoparticles and compositions of the present invention may be used to induce expression of a desired protein both in vitro and in vivo by contacting cells with a lipid nanoparticle comprising one or more novel cationic lipids described herein, wherein the lipid nanoparticle encapsulates or is associated with a nucleic acid that is expressed to produce the desired protein (e.g., a messenger RNA or plasmid encoding the desired protein). Alternatively, the lipid nanoparticles and compositions of the present invention may be used to decrease the expression of target genes and proteins both in vitro and in vivo by contacting cells with a lipid nanoparticle comprising one or more novel cationic lipids described herein, wherein the lipid nanoparticle encapsulates or is associated with a nucleic acid that reduces target gene expression (e.g., an antisense oligonucleotide or small interfering RNA (siRNA)). The lipid nanoparticles and compositions of the present invention may also be used for co-delivery of different nucleic acids (e.g. mRNA and plasmid DNA) separately or in combination, such as may be useful to provide an effect requiring colocalization of different nucleic acids (e.g. mRNA encoding for a suitable gene modifying enzyme and DNA segment(s) for incorporation into the host genome).

Nucleic acids for use with this invention may be prepared according to any available technique. For mRNA, the primary methodology of preparation is, but not limited to, enzymatic synthesis (also termed in vitro transcription) which currently represents the most efficient method to produce long sequence-specific mRNA. In vitro transcription describes a process of template-directed synthesis of RNA molecules from an engineered DNA template comprised of an upstream bacteriophage promoter sequence (e.g. including but not limited to that from the T7, T3 and SP6 coliphage) linked to a downstream sequence encoding the gene of interest. Template DNA can be prepared for in vitro transcription from a number of sources with appropriate techniques which are well known in the art including, but not limited to, plasmid DNA and polymerase chain reaction amplification (see Linpinsel, J. L and Conn, G. L., General protocols for preparation of plasmid DNA template and Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012)

Transcription of the RNA occurs in vitro using the linearized DNA template in the presence of the corresponding RNA polymerase and adenosine, guanosine, uridine and cytidine ribonucleoside triphosphates (rNTPs) under conditions that support polymerase activity while minimizing potential degradation of the resultant mRNA transcripts. In vitro transcription can be performed using a variety of commercially available kits including, but not limited to RiboMax Large Scale RNA Production System (Promega), MegaScript Transcription kits (Life Technologies) as well as with commercially available reagents including RNA polymerases and rNTPs. The methodology for in vitro transcription of mRNA is well known in the art. (see, e.g. Losick, R., 1972, In vitro transcription, Ann Rev Biochem v. 41 409-46; Kamakaka, R. T. and Kraus, W. L. 2001. In Vitro Transcription. Current Protocols in Cell Biology. 2:11.6:11.6.1-11.6.17; Beckert, B. And Masquida, B., (2010) Synthesis of RNA by In Vitro Transcription in RNA in Methods in Molecular Biology v. 703 (Neilson, H. Ed), New York, N.Y. Humana Press, 2010; Brunelle, J. L. and Green, R., 2013, Chapter Five—In vitro transcription from plasmid or PCR-amplified DNA, Methods in Enzymology v. 530, 101-114; all of which are incorporated herein by reference).

The desired in vitro transcribed mRNA is then purified from the undesired components of the transcription or associated reactions (including unincorporated rNTPs, protein enzyme, salts, short RNA oligos etc). Techniques for the isolation of the mRNA transcripts are well known in the art. Well known procedures include phenol/chloroform extraction or precipitation with either alcohol (ethanol, isopropanol) in the presence of monovalent cations or lithium chloride. Additional, non-limiting examples of purification procedures which can be used include size exclusion chromatography (Lukaysky, P. J. and Puglisi, J. D., 2004, Large-scale preparation and purification of polyacrylamide-free RNA oligonucleotides, RNA v. 10, 889-893), silica-based affinity chromatography and polyacrylamide gel electrophoresis (Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012). Purification can be performed using a variety of commercially available kits including, but not limited to SV Total Isolation System (Promega) and In Vitro Transcription Cleanup and Concentration Kit (Norgen Biotek).

Furthermore, while reverse transcription can yield large quantities of mRNA, the products can contain a number of aberrant RNA impurities associated with undesired polymerase activity which may need to be removed from the full-length mRNA preparation. These include short RNAs that result from abortive transcription initiation as well as double-stranded RNA (dsRNA) generated by RNA-dependent RNA polymerase activity, RNA-primed transcription from RNA templates and self-complementary 3' extension. It has been demonstrated that these contaminants with dsRNA structures can lead to undesired immunostimulatory activity through interaction with various innate immune sensors in eukaryotic cells that function to recognize specific nucleic acid structures and induce potent immune responses. This in turn, can dramatically reduce mRNA translation since protein synthesis is reduced during the innate cellular immune response. Therefore, additional techniques to remove these dsRNA contaminants have been developed and are known in the art including but not limited to scaleable HPLC purification (see e.g. Kariko, K., Muramatsu, H., Ludwig, J. And Weissman, D., 2011, Generating the optimal mRNA for therapy: HPLC purification eliminates immune activation and improves translation of nucleoside-modified, protein-encoding mRNA, Nucl Acid Res, v. 39 e142; Weissman, D., Pardi, N., Muramatsu, H., and Kariko, K., HPLC Purification of in vitro transcribed long RNA in Synthetic Messenger RNA and Cell Metabolism Modulation in Methods in Molecular Biology v. 969 (Rabinovich, P. H. Ed), 2013). HPLC purified mRNA has been reported to be translated at much greater levels, particularly in primary cells and in vivo.

A significant variety of modifications have been described in the art which are used to alter specific properties of in vitro transcribed mRNA, and improve its utility. These include, but are not limited to modifications to the 5' and 3' termini of the mRNA. Endogenous eukaryotic mRNA typically contain a cap structure on the 5'-end of a mature molecule which plays an important role in mediating binding of the mRNA Cap Binding Protein (CBP), which is in turn responsible for enhancing mRNA stability in the cell and efficiency of mRNA translation. Therefore, highest levels of protein expression are achieved with capped mRNA transcripts. The 5'-cap contains a 5'-5'-triphosphate linkage between the 5'-most nucleotide and guanine nucleotide. The conjugated guanine nucleotide is methylated at the N7 position. Additional modifications include methylation of the ultimate and penultimate most 5'-nucleotides on the 2'-hydroxyl group.

Multiple distinct cap structures can be used to generate the 5'-cap of in vitro transcribed synthetic mRNA. 5'-capping of synthetic mRNA can be performed co-transcriptionally with chemical cap analogs (i.e. capping during in vitro transcription). For example, the Anti-Reverse Cap Analog (ARCA) cap contains a 5'-5'-triphosphate guanine-guanine linkage where one guanine contains an N7 methyl group as well as a 3'-O-methyl group. However, up to 20% of transcripts remain uncapped during this co-transcriptional process and the synthetic cap analog is not identical to the 5'-cap structure of an authentic cellular mRNA, potentially reducing translatability and cellular stability. Alternatively, synthetic mRNA molecules may also be enzymatically capped post-transcriptionally. These may generate a more authentic 5'-cap structure that more closely mimics, either structurally or functionally, the endogenous 5'-cap which have enhanced binding of cap binding proteins, increased half life, reduced susceptibility to 5' endonucleases and/or reduced 5' decapping. Numerous synthetic 5'-cap analogs have been developed and are known in the art to enhance mRNA stability and translatability (see eg. Grudzien-Nogalska, E., Kowalska, J., Su, W., Kuhn, A. N., Slepenkov, S. V., Darynkiewicz, E., Sahin, U., Jemiality, J., and Rhoads, R. E., Synthetic mRNAs with superior translation and stability properties in Synthetic Messenger RNA and Cell Metabolism Modulation in Methods in Molecular Biology v. 969 (Rabinovich, P. H. Ed), 2013).

On the 3'-terminus, a long chain of adenine nucleotides (poly-A tail) is normally added to mRNA molecules during RNA processing. Immediately after transcription, the 3' end of the transcript is cleaved to free a 3' hydroxyl to which poly-A polymerase adds a chain of adenine nucleotides to the RNA in a process called polyadenylation. The poly-A tail has been extensively shown to enhance both translational efficiency and stability of mRNA (see Bernstein, P. and Ross, J., 1989, Poly (A), poly (A) binding protein and the regulation of mRNA stability, Trends Bio Sci v. 14 373-377; Guhaniyogi, J. And Brewer, G., 2001, Regulation of mRNA stability in mammalian cells, Gene, v. 265, 11-23; Dreyfus, M. And Regnier, P., 2002, The poly (A) tail of mRNAs: Bodyguard in eukaryotes, scavenger in bacteria, Cell, v. 111, 611-613).

Poly (A) tailing of in vitro transcribed mRNA can be achieved using various approaches including, but not limited to, cloning of a poly (T) tract into the DNA template or by post-transcriptional addition using Poly (A) polymerase. The first case allows in vitro transcription of mRNA with poly (A) tails of defined length, depending on the size of the poly (T) tract, but requires additional manipulation of the template. The latter case involves the enzymatic addition of a poly (A) tail to in vitro transcribed mRNA using poly (A) polymerase which catalyzes the incorporation of adenine residues onto the 3'termini of RNA, requiring no additional manipulation of the DNA template, but results in mRNA with poly(A) tails of heterogenous length. 5'-capping and 3'-poly (A) tailing can be performed using a variety of commercially available kits including, but not limited to Poly (A) Polymerase Tailing kit (EpiCenter), mMESSAGE mMACHINE T7 Ultra kit and Poly (A) Tailing kit (Life Technologies) as well as with commercially available reagents, various ARCA caps, Poly (A) polymerase, etc.

In addition to 5' cap and 3' poly adenylation, other modifications of the in vitro transcripts have been reported to provide benefits as related to efficiency of translation and stability. It is well known in the art that pathogenic DNA and RNA can be recognized by a variety of sensors within eukaryotes and trigger potent innate immune responses. The ability to discriminate between pathogenic and self DNA and RNA has been shown to be based, at least in part, on structure and nucleoside modifications since most nucleic acids from natural sources contain modified nucleosides In contrast, in vitro synthesized RNA lacks these modifications, thus rendering it immunostimulatory which in turn can inhibit effective mRNA translation as outlined above. The introduction of modified nucleosides into in vitro transcribed mRNA can be used to prevent recognition and activation of RNA sensors, thus mitigating this undesired immunostimulatory activity and enhancing translation capacity (see eg. Kariko, K. And Weissman, D. 2007, Naturally occurring nucleoside modifications suppress the immunostimulatory activity of RNA: implication for therapeutic RNA development, Curr Opin Drug Discov Devel, v. 10 523-532; Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013); Kariko, K., Muramatsu, H., Welsh, F. A., Ludwig, J., Kato, H., Akira, S., Weissman, D., 2008, Incorporation of Pseudouridine Into mRNA Yields Superior Non-immunogenic Vector With Increased Translational Capacity and Biological Stability, Mol Ther v. 16, 1833-1840. The modified nucleosides and nucleotides used in the synthesis of modified RNAs can be prepared monitored and utilized using general methods and procedures known in the art. A large variety of nucleoside modifications are available that may be incorporated alone or in combination with other modified nucleosides to some extent into the in vitro transcribed mRNA (see eg. US2012/0251618). In vitro synthesis of nucleoside-modified mRNA have been reported to have reduced ability to activate immune sensors with a concomitant enhanced translational capacity.

Other components of mRNA which can be modified to provide benefit in terms of translatability and stability include the 5' and 3' untranslated regions (UTR). Optimization of the UTRs (favorable 5' and 3' UTRs can be obtained from cellular or viral RNAs), either both or independently, have been shown to increase mRNA stability and translational efficiency of in vitro transcribed mRNA (see eg. Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v.969 (Rabinovich, P. H. Ed), 2013).

In addition to mRNA, other nucleic acid payloads may be used for this invention. For oligonucleotides, methods of preparation include but are not limited to chemical synthesis and enzymatic, chemical cleavage of a longer precursor, in vitro transcription as described above, etc. Methods of synthesizing DNA and RNA nucleotides are widely used and well known in the art (see, e.g., Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

For plasmid DNA, preparation for use with this invention commonly utilizes but is not limited to expansion and isolation of the plasmid DNA in vitro in a liquid culture of bacteria containing the plasmid of interest. The presence of a gene in the plasmid of interest that encodes resistance to a particular antibiotic (penicillin, kanamycin, etc) allows those bacteria containing the plasmid of interest to selective grow in antibiotic-containing cultures. Methods of isolating plasmid DNA are widely used and well known in the art (see, e.g. Heilig, J., Elbing, K. L. and Brent, R (2001) Large-Scale Preparation of Plasmid DNA. Current Protocols in Molecular Biology. 41:11:1.7:1.7.1-1.7.16; Rozkov, A., Larsson, B., Gillström, S., Björnestedt, R. and Schmidt, S. R. (2008), Large-scale production of endotoxin-free plasmids for transient expression in mammalian cell culture. Biotechnol. Bioeng., 99: 557-566; and U.S. Pat. No. 6,197, 553B1). Plasmid isolation can be performed using a variety of commercially available kits including, but not limited to Plasmid Plus (Qiagen), GenJET plasmid MaxiPrep (Thermo) and PureYield MaxiPrep (Promega) kits as well as with commercially available reagents.

Various exemplary embodiments of the cationic lipids of the present invention, lipid nanoparticles and compositions comprising the same, and their use to deliver active or therapeutic agents such as nucleic acids to modulate gene and protein expression, are described in further detail below.

As used herein, the following terms have the meanings ascribed to them unless specified otherwise.

Unless the context requires otherwise, throughout the present specification and claims, the word "comprise" and variations thereof, such as, "comprises" and "comprising" are to be construed in an open and inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

The phrase "induce expression of a desired protein" refers to the ability of a nucleic acid to increase expression of the desired protein. To examine the extent of protein expression, a test sample (e.g., a sample of cells in culture expressing the desired protein) or a test mammal (e.g., a mammal such as a human or an animal model such as a rodent (e.g., mouse) or a non-human primate (e.g., monkey) model) is contacted with a nucleic acid (e.g., nucleic acid in combination with a lipid of the present invention). Expression of the desired protein in the test sample or test animal is compared to expression of the desired protein in a control sample (e.g., a sample of cells in culture expressing the desired protein) or a control mammal (e.g., a mammal such as a human or an animal model such as a rodent (e.g., mouse) or non-human primate (e.g., monkey) model) that is not contacted with or administered the nucleic acid. When the desired protein is present in a control sample or a control mammal, the expression of a desired protein in a control sample or a control mammal may be assigned a value of 1.0. In particular embodiments, inducing expression of a desired protein is achieved when the ratio of desired protein expression in the test sample or the test mammal to the level of desired protein expression in the control sample or the control mammal is greater than 1, for example, about 1.1, 1.5, 2.0. 5.0 or 10.0. When a desired protein is not present in a control sample or a control mammal, inducing expression of a desired protein is achieved when any measurable level of the desired protein in the test sample or the test mammal is detected. One of ordinary skill in the art will understand appropriate assays to determine the level of protein expression in a sample, for example dot blots, northern blots, in situ hybridization, ELISA, immunoprecipitation, enzyme function, and phenotypic assays, or assays based on reporter proteins that can produce fluorescence or luminescence under appropriate conditions.

The phrase "inhibiting expression of a target gene" refers to the ability of a nucleic acid to silence, reduce, or inhibit the expression of a target gene. To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with a nucleic acid that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the nucleic acid. The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the nucleic acids are capable of silencing, reducing, or inhibiting the expression of a target gene by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the nucleic acid. Suitable assays for determining the level of target gene expression include, without limitation, examination of protein or mRNA levels using techniques known to those of skill in the art, such as, e.g., dot blots, northern blots, in situ hybridization, ELISA, immunoprecipitation, enzyme function, as well as phenotypic assays known to those of skill in the art.

An "effective amount" or "therapeutically effective amount" of an active agent or therapeutic agent such as a therapeutic nucleic acid is an amount sufficient to produce the desired effect, e.g., an increase or inhibition of expression of a target sequence in comparison to the normal expression level detected in the absence of the nucleic acid. An increase in expression of a target sequence is achieved when any measurable level is detected in the case of an expression product that is not present in the absence of the nucleic acid. In the case where the expression product is present at some level prior to contact with the nucleic acid, an in increase in expression is achieved when the fold increase in value obtained with a nucleic acid such as mRNA relative to control is about 1.05, 1.1, 1.2, 1.3, 1.4, 1.5, 1.75, 2, 2.5, 3, 4, 5, 6, 7, 8, 9, 10, 15, 20, 25, 30, 40, 50, 75, 100, 250, 500, 750, 1000, 5000, 10000 or greater. Inhibition of expression of a target gene or target sequence is achieved when the value obtained with a nucleic acid such as antisense oligonucleotide relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, fluorescence or luminescence of suitable reporter proteins, as well as phenotypic assays known to those of skill in the art.

The term "nucleic acid" as used herein refers to a polymer containing at least two deoxyribonucleotides or ribonucleotides in either single- or double-stranded form and includes DNA, RNA, and hybrids thereof. DNA may be in the form of antisense molecules, plasmid DNA, cDNA, PCR products, or vectors. RNA may be in the form of small hairpin RNA (shRNA), messenger RNA (mRNA), antisense RNA, miRNA, micRNA, multivalent RNA, dicer substrate RNA or viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, single nucleotide polymorphisms, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are generally characterized by being poorly soluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "steroid" is a compound comprising the following carbon skeleton:

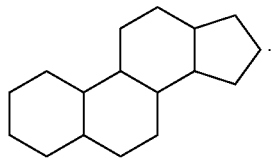 [SMILES: C1CCC2C(C1)CCC1C3CCCC3CCC21]

Non-limiting examples of steroids include cholesterol, and the like.

A "cationic lipid" refers to a lipid capable of being positively charged. Exemplary cationic lipids include one or more amine group(s) which bear the positive charge. Preferred cationic lipids are ionizable such that they can exist in a positively charged or neutral form depending on pH. The ionization of the cationic lipid affects the surface charge of the lipid nanoparticle under different pH conditions. This charge state can influence plasma protein absorption, blood clearance and tissue distribution (Semple, S. C., et al., Adv. Drug Deliv Rev 32:3-17 (1998)) as well as the ability to form endosomolytic non-bilayer structures (Hafez, I. M., et al., Gene Ther 8:1188-1196 (2001)) critical to the intracellular delivery of nucleic acids.

The term "lipid nanoparticle" refers to particles having at least one dimension on the order of nanometers (e.g., 1-1,000 nm) which include one or more of the compounds of formula (I) or other specified cationic lipids. In some embodiments, lipid nanoparticles are included in a formulation that can be used to deliver an active agent or therapeutic agent, such as a nucleic acid (e.g., mRNA) to a target site of interest (e.g., cell, tissue, organ, tumor, and the like). In some embodiments, the lipid nanoparticles of the invention comprise a nucleic acid. Such lipid nanoparticles typically comprise a compound of Formula (I) and one or more excipient selected from neutral lipids, charged lipids, steroids and polymer conjugated lipids. In some embodiments, the active agent or therapeutic agent, such as a nucleic acid, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, nucleic acids, when present in the lipid nanoparticles, are resistant in aqueous solution to degradation with a nuclease. Lipid nanoparticles comprising nucleic acids and their method of preparation are disclosed in, e.g., U.S. Patent Publication Nos. 2004/0142025, 2007/0042031 and PCT Pub. Nos. WO 2013/016058 and WO 2013/086373, the full disclosures of which are herein incorporated by reference in their entirety for all purposes.

As used herein, "lipid encapsulated" refers to a lipid nanoparticle that provides an active agent or therapeutic agent, such as a nucleic acid (e.g., mRNA), with full encapsulation, partial encapsulation, or both. In an embodiment, the nucleic acid (e.g., mRNA) is fully encapsulated in the lipid nanoparticle.

The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-DMG) and the like.

The term "neutral lipid" refers to any of a number of lipid species that exist either in an uncharged or neutral zwitterionic form at a selected pH. At physiological pH, such lipids include, but are not limited to, phosphotidylcholines such as 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), phophatidylethanolamines such as 1,2-Dioleoyl-sn-glycero-3-phosphoethanolamine (DOPE), sphingomyelins (SM), ceramides, steroids such as sterols and their derivatives. Neutral lipids may be synthetic or naturally derived.

The term "charged lipid" refers to any of a number of lipid species that exist in either a positively charged or negatively charged form independent of the pH within a useful physiological range e.g. pH~3 to pH~9. Charged lipids may be synthetic or naturally derived. Examples of charged lipids include phosphatidylserines, phosphatidic acids, phosphatidylglycerols, phosphatidylinositols, sterol hemisuccinates, dialkyl trimethylammonium-propanes, (e.g. DOTAP, DOTMA), dialkyl dimethylaminopropanes, ethyl phosphocholines, dimethylaminoethane carbamoyl sterols (e.g. DC-Chol).

As used herein, the term "aqueous solution" refers to a composition comprising water.

"Serum-stable" in relation to nucleic acid-lipid nanoparticles means that the nucleotide is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of a therapeutic product that can result in a broad exposure of an active agent within an organism. Some techniques of administration can lead to the systemic delivery of certain agents, but not others. Systemic delivery means that a useful, preferably therapeutic, amount of an agent is exposed to most parts of the body. Systemic delivery of lipid nanoparticles can be by any means known in the art including, for example, intravenous, intraarterial, subcutaneous, and intraperitoneal delivery. In some embodiments, systemic delivery of lipid nanoparticles is by intravenous delivery.

"Local delivery," as used herein, refers to delivery of an active agent directly to a target site within an organism. For example, an agent can be locally delivered by direct injection into a disease site such as a tumor, other target site such as a site of inflammation, or a target organ such as the liver, heart, pancreas, kidney, and the like. Local delivery can also include topical applications or localized injection techniques such as intramuscular, subcutaneous or intradermal injection. Local delivery does not preclude a systemic pharmacological effect.

"Alkyl" refers to a straight or branched hydrocarbon chain radical consisting solely of carbon and hydrogen atoms, which is saturated or unsaturated (i.e., contains one or more double and/or triple bonds), having from one to twenty-four carbon atoms ($C_1$-$C_{24}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond, e.g., methyl, ethyl, n propyl, 1 methylethyl (iso propyl), n butyl, n pentyl, 1,1 dimethylethyl (t butyl), 3 methylhexyl, 2 methylhexyl, ethenyl, prop 1 enyl, but 1 enyl, pent 1 enyl, penta 1,4 dienyl, ethynyl, propynyl, butynyl, pentynyl, hexynyl, and the like. Unless otherwise specifically in the specification, an alkyl group is optionally substituted.

"Cycloalkyl" or "carbocyclic ring" refers to a stable non aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7 dimethyl bicyclo[2.2.1] heptanyl, and the like. Unless otherwise stated specifically in the specification, a cycloalkyl group is optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

The term "substituted" used herein means any of the above groups (e.g., alkyl, cycloalkyl or heterocyclyl) wherein at least one hydrogen atom is replaced by a bond to a non-hydrogen atoms such as, but not limited to: a halogen atom such as F, Cl, Br, and I; oxo groups (=O); hydroxyl groups (—OH); alkoxy groups (—OR$^a$, where R$^a$ is $C_1$-$C_{12}$ alkyl or cycloalkyl); carboxyl groups (—OC(=O)R$^a$ or —C(=O)OR$^a$, where R$^a$ is H, $C_1$-$C_{12}$ alkyl or cycloalkyl); amine groups (—NR$^a$R$^b$, where R$^a$ and R$^b$ are each independently H, $C_1$-$C_{12}$ alkyl or cycloalkyl); $C_1$-$C_{12}$ alkyl groups; and cycloalkyl groups. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is a oxo group. In other embodiments, the substituent is a hydroxyl group. In other embodiments, the substituent is an alkoxy group. In other embodiments, the substituent is a carboxyl group. In other embodiments, the substituent is an amine group.

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of the compound of Formula (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I) or (II), for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) or (II) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment in the mammal, preferably a human. The amount of a lipid nanoparticle of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Compounds

In an aspect, the invention provides novel lipid compounds which are capable of combining with other lipid components such as neutral lipids, charged lipids, steroids and/or polymer conjugated-lipids to form lipid nanoparticles with oligonucleotides. Without wishing to be bound by theory, it is thought that these lipid nanoparticles shield oligonucleotides from degradation in the serum and provide for effective delivery of oligonucleotides to cells in vitro and in vivo.

In one embodiment, the lipid compounds have the structure of Formula (I):

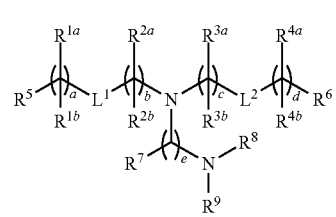

or a pharmaceutically acceptable salt, tautomer, prodrug or stereoisomer thereof, wherein:

$L^1$ and $L^2$ are each independently —O(C=O)—, —(C=O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2.

In certain embodiments of the Formula (I) compound at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—. In other embodiments, $R^{1a}$ and $R^{1b}$ are not isopropyl when a is 6 or n-butyl when a is 8.

In still further embodiments, at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—; and $R^{1a}$ and $R^{1b}$ are not isopropyl when a is 6 or n-butyl when a is 8.

In the compound of Formula I, any one of $L^1$ or $L^2$ may be —O(C=O)— or a carbon-carbon double bond. $L^1$ and $L^2$ may each be —O(C=O)— or may each be a carbon-carbon double bond.

In some embodiments, one of $L^1$ or $L^2$ is —O(C=O)—. In other embodiments, both $L^1$ and $L^2$ are —O(C=O)—.

In some embodiments, one of $L^1$ or $L^2$ is —(C=O)O—. In other embodiments, both $L^1$ and $L^2$ are —(C=O)O—.

In some embodiments, one of $L^1$ or $L^2$ is a carbon-carbon double bond. In other embodiments, both $L^1$ and $L^2$ are a carbon-carbon double bond.

In still other embodiments, one of $L^1$ or $L^2$ is —O(C=O)— and the other of $L^1$ or $L^2$ is —(C=O)O—. In more embodiments, one of $L^1$ or $L^2$ is —O(C=O)— and the other of $L^1$ or $L^2$ is a carbon-carbon double bond. In yet more embodiments, one of $L^1$ or $L^2$ is —(C=O)O— and the other of $L^1$ or $L^2$ is a carbon-carbon double bond.

It is understood that "carbon-carbon" double bond refers to one of the following structures:

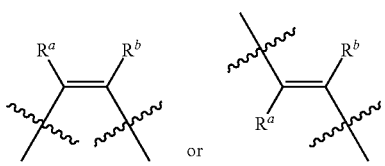

wherein $R^a$ and $R^b$ are, at each occurrence, independently H or a substituent. For example, in some embodiments $R^a$ and $R^b$ are, at each occurrence, independently H, $C_1$-$C_{12}$ alkyl or cycloalkyl, for example H or $C_1$-$C_{12}$ alkyl.

In other embodiments, the lipid compounds have the following structure (Ia):

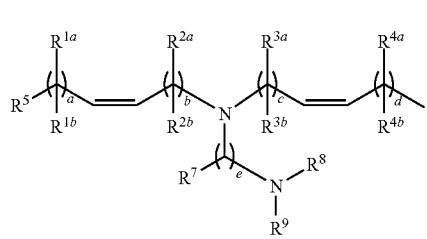

In other embodiments, the lipid compounds have the following structure (Ib):

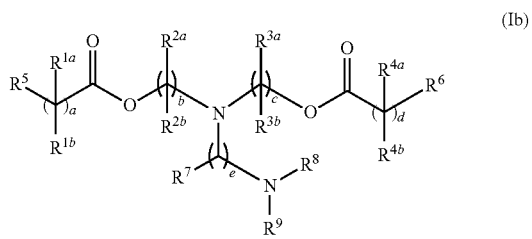

In yet other embodiments, the lipid compounds have the following structure (Ic):

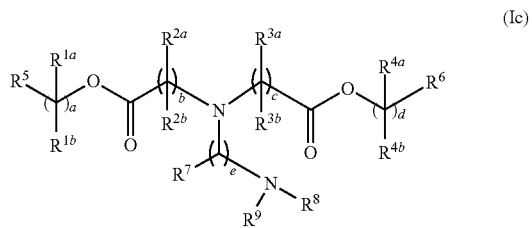

In certain embodiments of the foregoing, a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments, b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments, c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments, d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments, a and d are the same. In some other embodiments, b and c are the same. In some other specific embodiments and a and d are the same and b and c are the same.

The sum of a and b and the sum of c and d are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such the sum of a and b and the sum of c and d is 12 or greater.

In some embodiments, e is 1. In other embodiments, e is 2.

The substituents at $R^{1a}$, $R^{2a}$, $R^{3a}$ and $R^{4a}$ are not particularly limited. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of the foregoing, $R^{1a}$, $R^{1b}$, $R^{4a}$ and $R^{4b}$ are $C_1$-$C_{12}$ alkyl at each occurrence.

In further embodiments of the foregoing, at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of the foregoing, $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ are not particularly limited in the foregoing embodiments. In certain embodiments one or both of $R^5$ or $R^6$ is methyl. In certain other embodiments one or both of $R^5$ or $R^6$ is cycloalkyl for example cyclohexyl. In these embodiments the cycloalkyl may be substituted or not substituted. In certain other embodiments the cycloalkyl is substituted with $C_1$-$C_{12}$ alkyl, for example tert-butyl.

The substituents at $R^7$ are not particularly limited in the foregoing embodiments. In certain embodiments at least one $R^7$ is H. In some other embodiments, $R^7$ is H at each occurrence. In certain other embodiments $R^7$ is $C_1$-$C_{12}$ alkyl.

In certain other of the foregoing embodiments, one of $R^8$ or $R^9$ is methyl. In other embodiments, both $R^8$ and $R^9$ are methyl.

In some different embodiments, $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In various different embodiments, the compound has one of the structures set forth in Table 1 below.

TABLE 1

Representative Compounds

| No. | Structure | Preparation Method |
|-----|-----------|--------------------|
| 1 | 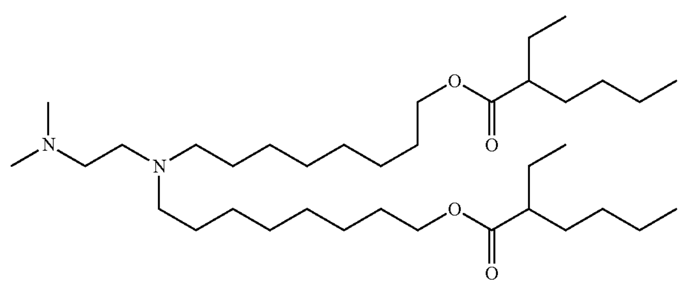 [SMILES: CCCCC(CC)C(=O)OCCCCCCCCN(CCCCCCCCOC(=O)C(CC)CCCC)CCN(C)C] | B |
| 2 | 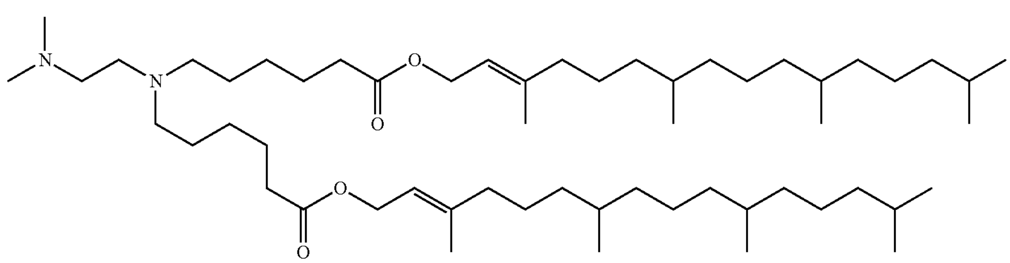 [SMILES: C/C(=C\COC(=O)CCCCCN(CCCCCC(=O)OC/C=C(\C)CCCC(C)CCCC(C)CCCC(C)C)CCN(C)C)CCCC(C)CCCC(C)CCCC(C)C] | A |

TABLE 1-continued
Representative Compounds
| No. | Structure | Preparation Method |
|---|---|---|
| 3 | 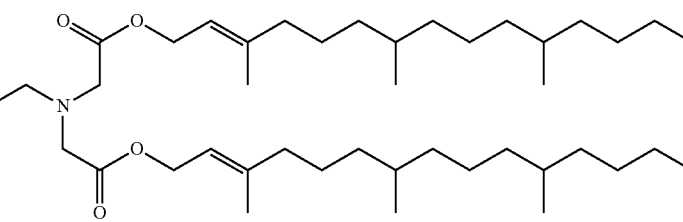 | A |
| 4 | 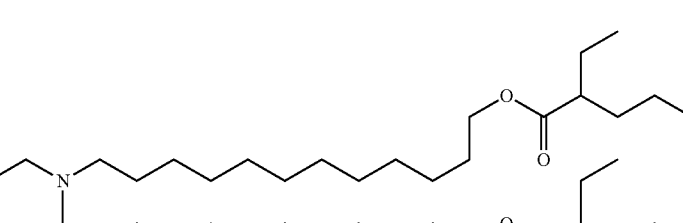 | B |
| 5 | 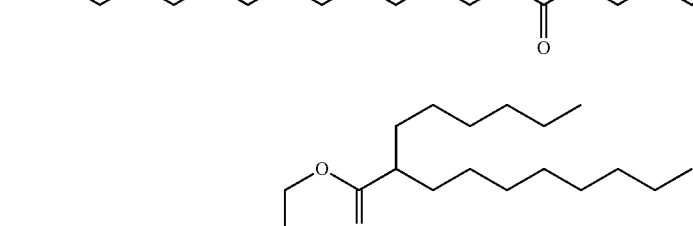 | B |
| 6 | 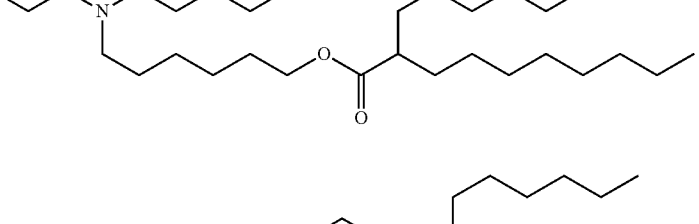 | B |
| 7 | 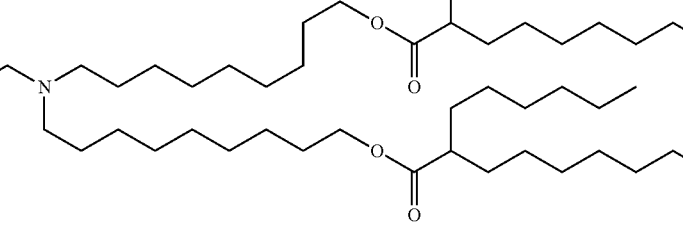 | A |

TABLE 1-continued
Representative Compounds
| No. | Structure | Preparation Method |
|---|---|---|
| 8 | 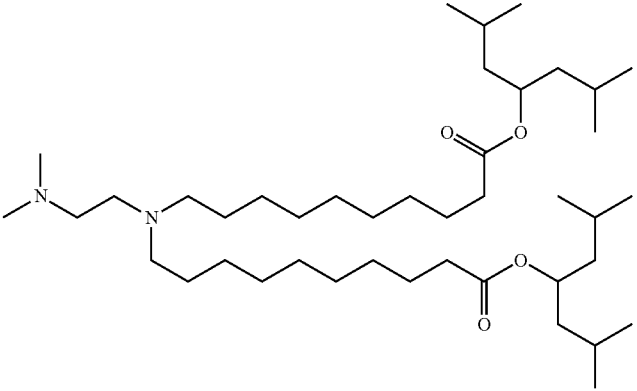 [SMILES: CC(C)CC(CC(C)C)OC(=O)CCCCCCCCCN(CCCCCCCCCC(=O)OC(CC(C)C)CC(C)C)CCN(C)C] | A |
| 9 | 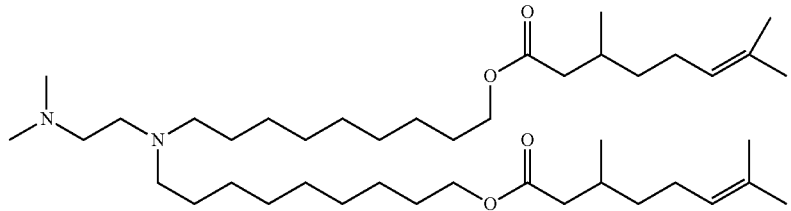 [SMILES: CC(C)=CCCC(C)CC(=O)OCCCCCCCCCN(CCCCCCCCCOC(=O)CC(C)CCC=C(C)C)CCN(C)C] | B |
| 10 | 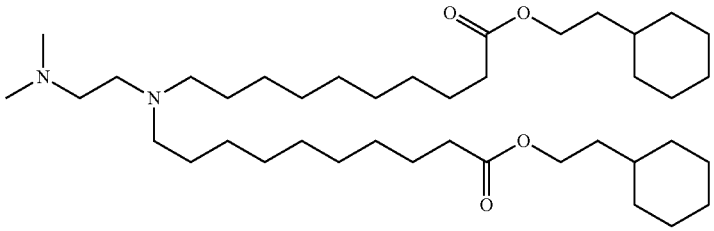 [SMILES: CN(C)CCN(CCCCCCCCCC(=O)OCCC1CCCCC1)CCCCCCCCCC(=O)OCCC1CCCCC1] | A |
| 11 | 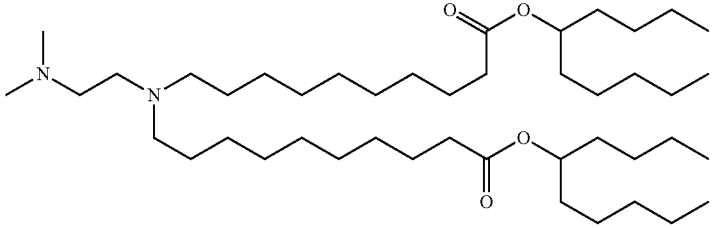 [SMILES: CCCCCC(CCCC)OC(=O)CCCCCCCCCN(CCCCCCCCCC(=O)OC(CCCC)CCCCC)CCN(C)C] | A |
| 12 | 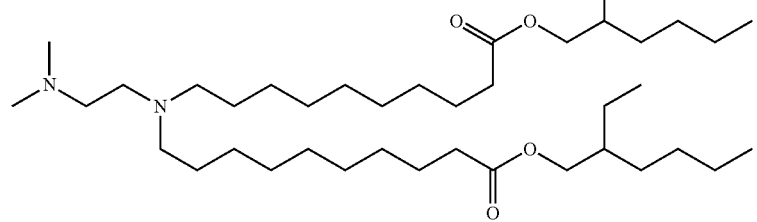 | A |

US 9,738,593 B2
TABLE 1-continued
Representative Compounds
| No. | Structure | Preparation Method |
|---|---|---|
| 13 | 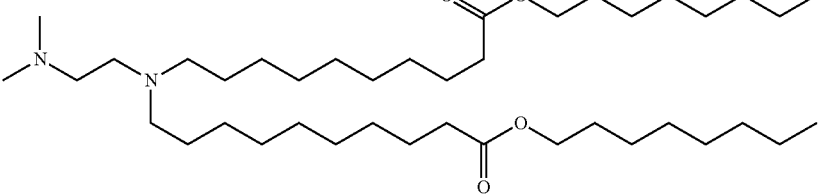 | A |
| 14 | 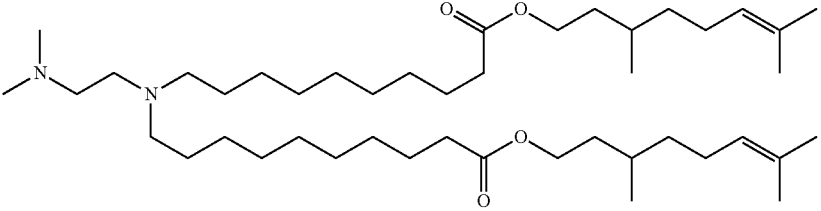 [SMILES: CC(C)=CCCC(C)CCOC(=O)CCCCCCCCCN(CCCCCCCCCC(=O)OCCC(C)CCC=C(C)C)CCN(C)C] | A |
| 15 | 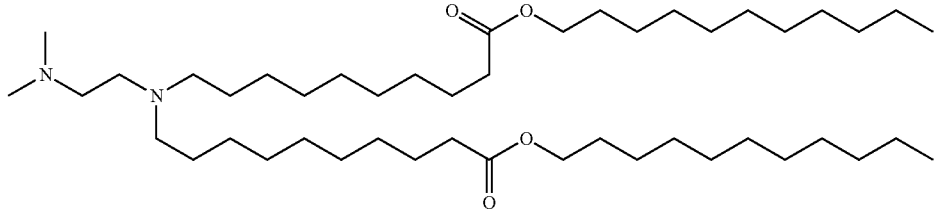 [SMILES: CCCCCCCCCCCOC(=O)CCCCCCCCCN(CCCCCCCCCC(=O)OCCCCCCCCCCC)CCN(C)C] | A |
| 16 | 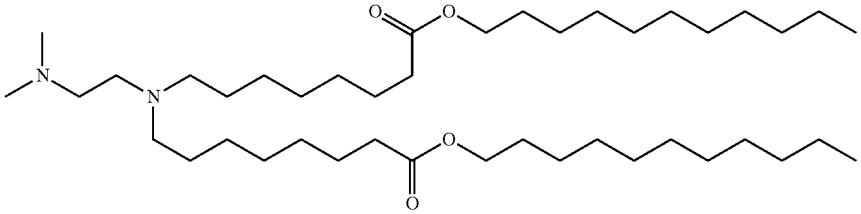 [SMILES: CCCCCCCCCCCOC(=O)CCCCCCCN(CCCCCCCC(=O)OCCCCCCCCCCC)CCN(C)C] | A |
| 17 | 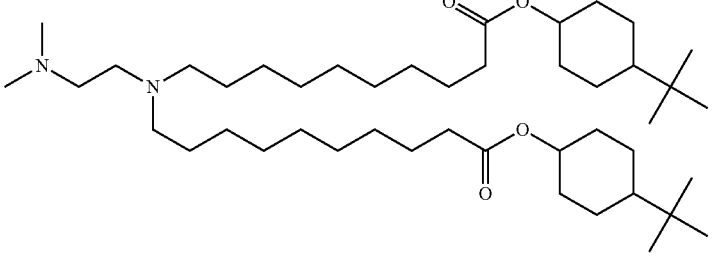 | A |
| 18 | 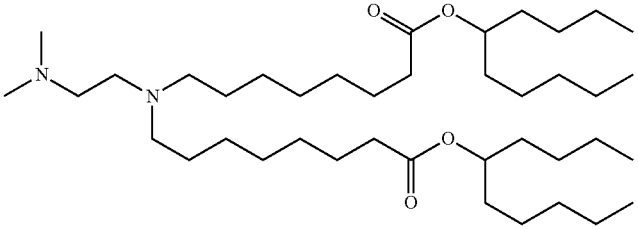 [SMILES: CCCCCC(CCCC)OC(=O)CCCCCCCN(CCCCCCCC(=O)OC(CCCC)CCCCC)CCN(C)C] | A |

TABLE 1-continued

Representative Compounds

| No. | Structure | Preparation Method |
|---|---|---|
| 19 | 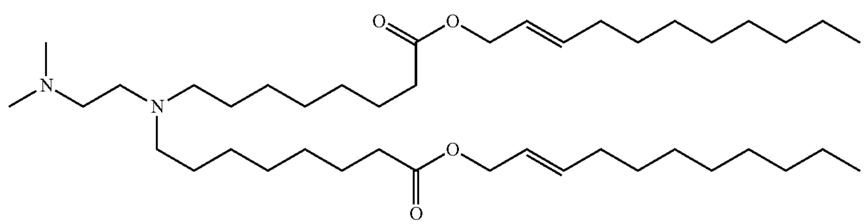 [SMILES: CCCCCCCC/C=C/COC(=O)CCCCCCCN(CCCCCCCC(=O)OC/C=C/CCCCCCCC)CCN(C)C] | A |
| 20 | 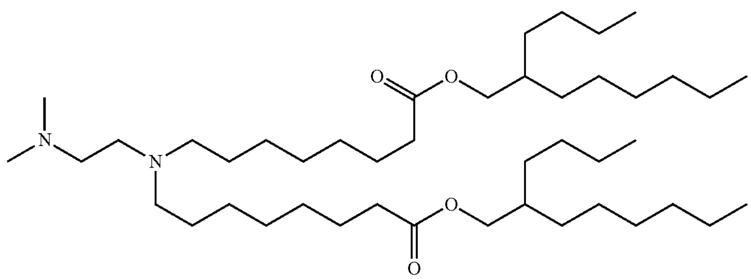 [SMILES: CCCCCCC(CCCC)COC(=O)CCCCCCCN(CCCCCCCC(=O)OCC(CCCC)CCCCCC)CCN(C)C] | A |
| 21 | 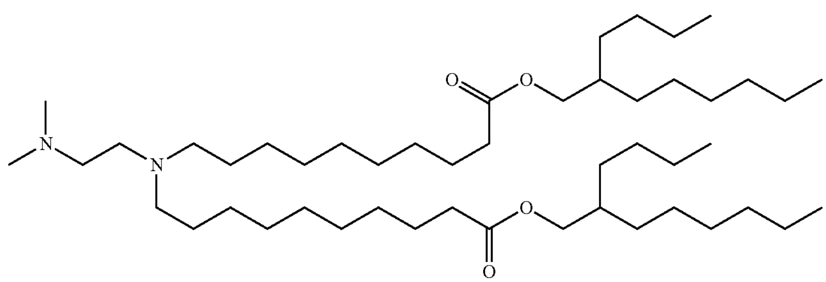 [SMILES: CCCCCCC(CCCC)COC(=O)CCCCCCCCCN(CCCCCCCCCC(=O)OCC(CCCC)CCCCCC)CCN(C)C] | A |
| 22 | 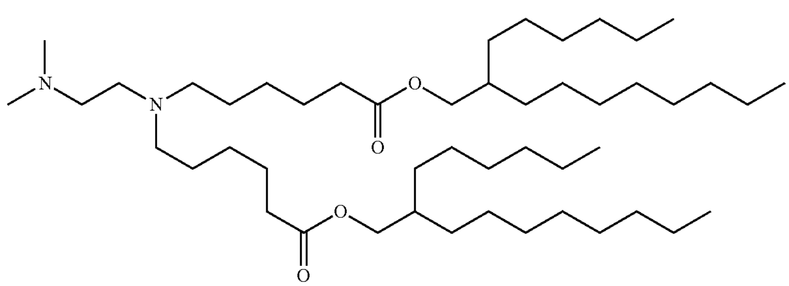 [SMILES: CCCCCCCCC(CCCCCC)COC(=O)CCCCCN(CCCCCC(=O)OCC(CCCCCC)CCCCCCCC)CCN(C)C] | A |
| 23 | 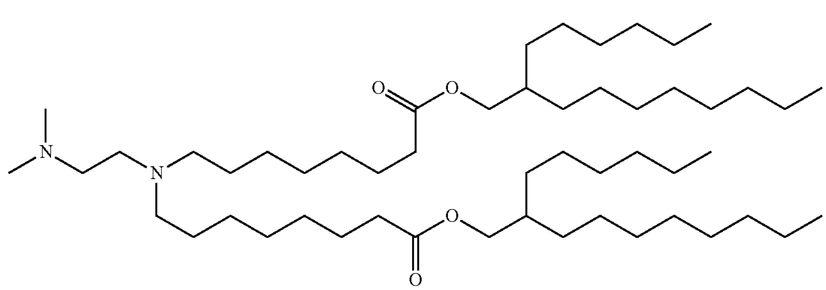 [SMILES: CCCCCCCCC(CCCCCC)COC(=O)CCCCCCCN(CCCCCCCC(=O)OCC(CCCCCC)CCCCCCCC)CCN(C)C] | A |

TABLE 1-continued
Representative Compounds
| No. | Structure | Preparation Method |
|---|---|---|
| 24 | 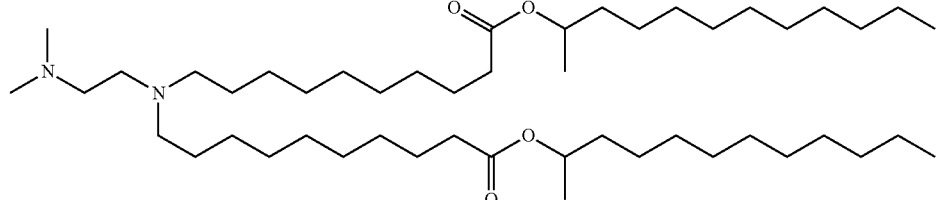 | A |
| 25 | 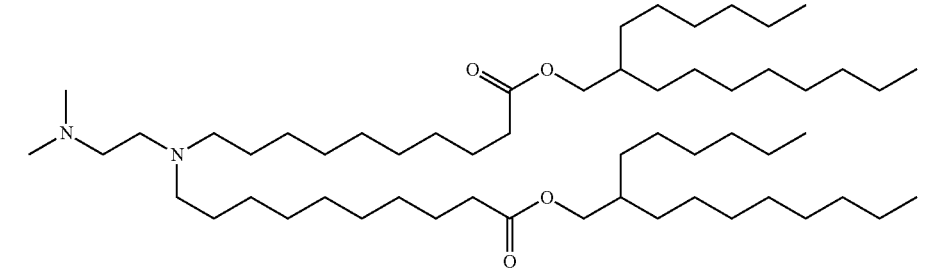 [SMILES: CCCCCCCCC(CCCCCC)COC(=O)CCCCCCCCCN(CCCCCCCCCC(=O)OCC(CCCCCC)CCCCCCCC)CCN(C)C] | A |
| 26 | 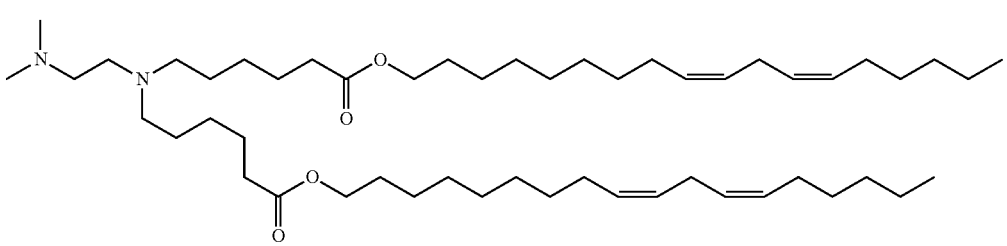 [SMILES: CCCCC/C=C\C/C=C\CCCCCCCCOC(=O)CCCCCN(CCCCCC(=O)OCCCCCCCC/C=C\C/C=C\CCCCC)CCN(C)C] | A |
| 27 | 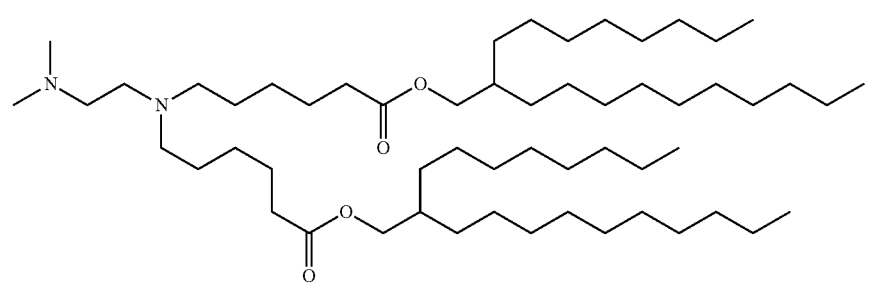 [SMILES: CCCCCCCCCCC(CCCCCCCC)COC(=O)CCCCCN(CCCCCC(=O)OCC(CCCCCCCC)CCCCCCCCCC)CCN(C)C] | A |
| 28 | 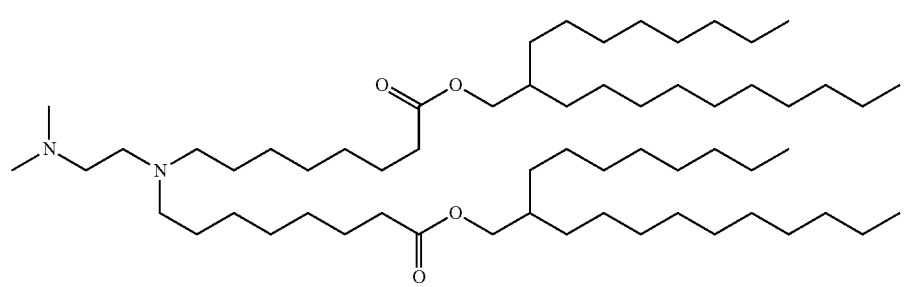 [SMILES: CCCCCCCCCCC(CCCCCCCC)COC(=O)CCCCCCCN(CCCCCCCC(=O)OCC(CCCCCCCC)CCCCCCCCCC)CCN(C)C] | A |
| 29 | 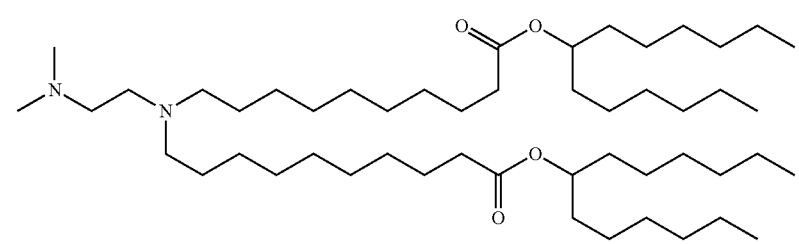 [SMILES: CCCCCCC(CCCCCC)OC(=O)CCCCCCCCCN(CCCCCCCCCC(=O)OC(CCCCCC)CCCCCC)CCN(C)C] | A |

TABLE 1-continued

Representative Compounds

| No. | Structure | Preparation Method |
|---|---|---|
| 30 | 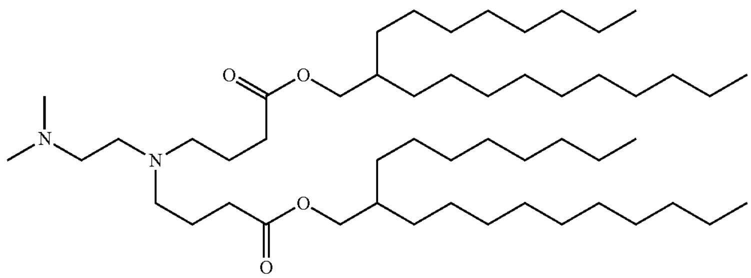 [SMILES: CCCCCCCCCCC(CCCCCCCC)COC(=O)CCCN(CCCC(=O)OCC(CCCCCCCC)CCCCCCCCCC)CCN(C)C] | A |
| 31 | 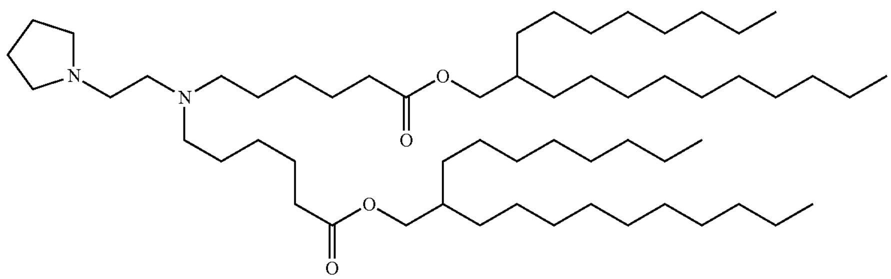 [SMILES: CCCCCCCCCCC(CCCCCCCC)COC(=O)CCCCCN(CCCCCC(=O)OCC(CCCCCCCC)CCCCCCCCCC)CCN1CCCC1] | C |
| 32 | 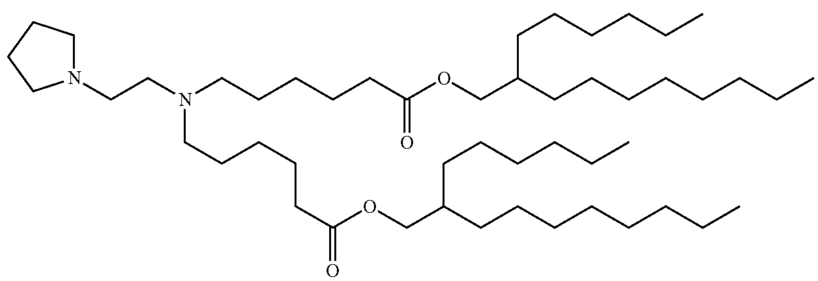 [SMILES: CCCCCCCCC(CCCCCC)COC(=O)CCCCCN(CCCCCC(=O)OCC(CCCCCC)CCCCCCCC)CCN1CCCC1] | C |
| 33 | 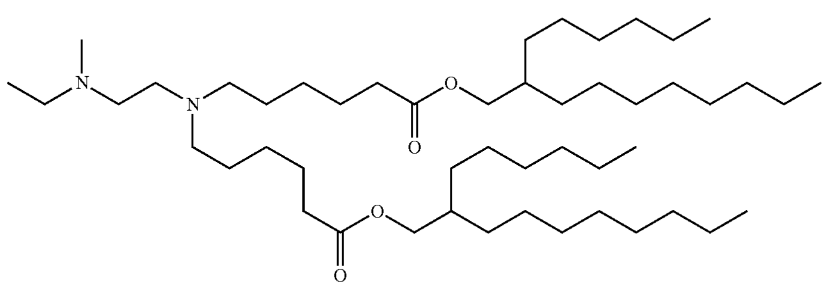 [SMILES: CCCCCCCCC(CCCCCC)COC(=O)CCCCCN(CCCCCC(=O)OCC(CCCCCC)CCCCCCCC)CCN(C)CC] | C |
| 34 | 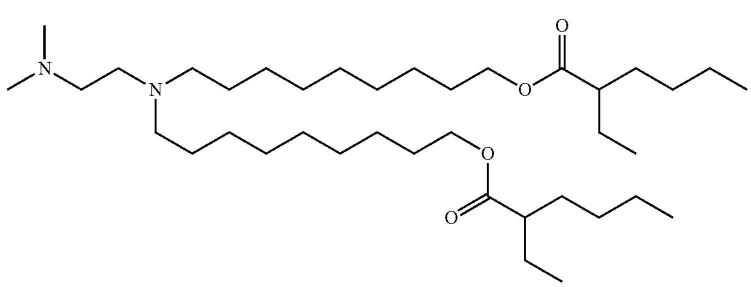 [SMILES: CCCCC(CC)C(=O)OCCCCCCCCCN(CCCCCCCCCOC(=O)C(CC)CCCC)CCN(C)C] | B |

TABLE 1-continued

Representative Compounds

| No. | Structure | Preparation Method |
|---|---|---|
| 35 | 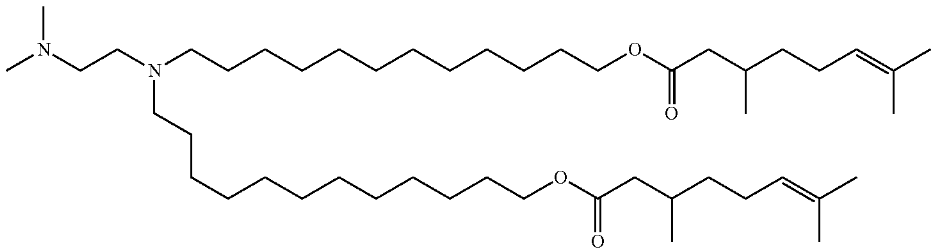 [SMILES: CC(C)=CCCC(C)CC(=O)OCCCCCCCCCCCCN(CCCCCCCCCCCCOC(=O)CC(C)CCC=C(C)C)CCN(C)C] | B |
| 36 | 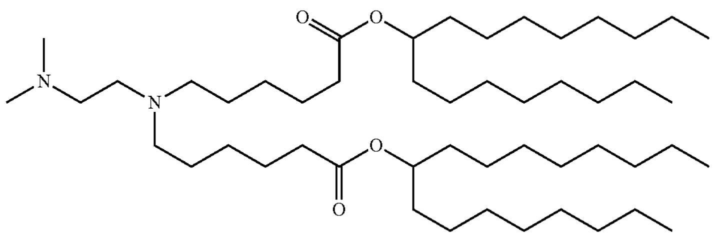 [SMILES: CCCCCCCCC(CCCCCCCC)OC(=O)CCCCCN(CCCCCC(=O)OC(CCCCCCCC)CCCCCCCC)CCN(C)C] | C |
| 37 | 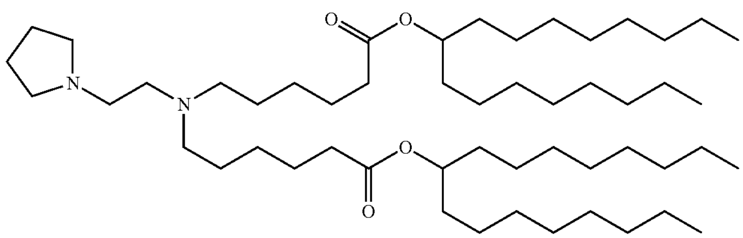 [SMILES: CCCCCCCCC(CCCCCCCC)OC(=O)CCCCCN(CCCCCC(=O)OC(CCCCCCCC)CCCCCCCC)CCN1CCCC1] | C |
| 38 | 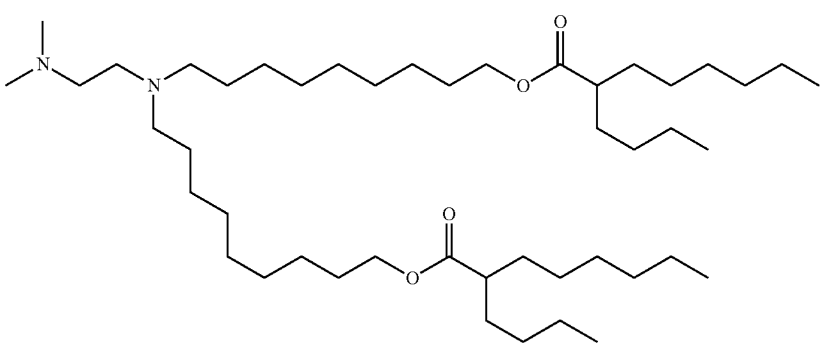 [SMILES: CCCCCCC(CCCC)C(=O)OCCCCCCCCCN(CCCCCCCCCOC(=O)C(CCCC)CCCCCC)CCN(C)C] | B |
| 39 | 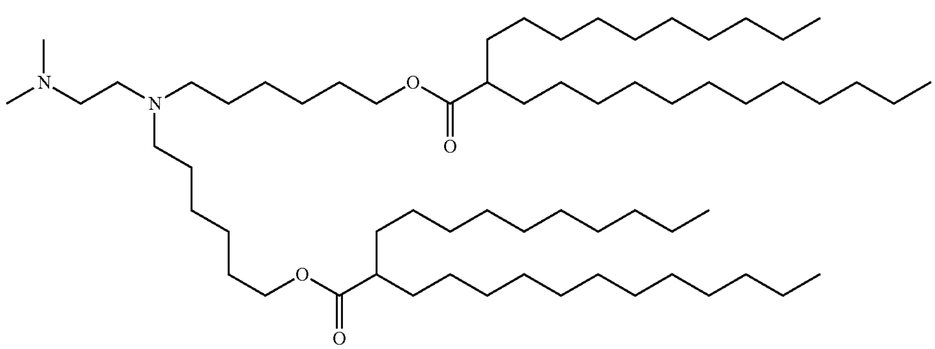 [SMILES: CCCCCCCCCCCCC(CCCCCCCCCC)C(=O)OCCCCCCN(CCCCCCOC(=O)C(CCCCCCCCCC)CCCCCCCCCCCC)CCN(C)C] | B |

TABLE 1-continued

Representative Compounds

| No. | Structure | Preparation Method |
|---|---|---|
| 40 | 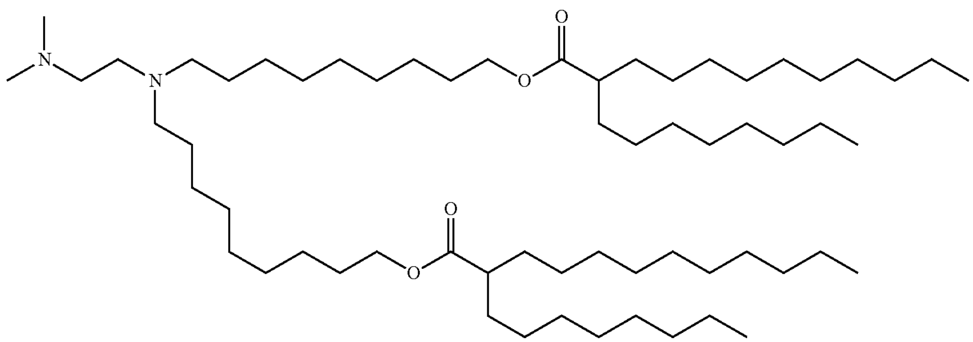 [SMILES: CCCCCCCCCCC(CCCCCCCC)C(=O)OCCCCCCCCCN(CCCCCCCCCOC(=O)C(CCCCCCCC)CCCCCCCCCC)CCN(C)C] | B |
| 41 | 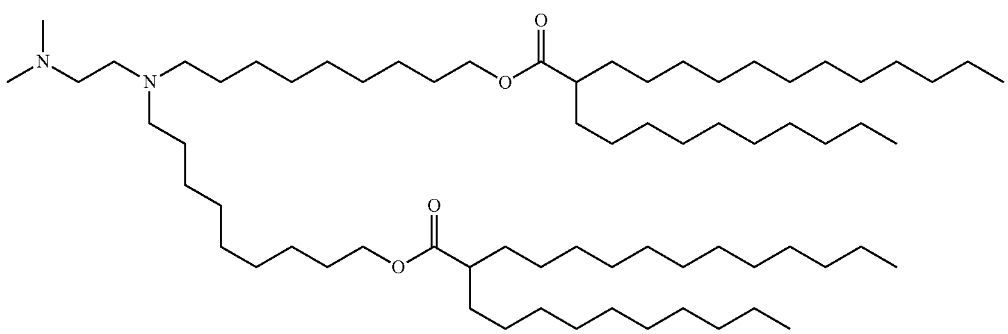 [SMILES: CCCCCCCCCCCCC(CCCCCCCCCC)C(=O)OCCCCCCCCCN(CCCCCCCCCOC(=O)C(CCCCCCCCCC)CCCCCCCCCCCC)CCN(C)C] | B |

It is understood that any embodiment of the compounds of Formula (I), as set forth above, and any specific substituent and/or variable in the compound Formula (I), as set forth above, may be independently combined with other embodiments and/or substituents and/or variables of compounds of Formula (I) to form embodiments of the inventions not specifically set forth above. In addition, in the event that a list of substituents and/or variables is listed for any particular R group, L group or variables a-e in a particular embodiment and/or claim, it is understood that each individual substituent and/or variable may be deleted from the particular embodiment and/or claim and that the remaining list of substituents and/or variables will be considered to be within the scope of the invention.

It is understood that in the present description, combinations of substituents and/or variables of the depicted formulae are permissible only if such contributions result in stable compounds.

In various embodiments, it is understood that the following compounds are not included within the scope of the invention:

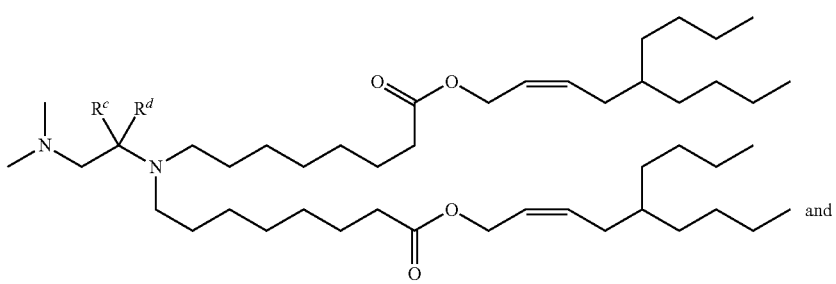

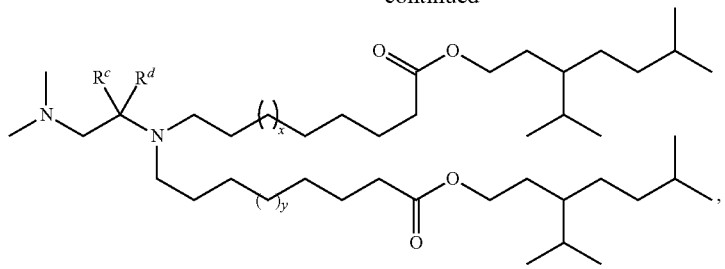

wherein each $R^c$ and $R^d$ are H or $R^c$ and $R^d$ join to form oxo, and x and y are each independently an integer from 0 to 6.

Also provided in various embodiments are pegylated lipids. For example in an embodiment, the pegylated lipid has the following structure (II):

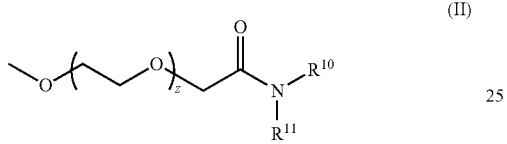

(II)

or a pharmaceutically acceptable salt, tautomer or stereoisomer thereof, wherein:

$R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has mean value ranging from 30 to 60.

In some of the foregoing embodiments of the pegylated lipid (II), $R^{10}$ and $R^{11}$ are not both n-octadecyl when z is 42. In some embodiments, $R^{10}$ and $R^{11}$ are each independently a straight or branched, saturated or unsaturated alkyl chain containing from 10 to 18 carbon atoms. In some embodiments, $R^{10}$ and $R^{11}$ are each independently a straight or branched, saturated or unsaturated alkyl chain containing from 12 to 16 carbon atoms. In some embodiments, $R^{10}$ and $R^{11}$ are each independently a straight or branched, saturated or unsaturated alkyl chain containing 12 carbon atoms. In some embodiments, $R^{10}$ and $R^{11}$ are each independently a straight or branched, saturated or unsaturated alkyl chain containing 14 carbon atoms. In other embodiments, $R^{10}$ and $R^{11}$ are each independently a straight or branched, saturated or unsaturated alkyl chain containing 16 carbon atoms. In still more embodiments, $R^{10}$ and $R^{11}$ are each independently a straight or branched, saturated or unsaturated alkyl chain containing 18 carbon atoms. In still other embodiments, $R^{10}$ is a straight or branched, saturated or unsaturated alkyl chain containing 12 carbon atoms and $R^{11}$ is a straight or branched, saturated or unsaturated alkyl chain containing 14 carbon atoms.

In various embodiments, z spans a range that is selected such that the PEG portion of (II) has an average molecular weight of about 400 to about 6000 g/mol. In some embodiments, the average z is about 45.

In other embodiments, the pegylated lipid has one of the following structures:

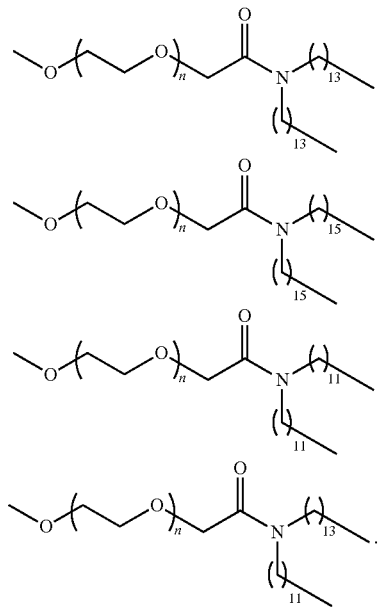

wherein n spans a range such that the average molecular weight of the pegylated lipid is about 2500 g/mol.

Compositions comprising (II) and a cationic lipid are also provided. The cationic lipid may be selected from any cationic lipid. In various embodiments, the cationic lipid is a compound having structure (I) as described above, including any of the substructures and specific compounds in Table 1.

In some embodiments, compositions comprising any one or more of the compounds of Formula (I) are provided. For example, in some embodiments, the compositions comprise any of the compounds of Formula (I) and a therapeutic agent and one or more excipient selected from neutral lipids, steroids and pegylated lipids. Other pharmaceutically acceptable excipients and/or carriers are also included in various embodiments of the compositions.

In certain embodiments, the therapeutic agent comprises a nucleic acid, for example an antisense oligonucleotide or messenger RNA. In some embodiments, the neutral lipid is selected from DSPC, DPPC, DMPC, DOPC, POPC, DOPE and SM. In various embodiments, the molar ratio of the compound to the neutral lipid ranges from about 2:1 to about 8:1.

In various embodiments, the compositions further comprise a steroid or steroid analogue. In certain embodiments, the steroid or steroid analogue is cholesterol. In some of these embodiments, the molar ratio of the compound to cholesterol ranges from about 2:1 to 1:1.

In various embodiments, the composition comprises a pegylated lipid. For example, some embodiments include PEG-DMG. In various embodiments, the molar ratio of the compound to the pegylated lipid ranges from about 100:1 to about 25:1.

In some embodiments, the composition comprises a pegylated lipid having the following structure (II):

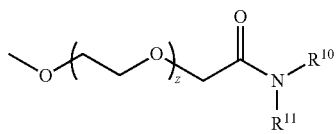

(II)

or a pharmaceutically acceptable salt, tautomer or stereoisomer thereof, wherein:

$R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has a mean value ranging from 30 to 60.

In some embodiments, $R^{10}$ and $R^{11}$ are each independently straight, saturated alkyl chains containing from 12 to 16 carbon atoms. In other embodiments, the average z is about 45.

In some embodiments of the foregoing composition, the therapeutic agent comprises a nucleic acid. For example, in some embodiments, the nucleic acid is selected from antisense, plasmid DNA and messenger RNA.

For the purposes of administration, the compounds of the present invention (typically in the form of lipid nanoparticles in combination with a therapeutic agent) may be administered as a raw chemical or may be formulated as pharmaceutical compositions. Pharmaceutical compositions of the present invention comprise a compound of Formula (I) and one or more pharmaceutically acceptable carrier, diluent or excipient. The compound of Formula (I) is present in the composition in an amount which is effective to form a lipid nanoparticle and deliver the therapeutic agent, e.g., for treating a particular disease or condition of interest. Appropriate concentrations and dosages can be readily determined by one skilled in the art.

Administration of the compositions of the invention can be carried out via any of the accepted modes of administration of agents for serving similar utilities. The pharmaceutical compositions of the invention may be formulated into preparations in solid, semi-solid, liquid or gaseous forms, such as tablets, capsules, powders, granules, ointments, solutions, suspensions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intradermal, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose; agents to act as cryoprotectants such as sucrose or trehalose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, or a protein.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining the lipid nanoparticles of the invention with sterile, distilled water or other carrier so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compositions of the invention, or their pharmaceutically acceptable salts, are administered in a therapeutically effective amount, which will vary depending upon a variety of factors including the activity of the specific therapeutic agent employed; the metabolic stability and length of action of the therapeutic agent; the age, body weight, general health, sex, and diet of the patient; the mode and time of administration; the rate of excretion; the drug combination; the severity of the particular disorder or condition; and the subject undergoing therapy.

Compositions of the invention may also be administered simultaneously with, prior to, or after administration of one or more other therapeutic agents. Such combination therapy includes administration of a single pharmaceutical dosage formulation of a composition of the invention and one or more additional active agents, as well as administration of the composition of the invention and each active agent in its own separate pharmaceutical dosage formulation. For example, a composition of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation methods for the above compounds and compositions are described herein below and/or known in the art.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following Reaction Scheme illustrates methods to make compounds of this invention, i.e., compounds of formula (I):

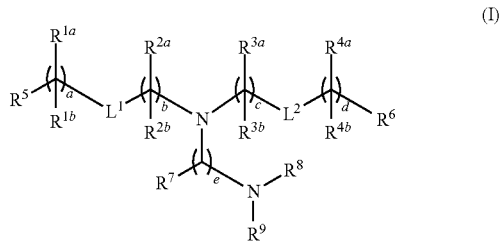

wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^7$, $R^8$, $R^9$, a, b, c, d and e are as defined herein. It is understood that one skilled in the art may be able to make these compounds by similar methods or by combining other methods known to one skilled in the art. It is also understood that one skilled in the art would be able to make, in a similar manner as described below, other compounds of Formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

GENERAL REACTION SCHEME 1

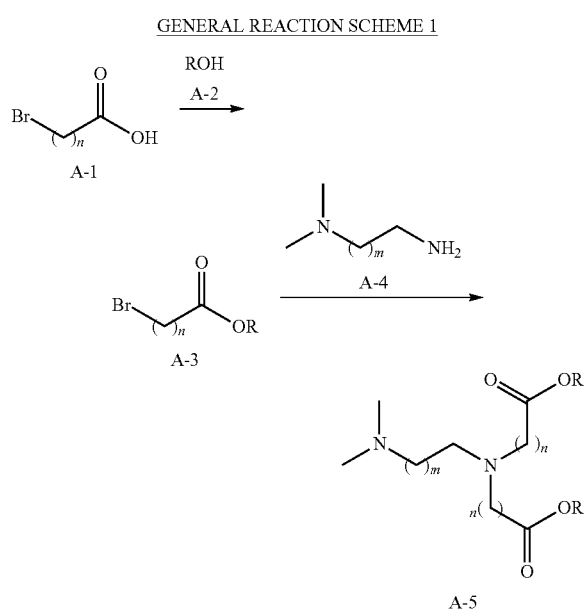

Embodiments of the compound of structure (I) (e.g., compound A-5) can be prepared according to General Reaction Scheme 1 ("Method A"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 1, compounds of structure A-1 can be purchased from commercial sources or prepared according to methods familiar to one of ordinary skill in the art. A mixture of A-1, A-2 and DMAP is treated with DCC to give the bromide A-3. A mixture of the bromide A-3, a base (e.g., N,N-diisopropylethylamine) and the N,N-dimethyldiamine A-4 is heated at a temperature and time sufficient to produce A-5 after any necessarily workup and or purification step.

GENERAL REACTION SCHEME 2

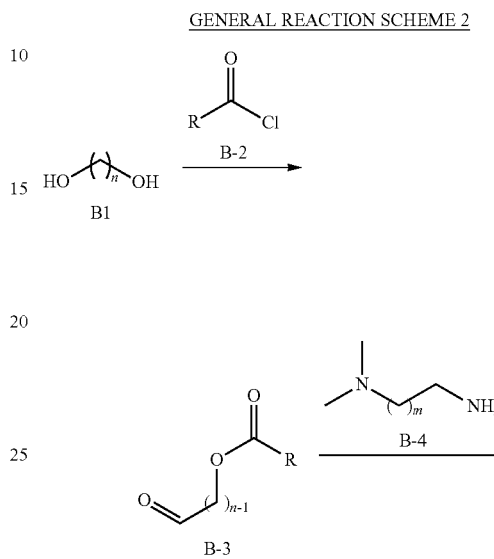

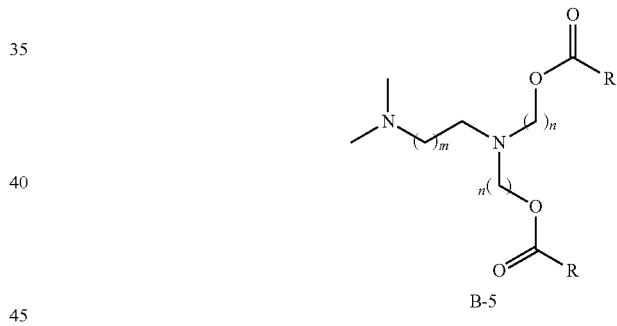

Embodiments of the compound of structure (I) (e.g., compound B-5) can be prepared according to General Reaction Scheme 2 ("Method B"), wherein R is a saturated or unsaturated $C_1$-$C_{24}$ alkyl or saturated or unsaturated cycloalkyl, m is 0 or 1 and n is an integer from 1 to 24. As shown in General Reaction Scheme 2, compounds of structure B-1 can be purchased from commercial sources or prepared according to methods familiar to one of ordinary skill in the art. A solution of B-1 (1 equivalent) is treated with acid chloride B-2 (1 equivalent) and a base (e.g., triethylamine). The crude product is treated with an oxidizing agent (e.g., pyridinum chlorochromate) and intermediate product B-3 is recovered. A solution of crude B-3, an acid (e.g., acetic acid), and N,N-dimethylaminoamine B-4 is then treated with a reducing agent (e.g., sodium triacetoxyborohydride) to obtain B-5 after any necessary work up and/or purification.

It should be noted that although starting materials A-1 and B-1 are depicted above as including only saturated methylene carbons, starting materials which include carbon-carbon double bonds may also be employed for preparation of compounds which include carbon-carbon double bonds.

GENERAL REACTION SCHEME 3

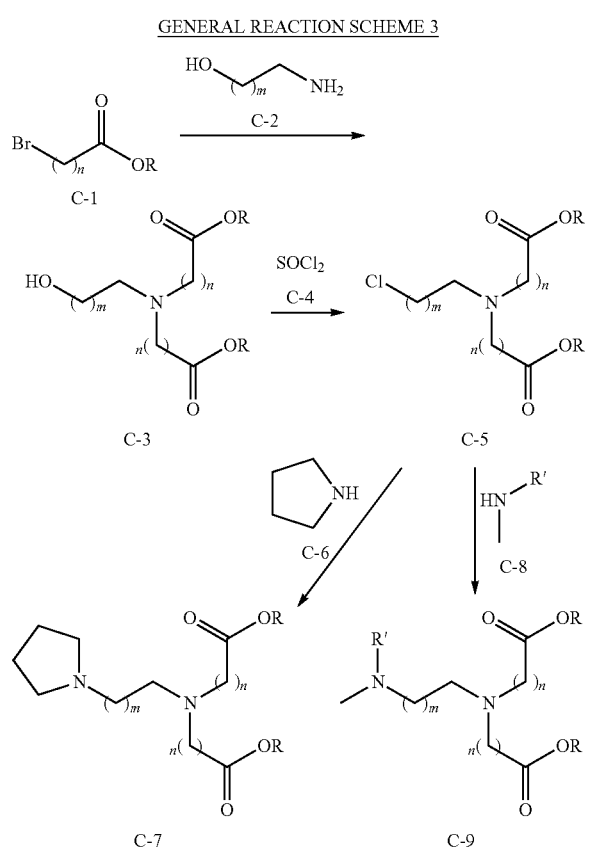

Embodiments of the compound of structure (I) (e.g., compound C-7 or C9) can be prepared according to General Reaction Scheme 3 ("Method C"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 3, compounds of structure C-1 can be purchased from commercial sources or prepared according to methods familiar to one of ordinary skill in the art.

The following examples are provided for purpose of illustration and not limitation.

EXAMPLE 1

Synthesis of Compound 1

Compound 1 was prepared according to method B as follows:

A solution of octan-1,8-diol (9.8 g) in methylene chloride (100 mL) and tetrahydrofuran (60 mL) was treated with 2-ethylhexanoyl chloride (10 g). Triethylamine (15 mL) was slowly added and the solution stirred for three days. The reaction mixture was filtered and the filtrate washed with brine (2x). The organic fraction was dried over anhydrous magnesium sulfate, filtered and the solvent removed. The crude product was filtered through silica gel (20 g) using methylene chloride, yielding 15.8 g of crude product. The resultant oil was dissolved in methylene chloride (100 mL) and treated with pyridinum chlorochromate (13 g) for two hours. Diethyl ether (400 mL) as added and the supernatant filtered through a silica gel bed. The solvent was removed from the filtrate and resultant oil passed down a silica gel (77 g) column using a ethyl acetate/hexane (0-6%) gradient. 8-O-(2'-ethylhexanoyloxy)octanal (6.7 g) was recovered as an oil.

A solution of 8-O-(2'-ethylhexanoyloxy)octanal (6.7 g), acetic acid (25 drops) and 2-N,N-dimethylaminoethylamine (0.54 g) in methylene chloride (40 mL) was treated with sodium triacetoxyborohydride (1.5 g) overnight. The solution was washed with aqueous sodium hydrogen carbonate, followed by brine. The organic phase was dried over anhydrous magnesium sulfate, filtered and the solvent removed. The residue was passed down a silica gel (75 g) column using a methanol/methylene chloride (0-10%) gradient, followed by a second column (20 g), to yield compound 1 (1 g) as a colorless oil.

EXAMPLE 2

Synthesis of Compound 2

Compound 2 was prepared according to method A as follows:

Under an argon atmosphere, to a round-bottom flask charged with phytol (593 mg, 2 mmol), 6-bromohexanoic acid (780 mg, 4 mmol) and 4-(dimethylamino)pyridine (60 mg) in dichloromethane (20 mL) was added dicyclohexylcarbodiimide (908 mg, 4.4 mmol). The precipitate was discarded by filtration. The filtrate was concentrated and the resulting residue was purified by column chromatography on silica gel eluted with a gradient mixture (0% to 3%) of ethyl acetate in hexanes. This gave a colorless oil (0.79 g 1.67 mmol, 83%) of (E)-3,7,11,15-tetramethylhexadec-2-enyl 6-bromohexanoate.

A solution of (E)-3,7,11,15-tetramethylhexadec-2-enyl 6-bromohexanoate (0.42 g, 0.887 mmol), N,N-diisopropylethylamine (1.5 mol eq., 1.33 mmol, MW 129.25, 171 mg) and N,N-dimethylethylenediamine (39 mg, 0.44 mmol) in DMF (4 mL) was heated at 77 C for 18 h. The reaction mixture was then cooled and extracted with hexanes (3×20 mL). The hexane extracts were combined, dried over sodium sulfate, filtered and concentrated. This is combined with $2^{nd}$ reaction (total about 0.7 g). The crude was purified several times by column chromatography on silica gel eluted with a gradient mixture (0% to 5%) of methanol in DCM. This gave a slightly yellow oil (39 mg) of the desired product. $^1$HNMR (400 MHz, $CDCl_3$) δ: 5.33 (m, 2H), 4.59 (m, 4H), 2.85-2.25 (m, 18H).

EXAMPLE 3

Synthesis of Compound 3

Compound 3 was prepared in a manner analogous to compound 2 starting from bromoacetic acid, rather than 6-bromohexanoic acid, to yield 22 mg of thick colorless oil, 0.029 mmol, 6%. 1HNMR (400 MHz, CDCl3) δ: 5.32 (m, 2H), 4.62 (m, 4H), 3.62 (s, 2H), 3.60 (s, 2H), 3.28-2.33 (m, 10H), 2.09-2.00 (m, 4H), 1.76 (s, 3H), 1.70 (s, 3H), 1.60-1.47 (m, 6H), 1.47-0.97 (32H), 0.89-0.84 (m, 24H).

EXAMPLE 4

Synthesis of Compound 4

Compound 4 was prepared according to method B as follows:

A solution of dodecan-1,12-diol (10 g) in methylene chloride (100 mL) and tetrahydrofuran (50 mL) was treated with 2-ethylhexanoic acid (7.2 g), DCC (10.5 g), DMAP (3.5 g) and triethylamine (10 mL). The solution was stirred for four days. The reaction mixture was filtered and the filtrate washed with dilute hydrochloric acid. The organic fraction was dried over anhydrous magnesium sulfate, filtered and the solvent removed. The residue was dissolved in methylene chloride (50 mL), allowed to stand overnight, and filtered. The solvent was removed to yield 12.1 g crude product.

The crude product dissolved in methylene chloride (100 mL) and treated with pyridinum chlorochromate (8 g) overnight. Diethyl ether (400 mL) as added and the supernatant filtered through a silica gel bed. The solvent was removed from the filtrate and resultant oil passed down a silica gel (75 g) column using a ethyl acetate/hexane (0-6%) gradient. Crude 12-O-(2'-ethylhexanoyloxy)dodecanal (3.5 g) was recovered as an oil.

A solution of the crude product (3.5 g), acetic acid (60 drops) and 2-N,N-dimethylaminoethylamine (0.30 g) in methylene chloride (20 mL) was treated with sodium triacetoxyborohydride (0.86 g) overnight. The solution was washed with aqueous sodium hydrogen carbonate, followed by brine. The organic phase was dried over anhydrous magnesium sulfate, filtered and the solvent removed. The residue was passed down a silica gel (20 g) column using a methanol/methylene chloride (0-8%) gradient, followed by a second column (20 g), to yield the desired product as a (0.6 g) as a colorless oil.

EXAMPLE 5

Synthesis of Compound 5

Compound 5 was prepared according to method B as follows:

A solution of hexan-1,6-diol (10 g) in methylene chloride (40 mL) and tetrahydrofuran (20 mL) was treated with 2-hexyldecanoyl chloride (10 g) and triethylamine (10 mL). The solution was stirred for an hour and the solvent removed. The reaction mixture was suspended in hexane, filtered and the filtrate washed with water. The solvent was removed and the residue passed down a silica gel (50 g) column using hexane, followed by methylene chloride, as the eluent, yielding 6-(2'-hexyldecanoyloxy)hexan-1-ol as an oil (7.4 g).

The purified product (7.4 g) was dissolved in methylene chloride (50 mL) and treated with pyridinum chlorochromate (5.2 g) for two hours. Diethyl ether (200 mL) as added and the supernatant filtered through a silica gel bed. The solvent was removed from the filtrate and resultant oil passed down a silica gel (50 g) column using a ethyl acetate/hexane (0-5%) gradient. 6-(2'-hexyldecanoyloxy)dodecanal (5.4 g) was recovered as an oil.

A solution of the product (4.9 g), acetic acid (0.33 g) and 2-N,N-dimethylaminoethylamine (0.40 g) in methylene chloride (20 mL) was treated with sodium triacetoxyborohydride (2.1 g) for two hours. The solution was washed with aqueous sodium hydroxide. The organic phase was dried over anhydrous magnesium sulfate, filtered and the solvent removed. The residue was passed down a silica gel (50 g) column using a methanol/methylene chloride (0-8%) gradient to yield the desired product (1.4 g) as a colorless oil.

EXAMPLE 6

Synthesis of Compound 6

Compound 6 was prepared according to method B as follows: A solution of nonan-1,9-diol (12.6 g) in methylene chloride (80 mL) was treated with 2-hexyldecanoic acid (10.0 g), DCC (8.7 g) and DMAP (5.7 g). The solution was stirred for two hours. The reaction mixture was filtered and the solvent removed. The residue was dissolved in warmed hexane (250 mL) and allowed to crystallize. The solution was filtered and the solvent removed. The residue was dissolved in methylene chloride and washed with dilute hydrochloric acid. The organic fraction was dried over anhydrous magnesium sulfate, filtered and the solvent removed. The residue was passed down a silica gel column (75 g) using 0-12% ethyl acetate/hexane as the eluent, yielding 9-(2'-hexyldecanoyloxy)nonan-1-ol (9.5 g) as an oil.

The product was dissolved in methylene chloride (60 mL) and treated with pyridinum chlorochromate (6.4 g) for two hours. Diethyl ether (200 mL) as added and the supernatant filtered through a silica gel bed. The solvent was removed from the filtrate and resultant oil passed down a silica gel (75 g) column using a ethyl acetate/hexane (0-12%) gradient, yielding 9-(2'-ethylhexanoyloxy)nonanal (6.1 g) as an oil.

A solution of the crude product (6.1 g), acetic acid (0.34 g) and 2-N,N-dimethylaminoethylamine (0.46 g) in methylene chloride (20 mL) was treated with sodium triacetoxyborohydride (2.9 g) for two hours. The solution was diluted with methylene chloride washed with aqueous sodium hydroxide, followed by water. The organic phase was dried over anhydrous magnesium sulfate, filtered and the solvent removed. The residue was passed down a silica gel (75 g) column using a methanol/methylene chloride (0-8%) gradient, followed by a second column (20 g) using a methylene chloride/acetic acid/methanol gradient. The purified fractions were dissolved in methylene chloride, washed with dilute aqueous sodium hydroxide solution, dried over anhydrous magnesium sulfate, filtered and the solvent removed, to yield the desired product (1.6 g) as a colorless oil.

EXAMPLE 7

Synthesis of Compound 7

Compound 7 was prepared from 3,5,5-trimethylhexyl 10-bromodecanoate and N,N-dimethylethane-1,2-diamine according to method A to yield 144 mg of slightly yellow oil, 0.21 mmol, 11%). 1HNMR (400 MHz, CDCl3) δ: 4.09 (t-like, 6.6 Hz, 4H), 2.58-2.51 (m, 2H), 2.44-2.34 (m, 6H), 2.29 (t-like, 7.5 Hz, 4H), 2.25 (s, 6H), 1.67-1.57 (m, 8H), 1.52-1.39 (m, 6H), 1.36-1.21 (m, 24H), 0.95 (d, 6.6 Hz, 6H), 0.90 (s, 18H).

EXAMPLE 8

Synthesis of Compound 8

Compound 8 was prepared by method A in 15% yield. $^1$HNMR (400 MHz, CDCl3) δ: 5.11-5.04 (m, 2H), 2.60-2.54 (m, 2H), 2.47-2.36 (m, 6H), 2.27 (t-like, 7.4 Hz, 4H), 2.25 (s, 6H), 1.66-1.40 (m, 16H), 1.34-1.23 (m, 24H), 0.91 (d, 6.5 Hz, 24H).

EXAMPLE 9

Synthesis of Compound 9

Compound 9 was prepared according to method B as follows:

A solution of nonan-1,9-diol (10.0 g) in methylene chloride (100 mL) was treated with citroneloyl chloride (10.1 g, prepared from citronelic acid and oxalyl chloride) and triethylamine (10 mL), and stirred for three days. The reaction mixture was diluted with methylene chloride and washed with dilute hydrochloric acid. The organic fraction was dried over anhydrous magnesium sulfate, filtered and the solvent removed. The residue was taken up in hexane, filtered and the solvent removed. The residue was passed down a series of silica gel columns (60-70 g) using hexane followed by methylene chloride as the eluent, yielding 9-(citroneloyloxy)nonan-1-ol (7.6 g) as an oil.

The product was dissolved in methylene chloride (50 mL) and treated with pyridinum chlorochromate (6.4 g) for 90 minutes. Diethyl ether (200 mL) as added and the supernatant filtered through a silica gel bed. The residue was dissolved in hexane and passed through a silica gel (20 g) column using hexane as the eluent, yielding 9-(citroneloyloxy)nonanal (5 g) as an oil.

A solution of the crude product (5 g), acetic acid (0.33 g) and 2-N,N-dimethylaminoethylamine (0.48 g) in methylene chloride (40 mL) was treated with sodium triacetoxyborohydride (1.2 g) overnight. The solution was diluted with methylene chloride and washed with aqueous sodium hydroxide. The organic phase was dried over anhydrous magnesium sulfate, filtered and the solvent removed. The residue was passed down a silica gel (50 g) column using a 0-12% methanol/methylene chloride gradient, followed by a second silica gel column (20 g) using the same gradient, to yield the desired product (0.6 g) as a colorless oil.

EXAMPLE 10

Synthesis of Compound 10

Compound 10 was prepared according to method A to yield 147 mg of colorless oil, 0.23 mmol, 17%. $^1$HNMR (400 MHz, CDCl3) δ: 4.11 (t, 6.9 Hz, 4H), 2.56-2.52 (m, 2H), 2.44-2.35 (m, 6H), 2.29 (t-like, 7.5 Hz, 4H), 2.24 (s, 6H), 1.75-1.66 (m, 8H), 1.66-1.57 (m, 4H), 1.52 (q-like, 6.9 Hz, 4H), 1.46-1.38 (m, 4H), 1.38-1.13 (m, 30H), 0.98-0.87 (m, 4H).

EXAMPLE 11

Synthesis of Compound 11

Compound 11 was prepared according to method A to yield 154 mg of slightly yellow oil, 0.22 mmol, 14%). $^1$HNMR (400 MHz, CDCl3) δ: 4.88 (quintet, 6.2 Hz, 2H), 3.20-2.40 (m, 8H), 2.39 (s, 6H), 2.29 (t, 7.5 Hz, 4H), 1.67-1.56 (m, 4H), 1.56-1.48 (m, 8H), 1.38-1.21 (m, 44H), 0.92-0.86 (m, 12H).

EXAMPLE 12

Synthesis of Compound 12

Compound 12 was prepared according to method A to yield 169 mg of slightly yellow oil, 0.26 mmol, 17%). $^1$HNMR (400 MHz, CDCl3) δ: 4.03-3.95 (ABX pattern, 4H), 2.54 (m, 2H), 2.44-2.35 (m, 6H), 2.30 (t-like, 7.5 Hz, 4H), 2.25 (s, 6H), 1.66-1.54 (m, 6H), 1.47-1.23 (m, 40H), 0.92-0.88 (m, 12H).

EXAMPLE 13

Synthesis of Compound 13

Compound 13 was prepared according to method A to yield 152 mg of white paste, 0.23 mmol, 16%. $^1$HNMR (400 MHz, CDCl3) δ: 4.03 (t, 6.7 Hz, 4H), 3.10-2.41 (very broad, 8H), 2.34 (s, 6H), 2.30 (t, 7.5 Hz, 4H), 1.66-1.46 (m, 12H), 1.39-1.21 (m, 40H), 0.89 (t-like, 6.9 Hz, 6H).

EXAMPLE 14

Synthesis of Compound 14

Compound 14 was prepared according to method A to yield 111 mg of colorless oil, 0.16 mmol, 11%. $^1$HNMR (400 MHz, CDCl3) δ: 5.09 (m, 2H), 4.16-4.05 (m, 4H), 3.10-2.40 (very broad, 8H), 2.31 (s, 6H), 2.29 (t, 7.5 Hz, 4H), 2.06-1.89 (m, 4H), 1.69 (d, 0.8 Hz, 6H), 1.61 (s, 6H), 1.73-1.13 (m, 50H), 0.92 (d, 6.6 Hz, 6H).

EXAMPLE 15

Synthesis of Compound 15

Compound 15 was prepared according to method A to yield 116 mg of white paste, 0.16 mmol, 10%. $^1$HNMR (400 MHz, CDCl3) δ: 4.06 (t, 6.7 Hz, 4H), 2.62-2.51 (broad, 2H), 2.48-2.33 (br., 6H), 2.29 (t, 7.5 Hz, 4H), 2.25 (s, 6H), 1.69 (quintet, 7.0 Hz, 8H), 1.48-1.38 (br., 4H), 1.38-1.21 (m, 52H), 0.89 (t-like, 6.8 Hz, 6H).

EXAMPLE 16

Synthesis of Compound 16

Compound 16 was prepared according to method A to yield 118 mg of colorless oil 0.17 mmol, 12%. $^1$HNMR (400 MHz, CDCl3) δ: 4.06 (t, 6.8 Hz, 4H), 2.57-2.52 (m, 2H), 2.44-2.34 (m, 6H), 2.29 (t, 7.6 Hz, 4H), 2.25 (s, 6H), 1.62 (quintet-like, 7.0 Hz, 8H), 1.47-1.39 (m, 4H), 1.37-1.22 (m, 44H), 0.89 (t-like, 6.8 Hz, 6H).

EXAMPLE 17

Synthesis of Compound 17

Compound 17 was prepared according to method A to yield 145 mg of slightly yellow oil, 0.21 mmol, 13%. 1HNMR (400 MHz, CDCl3) δ: 5.01 (m, 0.27H from cis-isomer), 4.63 (tt, 11.2 Hz, 4.5 Hz, 1.73H from trans-isomer), 2.61-2.24 (18H), 2.01 (m, 4H), 1.81 (m, 4H), 1.61 (quintet-like, 7.2 Hz, 4H), 1.44 (m, 4H), 1.36-1.21 (24H), 1.11 (m, 4H), 1.01 (m, 2H), 0.87 (s, 2.7H from cis-isomer), 0.86 (s, 15.3H from trans-isomer).

EXAMPLE 18

Synthesis of Compound 18

Compound 18 was prepared according to method A to yield 111 mg of colorless oil, 0.17 mmol, 14%. $^1$HNMR (400 MHz, CDCl3) δ: 4.88 (quintet, 6.2 Hz, 2H), 2.61-2.51 (br., 2H), 2.48-2.34 (br, 6H), 2.29 (t, 7.6 Hz, 4H), 2.25 (s, 6H), 1.62 (quintet-like, 7.3 Hz, 4H), 1.55-1.48 (m, 8H), 1.47-1.39 (m, 4H), 1.37-1.21 (m, 32H), 0.91-0.86 (m, 12H).

EXAMPLE 19

Synthesis of Compound 19

Compound 19 was prepared according to method A to yield 76 mg of colorless oil, 0.11 mmol, 6%. $^1$HNMR (400

MHz, CDCl3) δ: 5.77 (dt-like, 14.4 Hz, 6.6 Hz, 2H), 5.55 (dtt-like, 14.4 Hz, 6.5 Hz, 1.4 Hz, 2H), 4.51 (dd, 6.6 Hz, 0.6 Hz, 4H), 2.61-2.50 (br., 2H), 2.50-2.34 (br. 6H), 2.30 (t, 7.5 Hz, 4H), 2.25 (s, 6H), 2.04 (q, 7.1 Hz, 4H), 1.62 (quintet, 7.3 Hz, 4H), 1.48-1.21 (40H), 0.88 (t-like, 6.8 Hz, 6H).

EXAMPLE 20

Synthesis of Compound 20

Compound 20 was prepared according to the general procedure A to yield 157 mg of colorless oil, 0.22 mmol, 14%. $^1$HNMR (400 MHz, CDCl3) δ: 3.97 (d, 5.8 Hz, 4H), 2.57-2.51 (m, 2H), 2.44-2.33 (m, 6H), 2.30 (t, 7.5 Hz, 4H), 2.24 (s, 6H), 1.63 (quintet-like, 7.3 Hz, 6H), 1.43 (quintet-like, 7.3 Hz, 4H), 1.36-1.21 (44H), 0.93-0.86 (m, 12H).

EXAMPLE 21

Synthesis of Compound 21

Compound 21 was prepared according to the general procedure A to yield 164 mg of colorless oil, 0.21 mmol, 14%. $^1$HNMR (400 MHz, CDCl3) δ: 3.97 (d, 5.8 Hz, 4H), 2.57-2.51 (m, 2H), 2.44-2.34 (m, 6H), 2.30 (t, 7.5 Hz, 4H), 2.24 (s, 6H), 1.62 (quintet-like, 7.3 Hz, 6H), 1.43 (quintet-like, 7.3 Hz, 4H), 1.36-1.21 (52H), 0.93-0.86 (m, 12H).

EXAMPLE 22

Synthesis of Compound 22

Compound 22 was prepared according to method A as follows:
Step 1.
To a solution of 6-bromohexanoic acid (20 mmol, 3.901 g), 2-hexyl-1-decanol (1.8 eq, 36 mmol, 8.72 g) and 4-dimethylaminopyridine (DMAP 0.5 eq, 10 mmol, 1.22 g) in DCM (80 mL) was added DCC (1.1 eq, 22 mmol, 4.54 g). The resulting mixture was stirred at RT for 16 h. The precipitate was discarded by filtration. The filtrate was concentrated. The residue was purified by column chromatography on silica gel eluted with a gradient mixture of ethyl acetate in hexanes (0 to 2%). This gave the desired product as a colorless oil (7.88 g, 18.8 mmol, 94%)
Step 2.
A mixture of the bromide from step 1 (1.34 equiv., 7.88 g, 18.8 mmol), N,N-diisopropylethylamine (1.96 equiv., 27.48 mmol, 4.78 mL) and N,N-dimethylethylenediamine (1 equiv., 14.02 mmol, 1.236 g, 1.531 mL) in acetonitrile (70 mL) in 250 mL flask equipped with a condenser was heated at 79 C (oil bath) for 16 h. The reaction mixture was cooled to RT and concentrate. The residue was taken in a mixture of ethyl acetate and hexanes (1:9) and water. The phases were separated, washed with water (100 mL) and brine. Dried over sodium sulfate and concentrated (8.7 g oil). The crude (8.7 g oil) was purified by column chromatography on silica gel (0 to 3% MeOH in chloroform). The fractions containing the desired product were combined and concentrated. The residue was dissolved in 1 mL of hexane and filtered through a layer of silica gel (3-4 mm, washed with 8 mL of hexane). The filtrate was blown to dry with a stream of Ar and dried well in vacuo overnight (1.30 g, mmol, %, colorless oil, desired product). $^1$HNMR (400 MHz, CDCl3) δ: 3.96 (d, 5.8 Hz, 4H), 2.55-2.50 (m, 2H), 2.43-2.39 (m, 4H), 3.37-3.32 (m, 2H), 2.30 (t, 7.5 Hz, 4H), 2.23 (s, 6H), 1.63 (quintet-like, 7.6 Hz, 6H), 1.48-1.40 (m, 4H), 1.34-1.20 (52H), 0.88 (t-like, 6.8 Hz, 12H).

EXAMPLE 23

Synthesis of Compound 23

Compound 23 was prepared according to the general procedure A to yield 200 mg of colorless oil, 0.24 mmol, 16%. $^1$HNMR (400 MHz, CDCl3) δ: 3.97 (d, 5.8 Hz, 4H), 2.57-2.51 (m, 2H), 2.44-2.34 (m, 6H), 2.30 (t, 7.5 Hz, 4H), 2.24 (s, 6H), 1.67-1.58 (m, 6H), 1.43 (quintet-like, 7.3 Hz, 4H), 1.36-1.21 (60H), 0.89 (t-like, 6.8 Hz, 12H).

EXAMPLE 24

Synthesis of Compound 24

Compound 24 was prepared according to the general procedure A to yield 138 mg of colorless oil, 0.18 mmol, 12%. $^1$HNMR (400 MHz, CDCl3) δ: 4.90 (sixlet-liked, 6.3 Hz, 2H), 2.63-2.33 (br. 8H), 2.27 (t, 7.5 Hz, 4H), 2.26 (s, 6H), 1.66-1.57 (m, 4H), 1.51-1.39 (m, 6H), 1.35-1.21 (54H), 1.20 (d, 6.2 Hz, 6H), 0.89 (t-like, 6.8 Hz, 6H).

EXAMPLE 25

Synthesis of Compound 25

Compound 25 was prepared according to the general procedure A to yield 214 mg of colorless oil, 0.24 mmol, 17%. $^1$HNMR (400 MHz, CDCl3) δ: 3.97 (d, 5.8 Hz, 4H), 2.58-2.52 (m, 2H), 2.45-2.35 (m, 6H), 2.30 (t, 7.5 Hz, 4H), 2.25 (s, 6H), 1.62 (quintet-like, 7.0 Hz, 6H), 1.43 (quintet-like, 7.0 Hz, 4H), 1.36-1.21 (68H), 0.89 (t-like, 6.7 Hz, 12H).

EXAMPLE 26

Synthesis of Compound 26

Compound 26 was prepared according to the general procedure A to yield 170 mg of colorless oil, 0.21 mmol, 13%. $^1$HNMR (400 MHz, CDCl3) δ: 5.42-5.29 (m, 8H), 4.05 (t, 6.8 Hz, 4H), 2.77 (t, 6.5 Hz, 4H), 2.55-2.50 (m, 2H), 2.43-2.39 (m, 4H), 2.37-2.32 (m, 2H), 2.29 (t, 7.6 Hz, 4H), 2.23 (s, 6H), 2.05 (q, 6.8 Hz, 8H), 1.63 (quintet-like, 7.5 Hz, 8H), 1.48-1.40 (m, 4H), 1.39-1.23 (36H), 0.90 (t-like, 6.8 Hz, 6H).

EXAMPLE 27

Synthesis of Compound 27

Compound 27 was prepared according to the general procedure A to yield 255 mg of colorless oil, 0.29 mmol, 18%. $^1$HNMR (400 MHz, CDCl3) δ: 3.96 (d, 5.8 Hz, 4H), 2.55-2.50 (m, 2H), 2.43-2.39 (m, 4H), 3.37-3.32 (m, 2H), 2.30 (t, 7.5 Hz, 4H), 2.23 (s, 6H), 1.63 (quintet-like, 7.6 Hz, 6H), 1.48-1.40 (m, 4H), 1.34-1.20 (68H), 0.88 (t-like, 6.8 Hz, 12H).

EXAMPLE 28

Synthesis of Compound 28

Compound 28 was prepared according to the general procedure A to yield 248 mg of colorless oil, 0.27 mmol, 19%. $^1$HNMR (400 MHz, CDCl3) δ: 3.97 (d, 5.8 Hz, 4H), 2.57-2.52 (m, 2H), 2.44-2.34 (m, 6H), 2.30 (t, 7.5 Hz, 4H), 2.24 (s, 6H), 1.67-1.58 (m, 6H), 1.43 (quintet-like, 7.3 Hz, 4H), 1.36-1.21 (76H), 0.89 (t-like, 6.8 Hz, 12H).

EXAMPLE 29

Synthesis of Compound 29

Compound 29 was prepared according to the general procedure A to yield 181 mg of colorless oil, 0.23 mmol, 17%. $^1$HNMR (400 MHz, CDCl3) δ: 4.87 (quintet, 6.3 Hz, 4H), 2.56-2.51 (m, 2H), 2.43-2.34 (m, 6H), 2.27 (t, 7.5 Hz, 4H), 2.24 (s, 6H), 1.61 (quintet-like, 7.3 Hz, 4H), 1.55-1.46 (m, 8H), 1.46-1.37 (m, 4H), 1.36-1.08 (52H), 0.88 (t-like, 6.8 Hz, 12H).

EXAMPLE 30

Synthesis of Compound 30

Compound 30 was prepared according to the general procedure A to yield 88 mg of colorless oil, 0.11 mmol, 3%. $^1$HNMR (400 MHz, CDCl3) δ: 3.97 (d, 5.5 Hz, 4H), 2.58-2.51 (m, 2H), 2.49-2.44 (m, 4H), 2.38-2.30 (m, 6H), 2.24 (s, 6H), 1.75 (quintet-like, 7.3 Hz, 4H), 1.66-1.54 (m, 2H), 1.35-1.06 (64H), 0.89 (t-like, 6.4 Hz, 12H).

EXAMPLE 31

Synthesis of Compound 31

Compound 31 was prepared according to the general procedure C to yield 275 mg of slightly yellow oil, 0.30 mmol, total yield 35% for three steps. $^1$HNMR (400 MHz, CDCl3) δ: 3.97 (d, 5.8 Hz, 4H), 2.63-2.47 (m, 8H), 2.45-2.41 (m, 4H), 2.31 (t, 7.5 Hz, 4H), 1.82-1.74 (m, 4H), 1.64 (quintet-like, 7.6 Hz, 6H), 1.46 (quintet-like, 7.6 Hz, 4H), 1.36-1.18 (68H), 0.89 (t-like, 6.8 Hz, 12H).

EXAMPLE 32

Synthesis of Compound 32

Compound 32 was prepared according to method C as follows:
Step 1.
To a solution of 2-aminoethanol (116 mg, 1.9 mmol, 115 uL, MW 61.08, d 1.012) in 15 ml of anhydrous THF, 2-hexyldecyl 6-bromohexanoate (1.9 eq, 1.52 g, 3.62 mmol), potassium carbonate (1.9 eq, 3.62 mmol, 500 mg), cesium carbonate (0.3 eq, 0.57 mmol, 186 mg,) and sodium iodide (10 mg) were added and was heated to reflux for 6 days under Ar. The solvent was evaporated under reduced pressure and the residue was taken up in hexanes and washed with water and brine. The organic layer was separated, dried over anhydrous sodium sulphate, filtered and evaporated under reduced to obtain a colorless oil. The crude product was purified by flash column chromatography on silica gel (230-400 mesh silica gel, MeOH in chloroform, 0 to 4%) to yield 936 mg of colorless oil (1.27 mmol, 70%).
Step 2.
To a magnetically stirred and ice-cooled solution of 936 mg (1.27 mmol) of the product from step 1 in 2 mL of CHCl3, was added thionyl chloride (2.9 eq, 3.70 mmol, 440 mg, 270 uL,) in 15 mL of chloroform dropwise under an Ar atmosphere. After the completion of addition of SOCl2, the ice bath was removed and the reaction mixture was stirred for 16 h at room temperature under an Ar atmosphere. Removal of CHCl3, and SOCl2 under reduced pressure gave a thick yellow oil.
Step 3.
The crude from step 2 was dissolved in THF (20 mL). To the THF solution was added pyrrolidine (1.6 mL, 1.36 g, 19 mmol). The sealed mixture was heated at 64 C overnight. The reaction mixture was concentrated (dark brown oil). The residue was purified by flash dry column chromatography on silica gel (MeOH in chloroform, 0 to 4%). This gave the desired product as a slightly yellow oil (419 mg, 0.53 mmol, 83%). $^1$HNMR (400 MHz, CDCl3) δ: 3.97 (d, 5.8 Hz, 4H), 2.65-2.47 (m, 8H), 2.45-2.41 (m, 4H), 2.31 (t, 7.5 Hz, 4H), 1.81-1.74 (m, 4H), 1.64 (quintet-like, 7.6 Hz, 6H), 1.46 (quintet-like, 7.6 Hz, 4H), 1.36-1.21 (52H), 0.89 (t-like, 6.8 Hz, 12H).

EXAMPLE 33

Synthesis of Compound 33

Compound 33 was prepared according to the general procedure C to yield 419 mg of slightly yellow oil, 0.54 mmol, total yield 60% for three steps. $^1$HNMR (400 MHz, CDCl3) δ: 3.97 (d, 5.8 Hz, 4H), 2.57-2.53 (m, 2H), 2.46-2.40 (m, 8H), 2.31 (t, 7.5 Hz, 4H), 2.23 (s, 3H), 1.64 (quintet-like, 7.6 Hz, 6H), 1.46 (quintet-like, 7.6 Hz, 4H), 1.36-1.20 (52H), 1.06 (t, 7.2 Hz, 3H), 0.89 (t-like, 6.8 Hz, 12H).

EXAMPLE 34

Synthesis of Compound 34

Compound 34 was prepared according to method B as follows:
A solution of nonan-1,9-diol (10 g) in methylene chloride (250 mL) was treated with 2-ethylhexanoic acid (4.5 g), DCC (7.7 g) and DMAP (4.2 g). The solution was stirred for three days. The reaction mixture was filtered and hexane (200 mL) added to the filtrate. The mixture was stirred and the precipitates allowed to settle out. The supernatant was decanted and the solvent removed. The residue was suspended in hexane (70 mL) and allowed to settle. The supernatant was decanted and the solvent removed. The residue was dissolved in hexane, allowed to stand at room temperature and then filtered. The solvent was removed and the residue passed down a silica gel column (50 g) using a 0-10% ethyl acetate/hexane gradient, followed by a 0-8% methanol/methylene chloride gradient, yielding 5.6 g of 9-(2'ethylhexanoyloxy)nonan-1-ol as a colorless oil.
The product dissolved in methylene chloride (70 mL) and treated with pyridinium chlorochromate (5 g) for two hours. Diethyl ether (250 mL) was added and the supernatant filtered through a silica gel bed. The solvent was removed from the filtrate and resultant oil dissolved in hexane. The suspension was filtered through a silica gel plug and the solvent removed, yielding crude 9-(2'ethylhexanoyloxy) nonanal (3.4 g) as an oil.
A solution of the crude product (3.4 g), acetic acid (0.52 g) and 2-N,N-dimethylaminoethylamine (0.33 g) in methylene chloride (50 mL) was treated with sodium triacetoxyborohydride (1.86 g) overnight. The solution was washed with aqueous sodium hydroxide solution. The organic phase was dried over anhydrous magnesium sulfate, filtered and the solvent removed. The residue was passed down a silica gel (50 g) column using an acetic acid/methanol/methylene chloride (2-0%/0-12%/98-88%) gradient. The purified fractions were washed with aqueous sodium hydrogen carbonate, dried over magnesium sulphate, filtered and the solvent removed, yielding compound 34 as an oil (0.86 g).

EXAMPLE 35

Synthesis of Compound 35

Compound 35 was prepared according to method B as follows:

A solution of dodecan-1,12-diol (18.1 g) in methylene chloride (90 mL) was treated with citronelic acid (7.5 g), DCC (10.0 g) and DMAP (9.5 g). The solution was stirred overnight. The reaction mixture was filtered and the filtrate washed with dilute hydrochloric acid. The organic fraction was dried over anhydrous magnesium sulfate, filtered and the solvent removed to yield 12.2 g of crude 12-citroneloyloxydodecan-1-ol.

The crude product dissolved in methylene chloride (60 mL) and treated with pyridinum chlorochromate (6.8 g) for three hours. Diethyl ether (200 mL) as added and the supernatant filtered through a silica gel bed. The solvent was removed from the filtrate and resultant oil passed down a silica gel (75 g) column using a ethyl acetate/hexane (0-12%) gradient. Crude 12-citroneloyloxydodecanal (6.2 g) was recovered as an oil.

A solution of the crude product (6.2 g), acetic acid (0.44 g) and 2-N,N-dimethylaminoethylamine (0.50 g) in methylene chloride (40 mL) was treated with sodium triacetoxyborohydride (2.9 g) overnight. The solution was washed with aqueous sodium hydrogen carbonate, followed by brine. The organic phase was dried over anhydrous magnesium sulfate, filtered and the solvent removed. The residue was passed down a silica gel (75 g) column using an acetic acid/methanol/methylene chloride (2-0%/0-12%/98-88%) gradient. The purified fractions were washed with aqueous sodium hydrogen carbonate, dried over magnesium sulphate, filtered and the solvent removed, yielding compound 35 (1.68 g) as an oil.

EXAMPLE 36

Synthesis of Compound 36

Compound 36 was prepared according to the general procedure C to yield 108 mg of colorless oil (0.14 mmol). $^1$HNMR (400 MHz, CDCl3) δ: 4.87 (quintet, 6.3 Hz, 2H), 2.56-2.51 (m, 2H), 2.45-2.40 (m, 4H), 2.38-2.33 (m, 2H), 2.29 (t, 7.5 Hz, 4H), 2.24 (s, 6H), 1.64 (quintet-like, 7.7 Hz, 4H), 1.55-1.41 (m, 12H), 1.35-1.18 (m, 52H), 0.89 (t-like, 6.8 Hz, 12H).

EXAMPLE 37

Synthesis of Compound 37

Compound 37 was prepared according to the general procedure C to yield 330 mg of colorless oil (0.40 mmol, total yield 80% for three steps). $^1$HNMR (400 MHz, CDCl3) δ: 4.87 (quintet, 6.5 Hz, 2H), 2.64-2.47 (m, 8H), 2.45-2.40 (m, 4H), 2.29 (t, 7.5 Hz, 4H), 1.81-1.74 (m, 4H), 1.64 (quintet-like, 7.6 Hz, 4H), 1.55-1.41 (m, 12H), 1.35-1.18 (m, 50H), 0.89 (t-like, 6.8 Hz, 12H).

EXAMPLE 38

Synthesis of Compound 38

Compound 38 was prepared according to method B as follows:

A solution of nonan-1,9-diol (16 g) in methylene chloride (100 mL) was treated with 2-butyloctanoic acid (10 g), DCC (10.3 g) and DMAP (6.7 g). The solution was stirred for three days. The reaction mixture was filtered and hexane (250 mL) added to the filtrate. The mixture was stirred and the precipitates allowed to settle out. The supernatant was decanted and the solvent removed. The residue was suspended in hexane and allowed to settle. The supernatant was decanted and the solvent removed (repeated twice). The residue was dissolved in hexane, allowed to stand at room temperature and then filtered. The solvent was removed and the residue passed down a silica gel column (18 g) using methylene chloride, yielding crude 9-(2'-butyloctanoyloxy)nonan-1-ol (17.7 g) as an oil.

The crude product was dissolved in methylene chloride (250 mL) and treated with pyridinium chlorochromate (11.2 g) overnight. Diethyl ether (750 mL) was added and the supernatant filtered through a silica gel bed. The solvent was removed from the filtrate and resultant oil dissolved in hexane (150 mL). The suspension was filtered through a silica gel plug and the solvent removed. The crude product was passed down a silica gel (80 g) column using a 0-6% ethyl acetate/hexane gradient, yielding 9-(2'-butyloctanoyloxy)nonanal (5.3 g) as an oil.

A solution of the product (5.3 g), acetic acid (0.37 g) and 2-N,N-dimethylaminoethylamine (0.47 g) in methylene chloride (50 mL) was treated with sodium triacetoxyborohydride (3.35 g) overnight. The solution was washed with aqueous sodium hydroxide solution. The organic phase was dried over anhydrous magnesium sulfate, filtered and the solvent removed. The residue was passed down a silica gel (60 g) column using an acetic acid/methanol/methylene chloride (2-0%/0-12%/98-88%) gradient. The purified fractions were washed with aqueous sodium hydrogen carbonate, dried over magnesium sulphate, filtered and the solvent removed, yielding compound 38 as an oil (2.3 g).

EXAMPLE 39

Synthesis of Compound 39

Compound 39 was prepared according to method B as follows:

A solution of hexan-1,6-diol (12 g) in methylene chloride (250 mL) was treated with 2-decyltetradecanoic acid (17.5 g), DCC (11.3 g) and DMAP (6.8 g). The solution was stirred for overnight. The reaction mixture was filtered and hexane added to the filtrate. The mixture was stirred and the precipitates allowed to settle out. The supernatant was decanted and the solvent removed. The residue was passed down a silica gel column (80 g) using hexane followed by 0-1% methanol/methylene chloride, yielding crude 6-(2'-decyltetradecanoyloxy)hexan-1-ol (5.8 g) as an oil.

The crude product was dissolved in methylene chloride (70 mL) and treated with pyridinium chlorochromate (2.9 g) for two hours. Diethyl ether (250 mL) was added and the supernatant filtered through a silica gel bed. The solvent was removed from the filtrate and resultant oil dissolved in hexane. The suspension was filtered through a silica gel plug and the solvent removed. The crude product was passed down a silica gel (10 g) column using a 0-5% ethyl acetate/hexane gradient, yielding 6-(2'-decyltetradecanoyloxy)hexanal (3.2 g) as an oil.

A solution of the product (3.2 g), acetic acid (0.28 g) and 2-N,N-dimethylaminoethylamine (0.15 g) in methylene chloride (20 mL) was treated with sodium triacetoxyborohydride (0.98 g) overnight. The solution was washed with aqueous sodium hydroxide solution. The organic phase was dried over anhydrous magnesium sulfate, filtered and the solvent removed. The residue was passed down a silica gel (50 g) column using an acetic acid/methanol/methylene chloride (2-0%/0-12%/98-88%) gradient. The purified fractions were washed with aqueous sodium hydrogen carbonate, dried over magnesium sulphate, filtered and the solvent removed, yielding compound 39 as an oil (1.2 g).

EXAMPLE 40

Synthesis of Compound 40

Compound 40 was prepared according to method B as follows:

A solution of nonan-1,9-diol (10.1 g) in methylene chloride (200 mL) was treated with 2-octyldodecanoic acid (10.0 g), DCC (8.3 g) and DMAP (5.0 g). The solution was stirred for overnight. The reaction mixture was filtered and hexane (200 mL) added to the filtrate. The mixture was stirred and the precipitates allowed to settle out. The supernatant was decanted and the solvent removed. This process was repeated twice. The residue was passed down a silica gel column (75 g) using hexane followed by 4-10% methanol/methylene chloride, yielding crude 9-(2'-octyldodecanoyloxy)nonan-1-ol (~11 g) as an oil.

The crude product was dissolved in methylene chloride (70 mL) and treated with pyridinium chlorochromate (8 g) for two hours. Diethyl ether (400 mL) was added and the supernatant filtered through a silica gel bed. The solvent was removed from the filtrate and resultant oil dissolved in hexane. The suspension was filtered through a silica gel plug and the solvent removed, yielding crude 9-(2'-octyldodecanoyloxy)nonanal (8.4 g) as an oil.

A solution of the product (8.4 g), acetic acid (0.84 g) and 2-N,N-dimethylaminoethylamine (0.55 g) in methylene chloride (60 mL) was treated with sodium triacetoxyborohydride (2.9 g) for two hours. The solution was washed with aqueous sodium hydroxide solution. The organic phase was dried over anhydrous magnesium sulfate, filtered and the solvent removed. The residue was passed down a silica gel (75 g) column using an acetic acid/methanol/methylene chloride (2-0%/0-12%/98-88%) gradient. The purified fractions were washed with aqueous sodium hydrogen carbonate, dried over magnesium sulphate, filtered and the solvent removed, yielding compound 40 as an oil (3.2 g).

EXAMPLE 41

Synthesis of Compound 41

Compound 41 was prepared according to method B as follows:

A solution of nonan-1,9-diol (9.6 g) in methylene chloride (200 mL) was treated with 2-decyltetradecanoic acid (8.4 g), DCC (8.6 g) and DMAP (5.0 g). The solution was stirred for overnight. The reaction mixture was filtered and hexane (200 mL) added to the filtrate. The mixture was stirred and the precipitates allowed to settle out. The supernatant was decanted and the solvent removed. This process was repeated twice. The residue was passed down a silica gel column (75 g) using hexane followed by 4-10% methanol/methylene chloride, yielding crude 9-(2'-decyltetradecanoyloxy)nonan-1-ol (6.4 g) as an oil.

The crude product was dissolved in methylene chloride (50 mL) and treated with pyridinium chlorochromate (5.7 g) for two hours. Diethyl ether (200 mL) was added and the supernatant filtered through a silica gel bed. The solvent was removed from the filtrate and resultant oil dissolved in hexane. The suspension was filtered through a silica gel plug and the solvent removed, yielding crude 9-(2'-decyltetradecanoyloxy)nonanal (5 g) as an oil.

A solution of the product (5 g), acetic acid (0.45 g) and 2-N,N-dimethylaminoethylamine (0.32 g) in methylene chloride (20 mL) was treated with sodium triacetoxyborohydride (1.6 g) for two hours. The solution was washed with aqueous sodium hydroxide solution. The organic phase was dried over anhydrous magnesium sulfate, filtered and the solvent removed. The residue was passed down a silica gel (50 g) column using an acetic acid/methanol/methylene chloride (2-0%/0-12%/98-88%) gradient. The purified fractions were washed with aqueous sodium hydrogen carbonate, dried over magnesium sulphate, filtered and the solvent removed, yielding compound 41 as an oil (2.2 g).

EXAMPLE 42

Synthesis of PEG Lipid

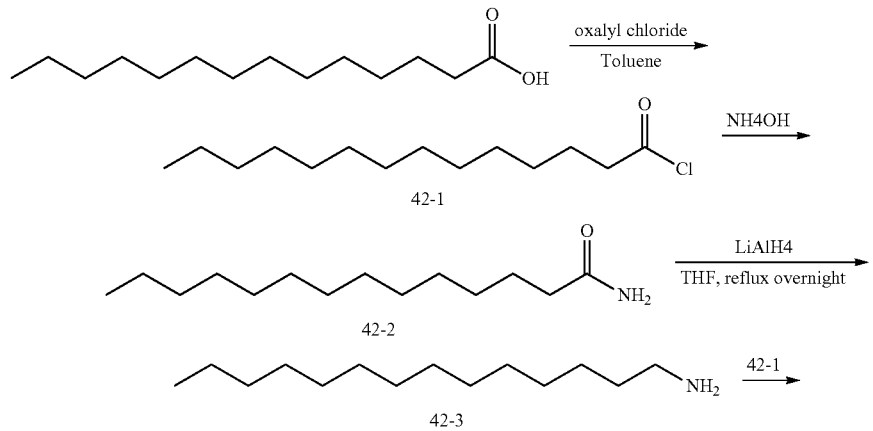

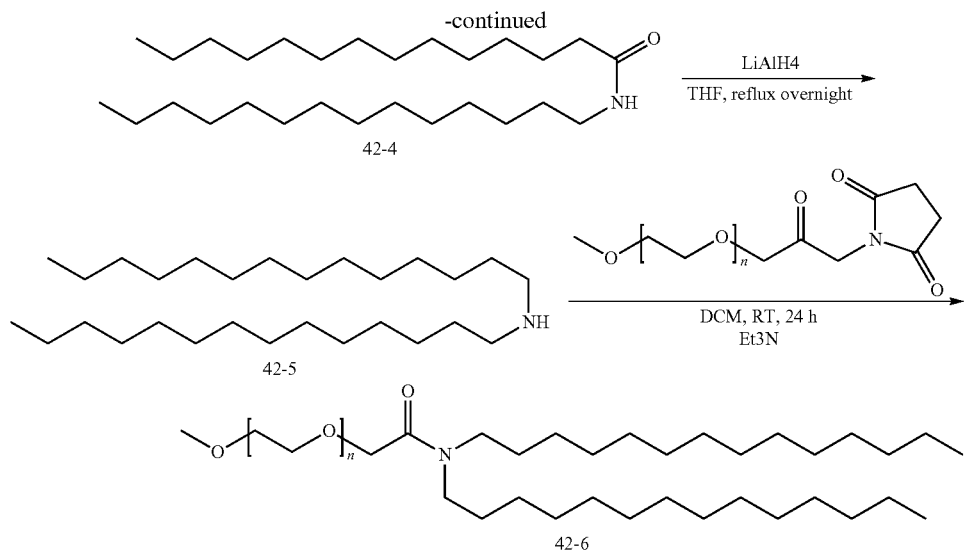

Pegylated lipid 42-6 ("PEG-DMA") was prepared according to the above reaction scheme, wherein n approximates the center of the range of ethylene oxide repeating units in the pegylated lipid.

Synthesis of 42-1 and 42-2

To a solution of myristic acid (6 g, 26 mmol) in toluene (50 mL) was added oxalyl chloride (39 mmol, 1.5 eq. 5 g) at RT. After the resulting mixture was heated at 70° C. for 2 h, the mixture was concentrated. The residue was taken up in toluene and concentrated again. The residual oil was added via a syringe to a concentrated ammonia solution (20 mL) at 10° C. The reaction mixture was filtered and washed with water. The white solid was dried in vacuo. The desired product was obtained as a white solid (3.47 g, 15 mmol, 58.7%).

Synthesis of 42-3

To suspension of 20-2 (3.47 g, 15 mmol) in THF (70 mL) was added in portions lithium aluminium hydride (1.14 g, 30 mmol) at RT during 30 min period of time. Then the mixture was heated to reflux gently (oil bath at 65° C.) overnight. The mixture was cooled to 5 C and sodium sulphate 9 hydrate was added. The mixture was stirred for 2 h, filtered through a layer of celite, washed with 15% of MeOH in DCM (200 mL). The filtrate and washings were combined and concentrated. The residual solid was dried in vacuo. The desired product was obtained as a white solid (2.86 13.4 mmol, 89.5%).

Synthesis of 42-4

To a solution of myristic acid (3.86 g, 16.9 mmol) in benzene (40 mL) and DMF (1 drop) was added oxalyl chloride (25.35 mmol, 1.5 eq. 3.22 g) at RT. The mixture was stirred at RT for 1.5 h. Heated at 60° C. for 30 min. The mixture was concentrated. The residue was taken up in toluene and concentrated again. The residual oil (light yellow) was taken in 20 mL of benzene and added via syringe to a solution of 20-3 (2.86 13.4 mmol) and triethylamine (3.53 mL, 1.5 eq) in benzene (40 mL) at 10° C. After addition, the resulting mixture was stirred at RT overnight. The reaction mixture was diluted with water and was adjusted to pH 6-7 with 20% $H_2SO_4$. The mixture was filtered and washed with water. A pale solid was obtained. The crude product was recrystalized from methanol. This gave the desired product as an off-white solid (5.65 g, 13 mmol, 100%).

Synthesis of 42-5

To suspension of 20-4 (5.65 g, 13 mmol) in THF (60 mL) was added in portions lithium aluminium hydride (0.99 g, 26 mmol) at RT during 30 min period of time. Then the mixture was heated to reflux gently overnight. The mixture was cooled to 0 C and sodium sulphate 9 hydrate. The mixture was stirred for 2 h, then filtered through a pad of celite and silica gel and washed with ether first. The filtrate turned cloudy and precipitation formed. Filtration gave a white solid. The solid was recrystalized from MeOH and a colorless crystalline solid (2.43 g).

The pad of celite and silica gel was then washed 5% of MeOH in DCM (400 mL) and then 10% of MeOH in DCM with 1% of triethylamine (300 mL). The fractions containing the desired product were combined and concentrated. A white solid was obtained. The solid was recrystalized from MeOH and a colorless crystalline solid (0.79 g). The above two solids (2.43 g and 0.79 g) were combined and dried in vacuo (3.20 g, 60%). 1HNMR (CDCl3 at 7.27 ppm) δ: 2.58 (t-like, 7.2 Hz, 4H), 1.52-1.44 (m, 4H), 1.33-1.24 (m, 44H), 0.89 (t-like, 6.6 Hz, 6H), 2.1-1.3 (very broad, 1H).

Synthesis of 42-6

To a solution of 20-5 (7 mmol, 2.87 g) and triethylamine (30 mmol, 4.18 mL) in DCM (100 mL) was added a solution of mPEG-NHS (from NOF, 5.0 mmol, 9.97 g, PEG MW approx. 2,000, n=about 45) in DCM (120 mL,). After 24 h the reaction solution was washed with water (300 mL). The aqueous phase was extracted twice with DCM (100 mL×2). DCM extracts were combined, washed with brine (100 mL). The organic phase was dried over sodium sulfate, filtered, concentrated partially. The concentrated solution (ca 300 mL) was cooled at ca −15 C. Filtration gave a white solid (1.030 g, the unreacted starting amine). To the filtration was added Et3N (1.6 mmol, 0.222 mL, 4 eq) and acetic anhydride (1.6 mmol, 164 mg). The mixture was stirred at RT for 3 h and then concentrated to a solid. The residual solid was purified by column chromatography on silica gel (0-8% methanol in DCM). This gave the desired product as a white solid (9.211 g). 1HNMR (CDCl3 at 7.27 ppm) δ: 4.19 (s, 2H), 3.83-3.45 (m, 180-200H), 3.38 (s, 3H), 3.28 (t-like, 7.6 Hz, 2H, $CH_2N$), 3.18 (t-like, 7.8 Hz, 2H, CH2N), 1.89 (s, 6.6; H, water), 1.58-1.48 (m, 4H), 1.36-1.21 (m, 48-50H), 0.88 (t-like, 6.6 Hz, 6H).

EXAMPLE 43

Synthesis of PEG Lipid

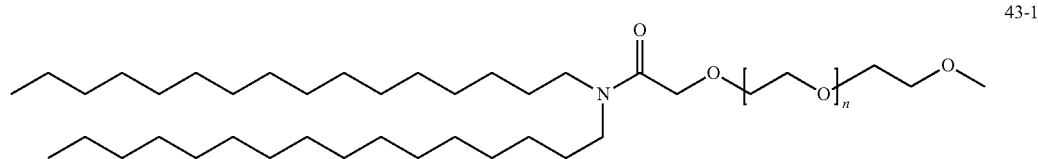

43-1

A suspension of palmitic acid (10 g) in benzene (50 mL) was treated with oxalyl chloride (5 mL) for three hours. The solvent was removed and the residue dissolved in dichloromethane (40 mL). The solution was slowly added to concentrated ammonia (100 mL) with stirring. The resultant suspension was filtered and washed with water. The precipitate was suspended in methanol, warmed to 50 C to dissolve the solid and then cooled to room temperature. The recrystallized crude product was filtered and dried, yielding a hexadecanoylamide as a white solid (8.7 g).

The crude product was suspended in THF (50 mL) and treated with lithium aluminum hydride (1.1 g, added slowly). The reaction mixture was stirred for an hour. Excess methanol was added slowly, followed by water (2 mL). Dichloromethane (200 mL) was added and the mixture filtered. The solvent was removed from the filtrate, yielded crude hexadecylamine (7 g)

A solution of hexadecyanoyl chloride (10.5 g) prepared as above, in dichlormethane (40 mL) was added slowly to a solution of the crude hexdecylamine in dichlormethane (40 mL) with stirring. Triethylamine (15 mL) was added and the solution stirred at room temperature overnight. The solution was filtered and the collected precipitate (N-(hexadecanoyl) hexadecylamide, approximately 10.7 g) dried under vacuum.

The crude product was suspended in THF (60 mL) and treated with lithium aluminum hydride (1.1 g, added slowly). The reaction mixture was stirred at room temperature overnight. Excess methanol was added slowly, followed by water (3 mL). Dichloromethane (250 mL) was added and the solution filtered. The solvent was removed, yielding crude dihexadecylamine (7.6 g) as a white powder.

A solution of dihexadecylamine (3 g) and monomethoxy-PEG-2000-acetoyl N-hydroxysuccinimide ester (10 g) in dichloromethane (60 mL) was treated with triethylamine (3 mL) and stirred overnight. Acetic anhydride (1 mL) was added and the solution stirred for 30 minutes. The reaction mixture was diluted with dichloromethane and washed with brine. The organic fraction was dried over magnesium sulfate, filtered and the solvent removed. The residue was passed down silica gel (75 g) columns using a 0-8% Methanol/dichloromethane gradient to yield 43-1 as a white powder (5.2 g).

EXAMPLE 44

Synthesis of PEG Lipid

A suspension of stearic acid (6.5 g) in benzene (20 mL) was treated with oxalyl chloride (7 mL) for three days. The solvent was removed and the residue dissolved in benzene (40 mL). Concentrated ammonia (50 mL) was slowly added with stirring. The resultant suspension was filtered and washed with water. The precipitate was suspended in methanol and filtered. The collected precipitate was washed with methanol and dried, yielding a octadecanoylamide as a white powder (6.5 g).

The crude product was suspended in THF (80 mL) and treated with excess lithium aluminum hydride (1.6 g, added slowly). The reaction mixture was stirred for an hour. Excess methanol was added slowly, followed by concentrated hydrochloric acid until the precipitate dissolved. The reaction mixture was diluted with water and allowed to recrystallize. The solution was filtered and the collected precipitate dried, yielded crude octadecylamine (5.9 g)

A solution of octadecyanoyl chloride (8 g) prepared as above, in dichloromethane (40 mL) was treated with the crude octadecylamine with stirring. Triethylamine (15 mL) and hexane (100 mL) were added and the solution stirred at 45 C for an hour. The solution was cooled, filtered and the collected precipitate washed with methanol. The precipitate was recrystallized from dichloromethane, yielding N-(octadecanoyl)octadecylamide (6.8 g) as a white powder.

The product was suspended in THF (150 mL) and treated with lithium aluminum hydride (1.5 g, added slowly). The reaction mixture was refluxed overnight. Excess methanol was added slowly, followed by concentrated hydrochloric acid until the precipitate dissolved. The solution was diluted with water and allowed to crystallize. The solution was filtered and the collected precipitate washed with water (4x). The precipitate was dried under vacuum, yielding dioctadecylamine (6.2 g) as a white powder.

A solution of dioctadecylamine (4.5 g) and monomethoxy-PEG-2000-acetoyl N-hydroxysuccinimide ester (9 g) in chloroform (90 mL) was treated with triethylamine (40 mL) and stirred at 50 C for 30 minutes. The solution was filtered. Acetic anhydride (1 mL) was added to the filtrate and the solution stirred for 15 minutes. Ammonia (150 mL) was added, followed by brine (150 mL). The reaction mixture was extracted with dichloromethane and the organic phase washed with dilute hydrochloric acid. The organic fraction was dried over magnesium sulfate, filtered and the solvent removed. The residue was passed down

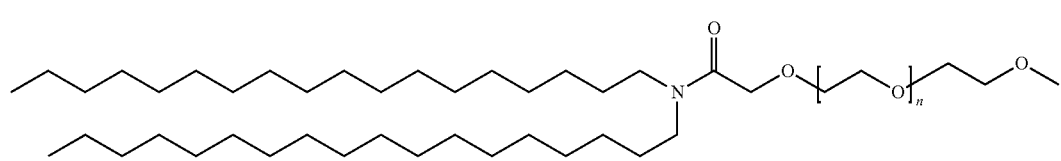

44-1

EXAMPLE 45

Synthesis of PEG Lipid

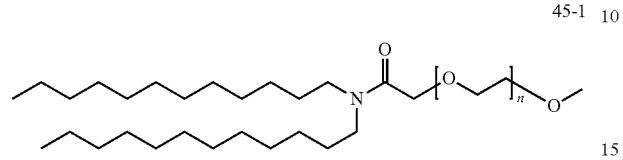

45-1

A suspension of lauric acid (10 g) in benzene (20 mL) was treated with oxalyl chloride (10 mL) for an hour. The solvent was removed and the residue dissolved in dichloromethane (50 mL). The solution was slowly added to concentrated ammonia (150 mL) with stirring. The reaction mixture was washed with dichloromethane. The organic phase was dried over magnesium sulfate, filtered and the solvent removed, yielding crude dodecanoylamide as a white powder (10 g).

The product was suspended in THF (150 mL) and treated with lithium aluminum hydride (3 g, added slowly). The reaction mixture was stirred for an hour. Excess methanol was added slowly, followed by aqueous sodium hydroxide solution (5 mL). Dichloromethane (100 mL) was added and the resultant suspension filtered. The solvent was removed from the filtrate, and the residue passed down a silica gel (80 g) column using a methanol/dichloromethane gradient, yielding dodecanylamine (4.5 g).

A solution of lauric acid (7.3 g), crude tetradecylamine (4.5 g) and N-hydroxysuccinimide (4.2 g) in dichloromethane (200 mL) was treated with EDC (7.0 g) followed by triethylamine (15 mL), and the solution stirred at room temperature overnight. The solution was filtered yielding crude N-dodecanoyldodecanylamide (1 g) as a powder. The solvent was removed from the filtrate, the residue suspended in methanol and filtered, yielding a further 2 g of crude N-dodecanoyldodecanylamide.

The crude product (3 g) was suspended in THF (60 mL) and treated with lithium aluminum hydride (excess, added slowly) for two hours. Excess methanol was added slowly, followed by water (1 mL). Dichloromethane (100 mL) was added and the suspension filtered. The solvent was removed from the filtrate and the residue passed down a silica gel column (20 g) using a 0-12% methanol/dichloromethane gradient yielding N-dodecanoyldodecanylamine (1.4 g) as a waxy solid.

A solution of N-dodecanyldodecanylamine (0.52 g) and monomethoxy-PEG-2000-acetoyl N-hydroxysuccinimide ester (1.5 g) in dichloromethane (10 mL) was treated with triethylamine (0.2 mL) and stirred overnight. The solvent was removed and the product passed down a silica gel column (20 g) using a 0-6% methanol/dichloromethane gradient. Acetic anhydride (5 drops) and trimethylamine (10 drops) was added to a solution of the recovered product in dichloromethane and allowed to stir for an hour. The solvent removed and the residue was passed down a silica gel (20 g) column using a 0-4% methanol/dichloromethane gradient to yield MePEGA-2000-DLA as a white powder (0.44 g).

EXAMPLE 46

Synthesis of PEG Lipid

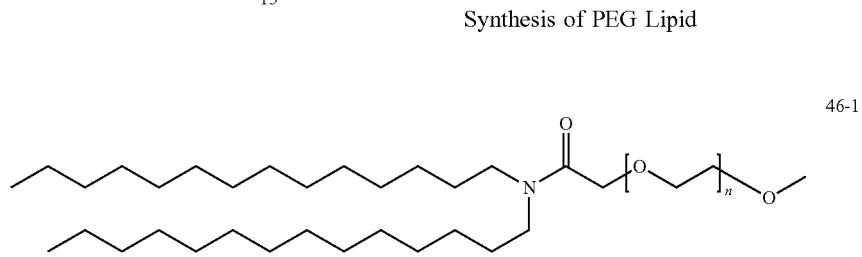

46-1

A suspension of myristic acid (30 g) in benzene (100 mL) was treated with oxalyl chloride (15 mL) overnight. The solvent was removed and the residue dissolved in dichloromethane (100 mL). The solution was slowly added to concentrated ammonia (70 mL) with stirring. The resultant suspension was filtered and washed with water. The precipitate was dried, yielding crude tetradecanoylamide as a white solid (27 g).

The product was suspended in THF (200 mL) and treated with lithium aluminum hydride (4.5 g, added slowly). The reaction mixture was stirred for an hour. Excess methanol was added slowly, followed by water (10 mL). Dichloromethane (250 mL) was added and the resultant suspension filtered. The solvent was removed from the filtrate, yielded crude tetradecylamine (17.6 g).

A solution of lauric acid (3.5 g), crude tetradecylamine (3 g) and N-hydroxysuccinimide (1.9 g) in dichloromethane (40 mL) was treated with EDC (3.3 g) followed by triethylamine (4 mL), and the solution stirred at room temperature for three days. The solution was filtered and the collected precipitate dried, yielding crude N-lauroyltetradecanylamine (2.6 g) as a powder.

The crude product was suspended in THF (60 mL) and treated with lithium aluminum hydride (0.8 g, added slowly) for one hour. Excess methanol was added slowly, followed by water (2 mL). Dichloromethane was added and the suspension filtered. The solvent was removed and the residue dissolved in hot methanol (100 mL). The solution was cooled and filtered to yield 0.5 g of N-dodecanyltetradecanylamine. The solvent was removed from the filtrate and the process repeated with 20 mL methanol to produce a second crop of N-dodecanyltetradecanylamine (0.9 g)

A solution of N-dodecanyltetradecanylamine (0.5 g) and monomethoxy-PEG-2000-acetoyl N-hydroxysuccinimide ester (1.5 g) in dichloromethane (10 mL) was treated with triethylamine (0.2 mL) and stirred overnight. The solvent was removed and the product passed down a silica gel column (20 g) using a 0-6% methanol/dichloromethane gradient. Acetic anhydride (5 drops) and trimethylamine (10 drops) was added to a solution of the recovered product in dichloromethane and allowed to stir for an hour. The solvent removed and the residue was passed down a silica gel (20 g) column using a 0-4% methanol/dichloromethane gradient to yield MePEGA-2000-LMA as a white powder (0.76 g).

EXAMPLE 47

Luciferase mRNA In Vivo Evaluation Using the Lipid Nanoparticle Compositions Cationic lipid (MC3), DSPC, cholesterol and PEG-lipid were solubilized in ethanol at a molar ratio of 50:10:38.5:1.5. Lipid nanoparticles (LNP) were prepared at a total lipid to mRNA weight ratio of approximately 10:1 to 30:1. Briefly, the mRNA was diluted to 0.2 mg/mL in 10 to 50 mM citrate buffer, pH 4. Syringe pumps were used to mix the ethanolic lipid solution with the mRNA aqueous solution at a ratio of about 1:5 to 1:3 (vol/vol) with total flow rates above 15 ml/min. The ethanol was then removed and the external buffer replaced with PBS by dialysis. Finally, the lipid nanoparticles were filtered through a 0.2 μm pore sterile filter. Lipid nanoparticle particle size was 70-90 nm diameter as determined by quasi-elastic light scattering using a Nicomp 370 submicron particle sizer (Santa Barbara, Calif.).

Studies were performed in 6-8 week old female C57BL/6 mice (Charles River) according to guidelines established by an institutional animal care committee (ACC) and the Canadian Council on Animal Care (CCAC). Varying doses of mRNA-lipid nanoparticle were systemically administered by tail vein injection and animals euthanized at specific time points (1, 2, 4, 8 and 24 hrs) post-administration. Liver and spleen were collected in pre-weighted tubes, weights determined, immediately snap frozen in liquid nitrogen and stored at −80° C. until processing for analysis.

For liver, approximately 50 mg was dissected for analyses in a 2 mL FastPrep tubes (MP Biomedicals, Solon Ohio). ¼" ceramic sphere (MP Biomedicals) was added to each tube and 500 μL of Glo Lysis Buffer—GLB (Promega, Madison Wis.) equilibrated to room temperature was added to liver tissue. Liver tissues were homogenized with the FastPrep24 instrument (MP Biomedicals) at 2×6.0 m/s for 15 seconds. Homogenate was incubated at room temperature for 5 minutes prior to a 1:4 dilution in GLB and assessed using SteadyGlo Luciferase assay system (Promega). Specifically, 50 μL of diluted tissue homogenate was reacted with 50 μL of SteadyGlo substrate, shaken for 10 seconds followed by 5 minute incubation and then quantitated using a CentroXS³ LB 960 luminometer (Berthold Technologies, Germany). The amount of protein assayed was determined by using the BCA protein assay kit (Pierce, Rockford Ill.). Relative luminescence units (RLU) were then normalized to total ug protein assayed. To convert RLU to ng luciferase a standard curve was generated with QuantiLum Recombinant Luciferase (Promega). Based in the data provided in FIG. 1, the four-hour time point was chosen for efficacy evaluation of the lipid formulations (see EXAMPLE 48).

The FLuc mRNA (L-6107) from Trilink Biotechnologies will express a luciferase protein, originally isolated from the firefly, Photinus pyralis. FLuc is commonly used in mammalian cell culture to measure both gene expression and cell viability. It emits bioluminescence in the presence of the substrate, luciferin. This capped and polyadenylated mRNA is fully substituted with 5-methylcytidine and pseudouridine.

EXAMPLE 48

Determination of Efficacy of Lipid Nanoparticle Formulations Containing Various Cationic Lipids Using an In Vivo Luciferase mRNA Expression Rodent Model The cationic lipids shown in Table 2 have previously been tested with nucleic acids. For comparative purposes, these lipids were also used to formulate lipid nanoparticles containing the FLuc mRNA (L-6107) using an in line mixing method, as described in EXAMPLE 47 and in PCT/US10/22614, which is hereby incorporated by reference in its entirety. Lipid nanoparticles were formulated using the following molar ratio: 50% Cationic lipid/10% distearoylphosphatidylcholine (DSPC)/38.5% Cholesterol/1.5% PEG lipid ("PEG-DMG", i.e., (1-(monomethoxy-polyethyleneglycol)-2,3-dimyristoylglycerol, with an average PEG molecular weight of 2000). Relative activity was determined by measuring luciferase expression in the liver 4 hours following administration via tail vein injection as described in EXAMPLE 47. The activity was compared at a dose of 0.3 and 1.0 mg mRNA/kg and expressed as ng luciferase/g liver measured 4 hours after administration, as described in EXAMPLE 47.

TABLE 2

| | | | |
|---|---|---|---|
| | Lipids showing activity with mRNA | | |
| Compound | Liver Luc @ 0.3 mg/kg dose | Liver Luc @ 1.0 mg/kg dose | Structure |
| MC2 | 4 ± 1 | N/D | |
| DLinDMA | 13 ± 3 | 67 ± 20 | |

TABLE 2-continued

Lipids showing activity with mRNA

| Compound | Liver Luc @ 0.3 mg/kg dose | Liver Luc @ 1.0 mg/kg dose | Structure |
|---|---|---|---|
| MC4 | 41 ± 10 | N/D | 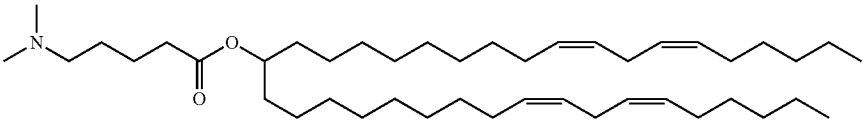 [SMILES: CCCCC/C=C\C/C=C\CCCCCCCCC(CCCCCCCC/C=C\C/C=C\CCCCC)OC(=O)CCCCN(C)C] |
| XTC2 | 80 ± 28 | 237 ± 99 | 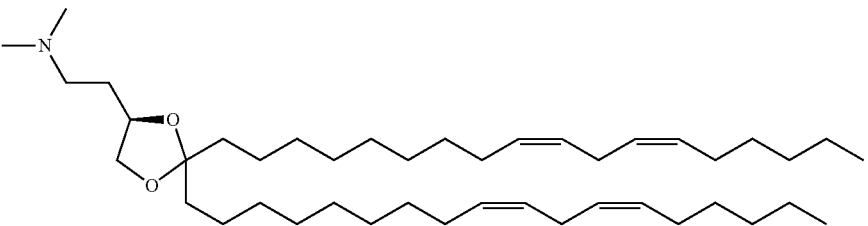 [SMILES: CCCCC/C=C\C/C=C\CCCCCCCCC1(CCCCCCCC/C=C\C/C=C\CCCCC)OC[C@@H](CCN(C)C)O1] |
| MC3 | 198 ± 126 | 757 ± 528 | 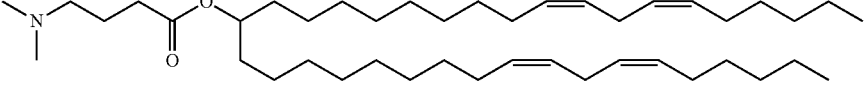 |
| 319 (2% PEG) | 258 ± 67 | 681 ± 203 | 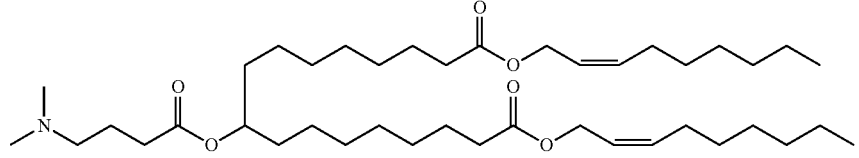 [SMILES: CCCCCC/C=C\COC(=O)CCCCCCCC(CCCCCCCC(=O)OC/C=C\CCCCCC)OC(=O)CCCN(C)C] |
| 137 | 281 ± 203 | 588 ± 303 | 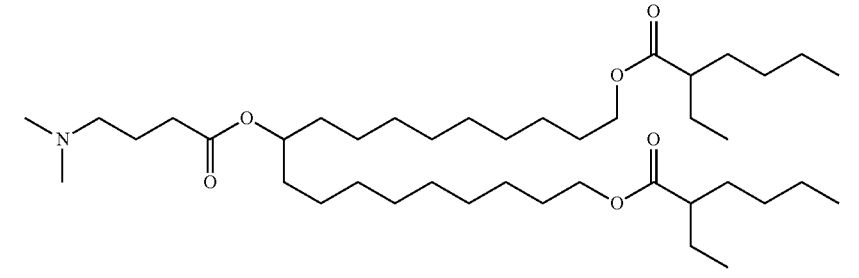 [SMILES: CCCCC(CC)C(=O)OCCCCCCCCCC(CCCCCCCCCOC(=O)C(CC)CCCC)OC(=O)CCCN(C)C] |

The novel lipids of the invention shown in Table 3 were formulated using the following molar ratio: 50% cationic lipid/10% distearoylphosphatidylcholine (DSPC)/38.5% Cholesterol/1.5% PEG lipid ("PEG-DMA" compound 42-6). Relative activity was determined by measuring luciferase expression in the liver 4 hours following administration via tail vein injection as described in EXAMPLE 47. The activity was compared at a dose of 0.3 and 1.0 mg mRNA/kg and expressed as ng luciferase/g liver measured 4 hours after administration, as described in EXAMPLE 47.

TABLE 3
Novel Cationic lipids
| No. | pK$_a$ | Liver Luc @ 0.3 mg/kg (ng luc/g liver) | Liver Luc @ 1.0 mg/kg (ng luc/g liver) | Structure |
|---|---|---|---|---|
| 2 | 5.64 | 23 ± 6 | 84 ± 24 | 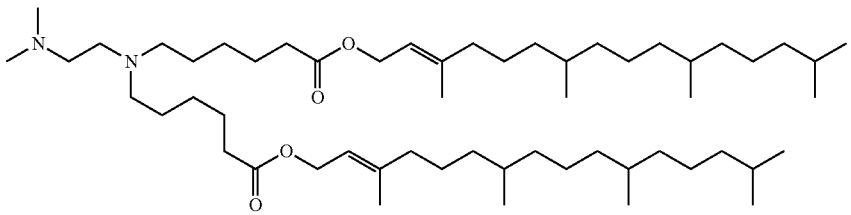 [SMILES: C/C(=C\COC(=O)CCCCCN(CCCCCC(=O)OC/C=C(\C)CCCC(C)CCCC(C)CCCC(C)C)CCN(C)C)CCCC(C)CCCC(C)CCCC(C)C] |
| 3 | 7.15 | 1.5 ± 0.6 | 0.32 ± 0.1 | 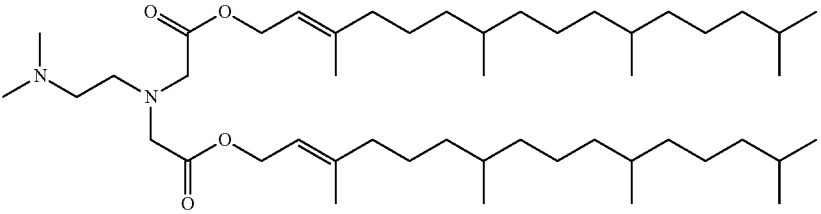 [SMILES: C/C(=C\COC(=O)CN(CCN(C)C)CC(=O)OC/C=C(\C)CCCC(C)CCCC(C)CCCC(C)C)CCCC(C)CCCC(C)CCCC(C)C] |
| 4 | 6.43 | 53 ± 10 | 126 ± 102 | 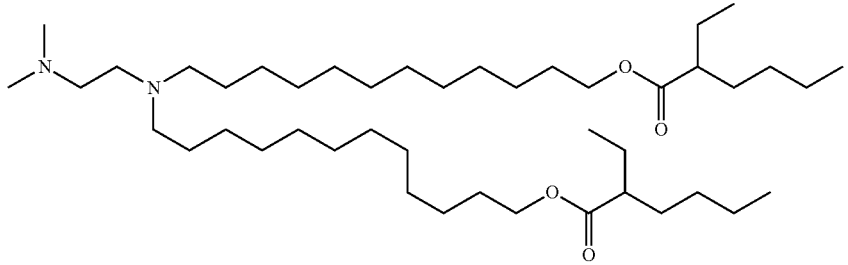 [SMILES: CCCCC(CC)C(=O)OCCCCCCCCCCCCN(CCCCCCCCCCCCOC(=O)C(CC)CCCC)CCN(C)C] |
| 5 | 6.28 | 1571 ± 414 | 12900 ± 4083 | 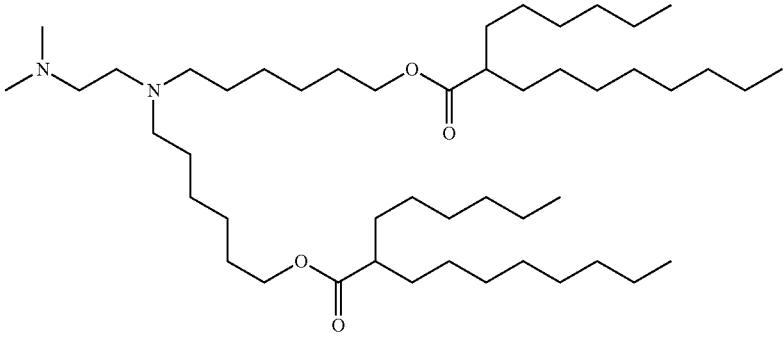 [SMILES: CCCCCCCCC(CCCCCC)C(=O)OCCCCCCN(CCCCCCOC(=O)C(CCCCCC)CCCCCCCC)CCN(C)C] |
| 6 | 6.12 | 2015 ± 135 | 16006 ± 2487 | 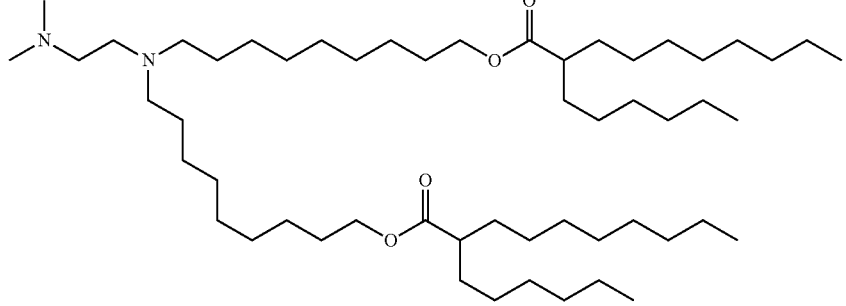 |

TABLE 3-continued

Novel Cationic lipids

| No. | pK$_a$ | Liver Luc @ 0.3 mg/kg (ng luc/g liver) | Liver Luc @ 1.0 mg/kg (ng luc/g liver) | Structure |
|---|---|---|---|---|
| 11 | 6.36 | 328 ± 12 | 1266 ± 522 | 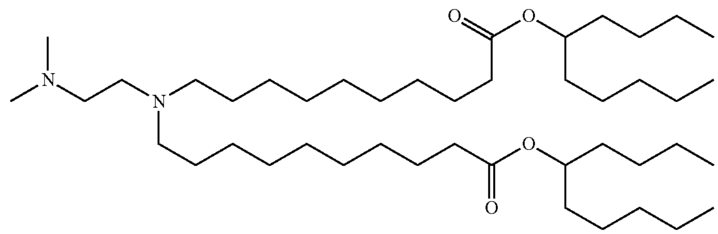 [SMILES: CCCCCC(CCCC)OC(=O)CCCCCCCCCN(CCCCCCCCCC(=O)OC(CCCC)CCCCC)CCN(C)C] |
| 13 | 6.51 | 16 ± 4 | 20 ± 20 | 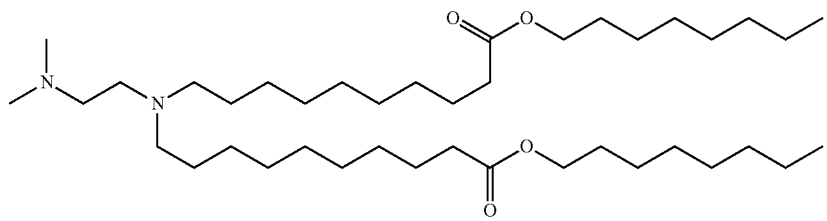 [SMILES: CCCCCCCCOC(=O)CCCCCCCCCN(CCCCCCCCCC(=O)OCCCCCCCC)CCN(C)C] |
| 15 | 6.30 | 66 ± 32 | 243 ± 71 | 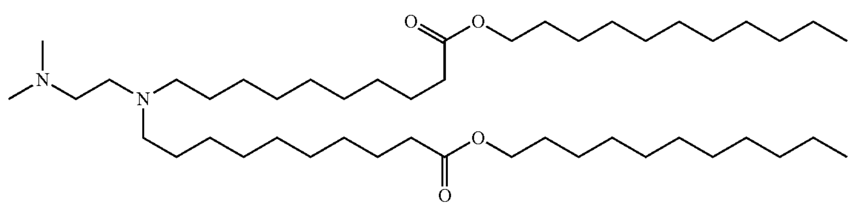 [SMILES: CCCCCCCCCCCOC(=O)CCCCCCCCCN(CCCCCCCCCC(=O)OCCCCCCCCCCC)CCN(C)C] |
| 16 | 6.63 | 7 ± 1 | 14 ± 4 | 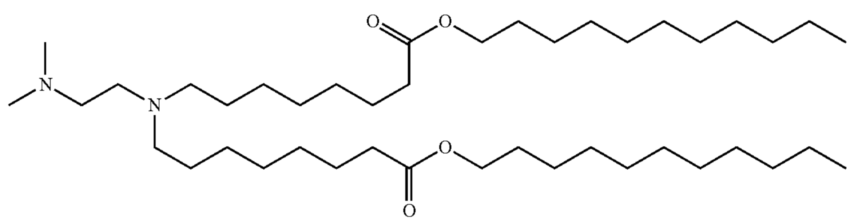 [SMILES: CCCCCCCCCCCOC(=O)CCCCCCCN(CCCCCCCC(=O)OCCCCCCCCCCC)CCN(C)C] |
| 19 | 6.72 | 8 ± 3 | 15 ± 21 | 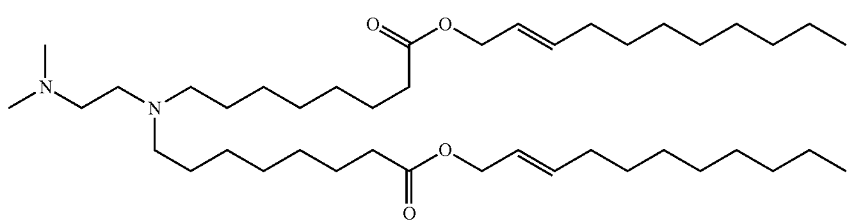 [SMILES: CCCCCCCC/C=C/COC(=O)CCCCCCCN(CCCCCCCC(=O)OC/C=C/CCCCCCCC)CCN(C)C] |
| 20 | 6.44 | 301 ± 155 | 501 ± 96 | 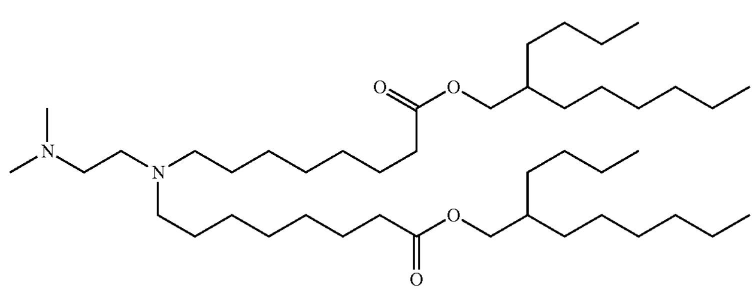 [SMILES: CCCCCCC(CCCC)COC(=O)CCCCCCCN(CCCCCCCC(=O)OCC(CCCC)CCCCCC)CCN(C)C] |

TABLE 3-continued
Novel Cationic lipids
| No. | pK$_a$ | Liver Luc @ 0.3 mg/kg (ng luc/g liver) | Liver Luc @ 1.0 mg/kg (ng luc/g liver) | Structure |
|---|---|---|---|---|
| 21 | 6.28 | 404 ± 103 | 4149 ± 2514 | 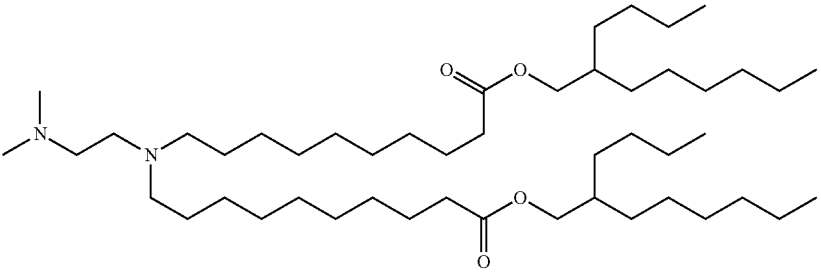 [SMILES: CCCCCCC(CCCC)COC(=O)CCCCCCCCCN(CCCCCCCCCC(=O)OCC(CCCC)CCCCCC)CCN(C)C] |
| 22 | 6.53 | 2126 ± 294 | 14486 ± 6607 | 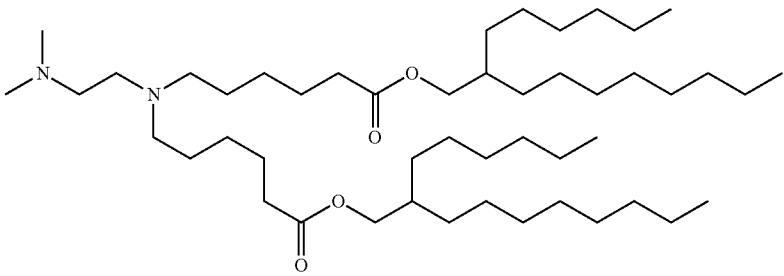 [SMILES: CCCCCCCCC(CCCCCC)COC(=O)CCCCCN(CCCCCC(=O)OCC(CCCCCC)CCCCCCCC)CCN(C)C] |
| 23 | 6.24 | 1109 ± 209 | 4568 ± 762 | 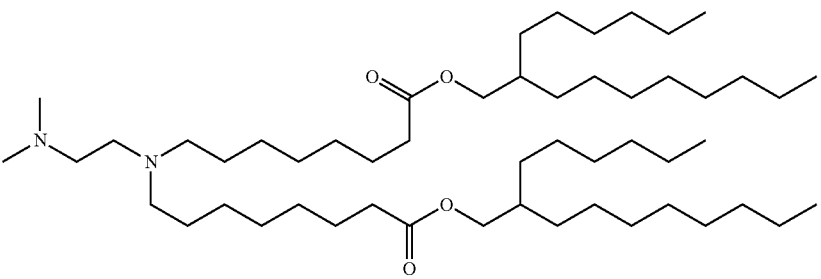 [SMILES: CCCCCCCCC(CCCCCC)COC(=O)CCCCCCCN(CCCCCCCC(=O)OCC(CCCCCC)CCCCCCCC)CCN(C)C] |
| 24 | 6.28 | 1094 ± 180 | 6928 ± 1015 | 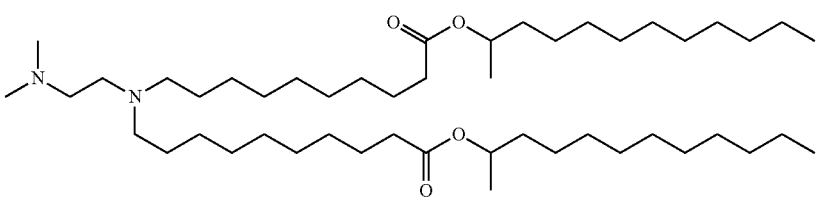 [SMILES: CCCCCCCCCCC(C)OC(=O)CCCCCCCCCN(CCCCCCCCCC(=O)OC(C)CCCCCCCCCC)CCN(C)C] |
| 25 | 6.20 | 901 ± 173 | 6223 ± 1714 | 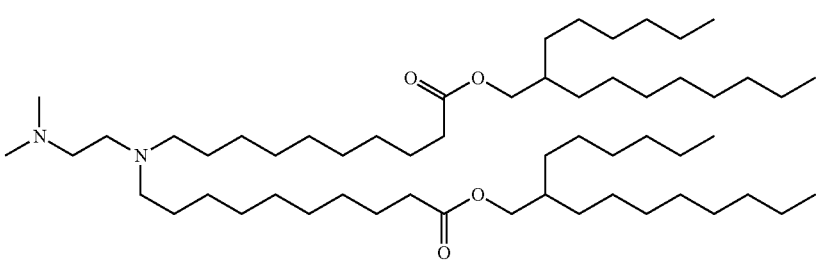 [SMILES: CCCCCCCCC(CCCCCC)COC(=O)CCCCCCCCCN(CCCCCCCCCC(=O)OCC(CCCCCC)CCCCCCCC)CCN(C)C] |
| 26 | 6.89 | 30 ± 5 | 55 ± 0.8 | 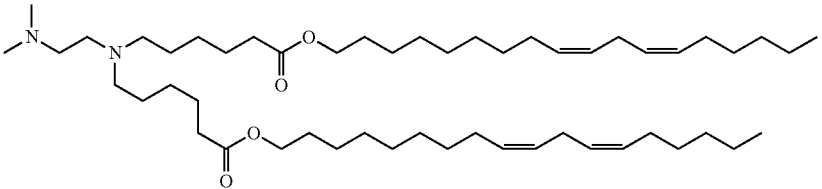 [SMILES: CCCCC/C=C\C/C=C\CCCCCCCCOC(=O)CCCCCN(CCCCCC(=O)OCCCCCCCC/C=C\C/C=C\CCCCC)CCN(C)C] |

TABLE 3-continued

Novel Cationic lipids

| No. | pK$_a$ | Liver Luc @ 0.3 mg/kg (ng luc/g liver) | Liver Luc @ 1.0 mg/kg (ng luc/g liver) | Structure |
|---|---|---|---|---|
| 27 | 6.30 | 724 ± 144 | 6636 ± 1230 | 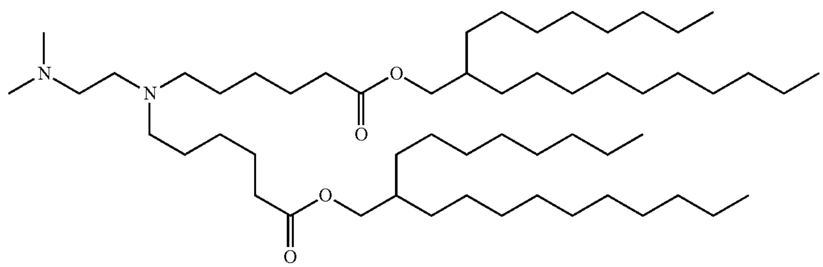 [SMILES: CCCCCCCCCCC(CCCCCCCC)COC(=O)CCCCCN(CCCCCC(=O)OCC(CCCCCCCC)CCCCCCCCCC)CCN(C)C] |
| 28 | 6.20 | 522 ± 86 | 4582 ± 1291 | 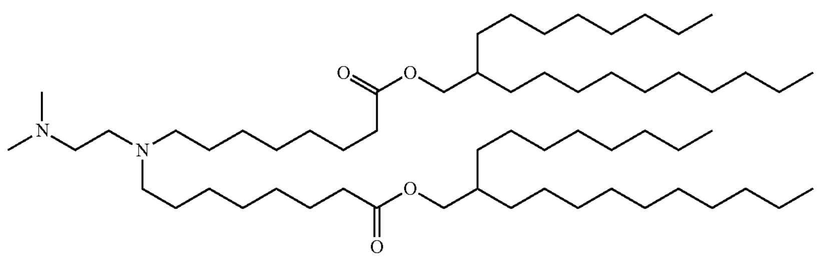 [SMILES: CCCCCCCCCCC(CCCCCCCC)COC(=O)CCCCCCCN(CCCCCCCC(=O)OCC(CCCCCCCC)CCCCCCCCCC)CCN(C)C] |
| 29 | 6.22 | 1303 ± 445 | 9750 ± 3519 | 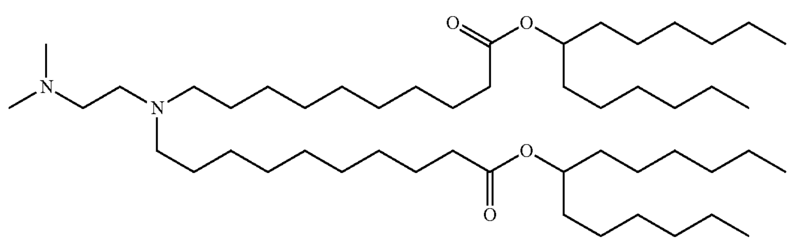 [SMILES: CCCCCCC(CCCCCC)OC(=O)CCCCCCCCCN(CCCCCCCCCC(=O)OC(CCCCCC)CCCCCC)CCN(C)C] |
| 31 | 6.33 | 344 ± 160 | 4103 ± 1073 | 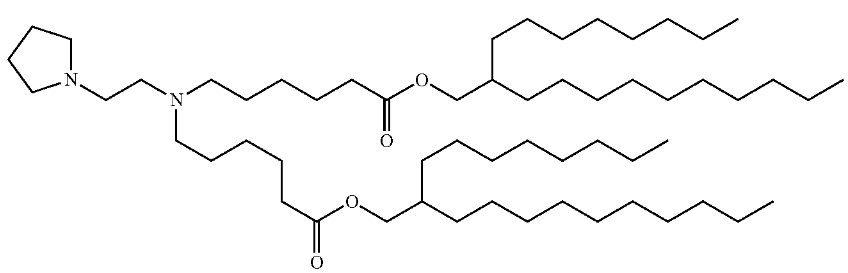 [SMILES: CCCCCCCCCCC(CCCCCCCC)COC(=O)CCCCCN(CCCCCC(=O)OCC(CCCCCCCC)CCCCCCCCCC)CCN1CCCC1] |
| 32 | 6.47 | 626 ± 299 | 12266 ± 192 | 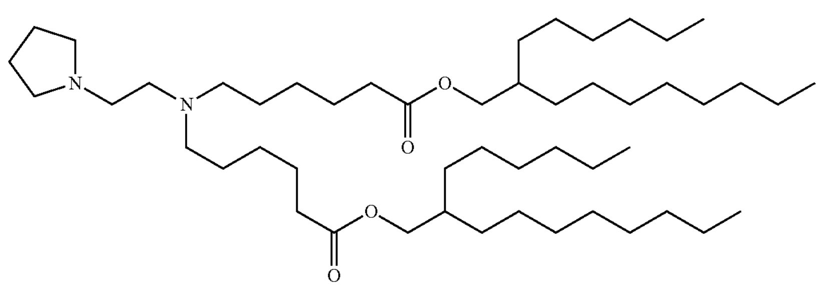 [SMILES: CCCCCCCCC(CCCCCC)COC(=O)CCCCCN(CCCCCC(=O)OCC(CCCCCC)CCCCCCCC)CCN1CCCC1] |

TABLE 3-continued
Novel Cationic lipids
| No. | pK$_a$ | Liver Luc @ 0.3 mg/kg (ng luc/g liver) | Liver Luc @ 1.0 mg/kg (ng luc/g liver) | Structure |
|---|---|---|---|---|
| 33 | 6.27 | 711 ± 272 | 4448 ± 512 | 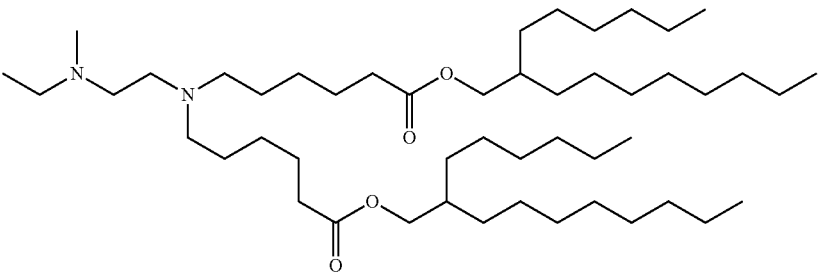 [SMILES: CCCCCCCCC(CCCCCC)COC(=O)CCCCCN(CCCCCC(=O)OCC(CCCCCC)CCCCCCCC)CCN(C)CC] |
| 35 | 6.21 | 35 ± 15 | 101 ± 69 | 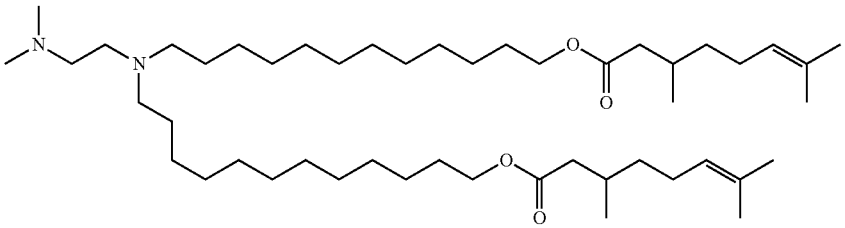 [SMILES: CC(C)=CCCC(C)CC(=O)OCCCCCCCCCCCCN(CCCCCCCCCCCCOC(=O)CC(C)CCC=C(C)C)CCN(C)C] |
| 38 | 6.24 | 977 ± 336 | 7135 ± 1020 | 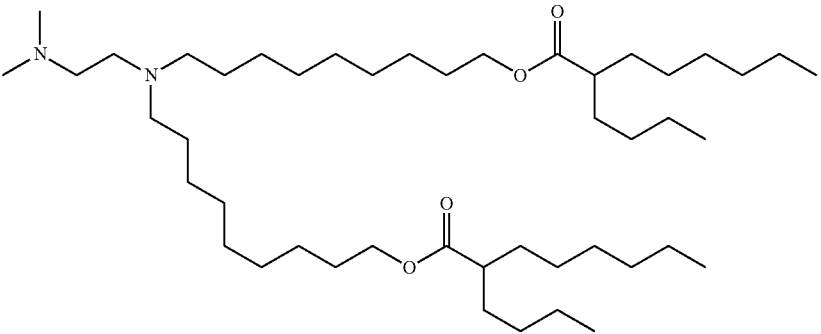 [SMILES: CCCCCCC(CCCC)C(=O)OCCCCCCCCCN(CCCCCCCCCOC(=O)C(CCCC)CCCCCC)CCN(C)C] |
| 39 | 5.82 | 36 ± 13 | 326 ± 81 | 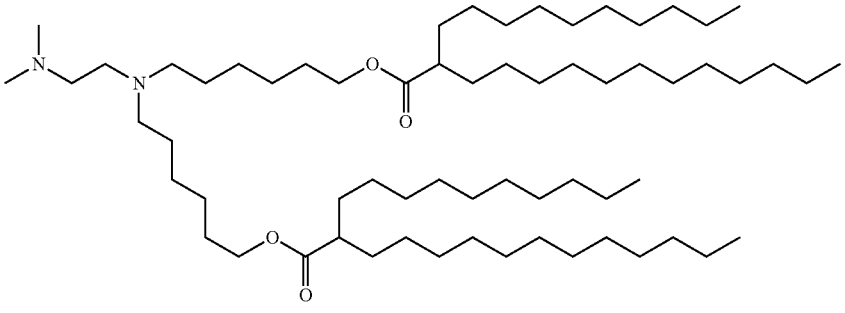 [SMILES: CCCCCCCCCCCCC(CCCCCCCCCC)C(=O)OCCCCCCN(CCCCCCOC(=O)C(CCCCCCCCCC)CCCCCCCCCCCC)CCN(C)C] |
| 40 | 6.38 | 236 ± 71 | 1704 ± 571 | 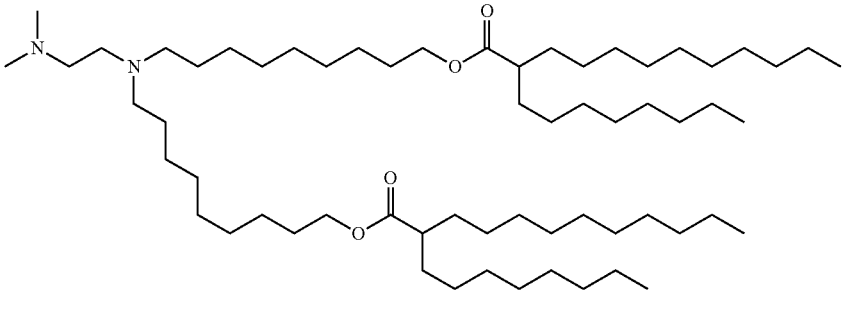 [SMILES: CCCCCCCCCCC(CCCCCCCC)C(=O)OCCCCCCCCCN(CCCCCCCCCOC(=O)C(CCCCCCCC)CCCCCCCCCC)CCN(C)C] |

TABLE 3-continued

Novel Cationic lipids

| No. | pK$_a$ | Liver Luc @ 0.3 mg/kg (ng luc/g liver) | Liver Luc @ 1.0 mg/kg (ng luc/g liver) | Structure |
|---|---|---|---|---|
| 41 | 5.91 | 63 ± 27 | 799 ± 619 | 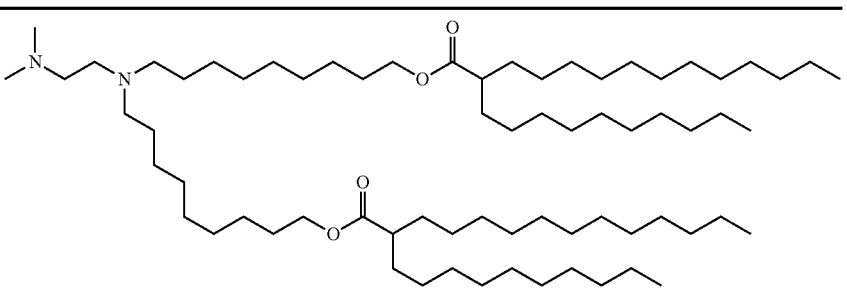 |

EXAMPLE 49

Determination of pK$_A$ of Formulated Lipids

Figure 2:
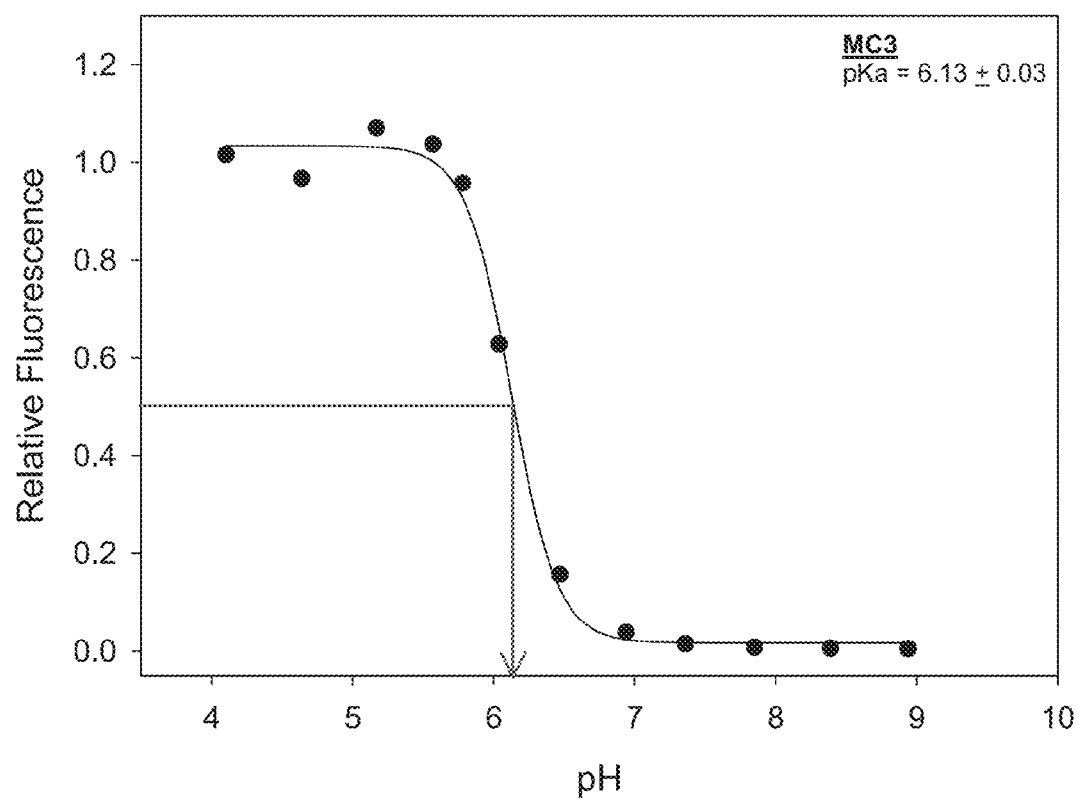
FIG. 2 illustrates the calculation of pKa for MC3 as a representative example relevant to the disclosed lipids.

As described elsewhere, the pKa of formulated cationic lipids is correlated with the effectiveness of LNPs for delivery of nucleic acids (see Jayaraman et al, Angewandte Chemie, International Edition (2012), 51(34), 8529-8533; Semple et al, Nature Biotechnology 28, 172-176 (2010)). The preferred range of pKa is ~5 to ~7. The pK$_a$ of each cationic lipid was determined in lipid nanoparticles using an assay based on fluorescence of 2-(p-toluidino)-6-napthalene sulfonic acid (TNS). Lipid nanoparticles comprising of cationic lipid/DSPC/cholesterol/PEG-lipid (50/10/38.5/1.5 mol %) in PBS at a concentration of 0.4 mM total lipid are prepared using the in-line process as described in EXAMPLE 47. TNS was prepared as a 100 µM stock solution in distilled water. Vesicles were diluted to 24 µM lipid in 2 mL of buffered solutions containing, 10 mM HEPES, 10 mM MES, 10 mM ammonium acetate, 130 mM NaCl, where the pH ranged from 2.5 to 11. An aliquot of the TNS solution was added to give a final concentration of 1 µM and following vortex mixing fluorescence intensity was measured at room temperature in a SLM Aminco Series 2 Luminescence Spectrophotometer using excitation and emission wavelengths of 321 nm and 445 nm. A sigmoidal best fit analysis was applied to the fluorescence data and the pK$_a$ was measured as the pH giving rise to half-maximal fluorescence intensity (see FIG. 2).

EXAMPLE 50

Figure 3:
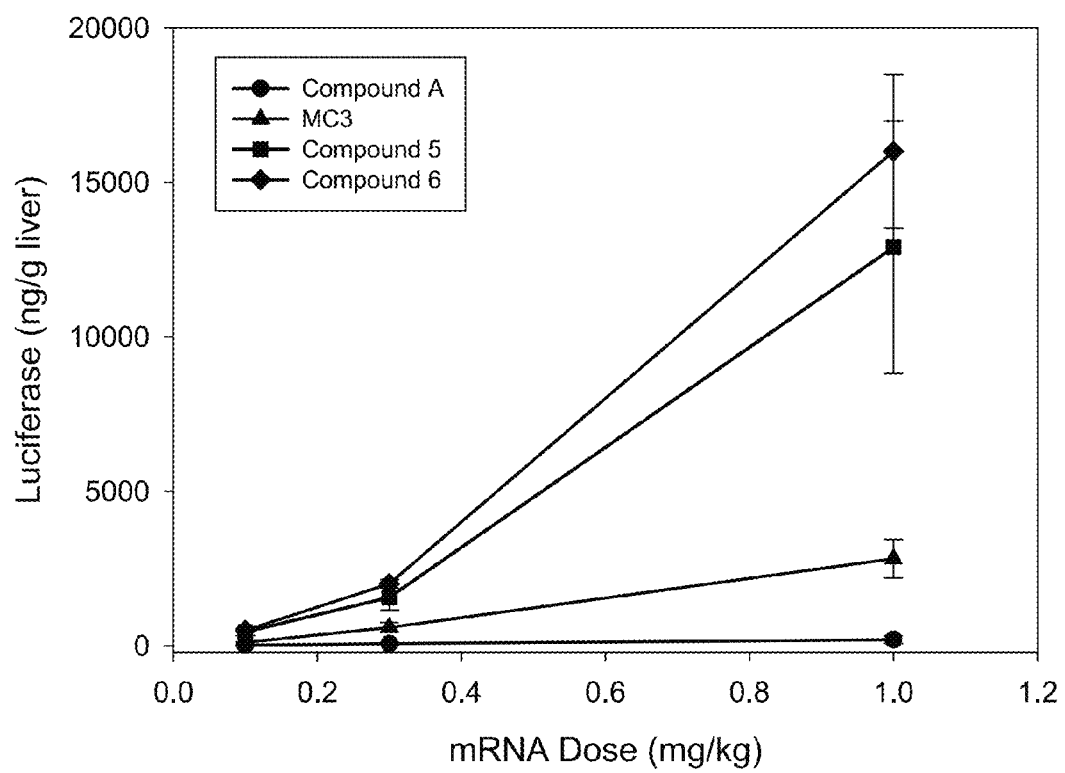
FIG. 3 provides comparative luciferase activity data for different lipids.

Comparative Activity of Amino Lipids and the Effect of Hydrocarbon Chain Structure The cationic lipids shown in Table 5 were formulated using the following molar ratio: 50% Cationic lipid/10% distearoylphosphatidylcholine (DSPC)/38.5% Cholesterol/1.5% PEG-lipid (42-6). Relative activity was determined by measuring luciferase expression in the liver 4 hours following administration via tail vein injection as described in EXAMPLE 48. The activity was compared at a dose of 0.1, 0.3 and 1.0 mg mRNA/kg and expressed as ng luciferase/g liver measured 4 hours after administration, as described in EXAMPLE 48. Data is plotted in FIG. 3 (from top to bottom: diamond=compound 6; square=compound 5; triangle=MC3; and circle=compound A). Compounds A, 5 and 6 have a common headgroup but different hydrocarbon chain structures.

TABLE 5

Comparative Data

| Compound | pKa | Liver Luc @ 0.3 mg/kg (ng luc/ g liver) | Liver Luc @ 1.0 mg/kg (ng luc/g liver) | Structure |
|---|---|---|---|---|
| MC3 | 6.09 | 603 ± 150 | 2876 ± 622 | 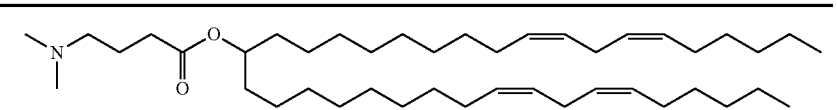 |
| A | 6.26 | 77 ± 40 | 203 ± 122 | 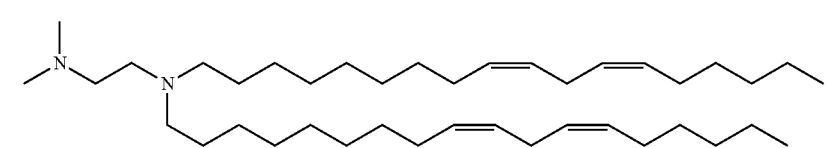 [SMILES: CCCCC/C=C\C/C=C\CCCCCCCCN(CCCCCCCC/C=C\C/C=C\CCCCC)CCN(C)C] |

TABLE 5-continued

Comparative Data

| Compound | pKa | Liver Luc @ 0.3 mg/kg (ng luc/ g liver) | Liver Luc @ 1.0 mg/kg (ng luc/g liver) | Structure |
|---|---|---|---|---|
| 5 | 6.28 | 1571 ± 414 | 12900 ± 4083 | 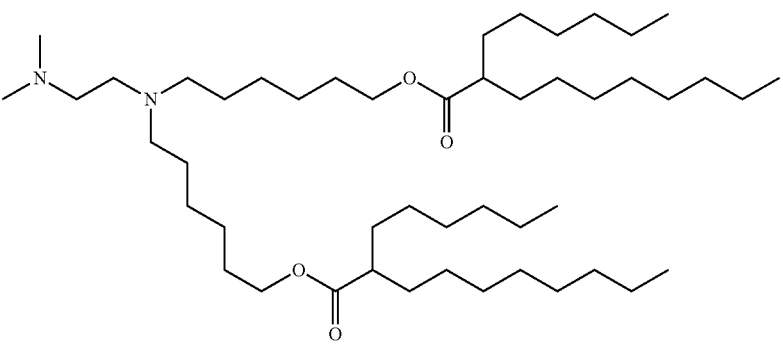 [SMILES: CCCCCCCCC(CCCCCC)C(=O)OCCCCCCN(CCCCCCOC(=O)C(CCCCCC)CCCCCCCC)CCN(C)C] |
| 6 | 6.12 | 2015 ± 135 | 16006 ± 2487 | 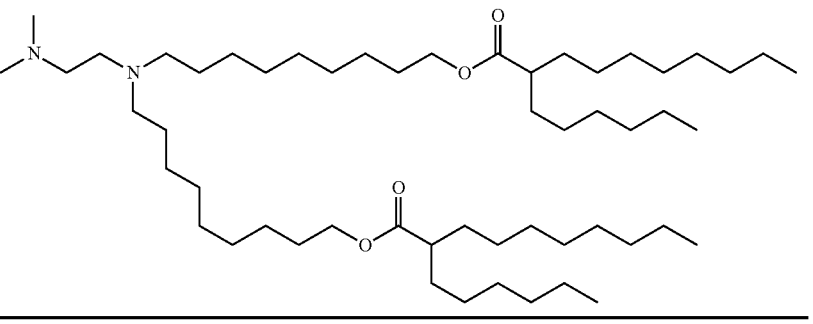 |

EXAMPLE 51

Comparative Activity of Cationic Lipids and the Effect of Headgroup Chain Length The cationic lipids shown in Table 6 were formulated using the following molar ratio: 50% Cationic lipid/10% distearoylphosphatidylcholine (DSPC)/38.5% Cholesterol/ 1.5% PEG-lipid (42-6). Relative activity was determined by measuring luciferase expression in the liver 4 hours following administration via tail vein injection as described in EXAMPLE 48. The activity was compared at a dose of 0.1, 0.3 and 1.0 mg mRNA/kg and expressed as ng luciferase/g liver measured 4 hours after administration, as described in EXAMPLE 48. Compounds A, B and C have common hydrocarbon chain structure but different headgroup chain length. Compound 6 shares a preferred headgroup with compound A and demonstrates the unexpected advantage of the combination of headgroup and hydrocarbon chain structure.

TABLE 6

Comparative Data

| Compound | pKa | Liver Luc @ 0.3 mg/kg (ng luc/ g liver) | Liver Luc @ 1.0 mg/kg (ng luc/g liver) | Structure |
|---|---|---|---|---|
| A | 6.26 | 77 ± 40 | 203 ± 122 | 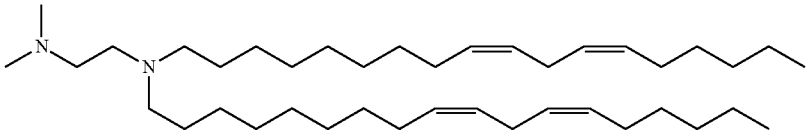 |
| B | 6.68 | 3 ± 0.8 | 12 ± 4 | 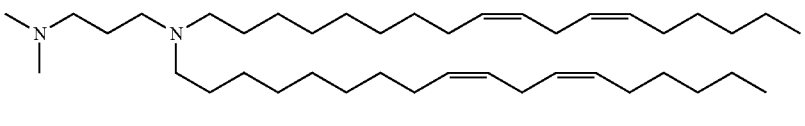 |

TABLE 6-continued

Comparative Data

| Compound | pKa | Liver Luc @ 0.3 mg/kg (ng luc/g liver) | Liver Luc @ 1.0 mg/kg (ng luc/g liver) | Structure |
|---|---|---|---|---|
| C | 7.32 | 2 ± 0.5 | 7 ± 2 | (structure) |
| 6 | 6.12 | 2015 ± 135 | 16006 ± 2487 | (structure) |

EXAMPLE 52

Comparative Activity of PEG-DMG and PEG-DMA Lipids

Figure 4:
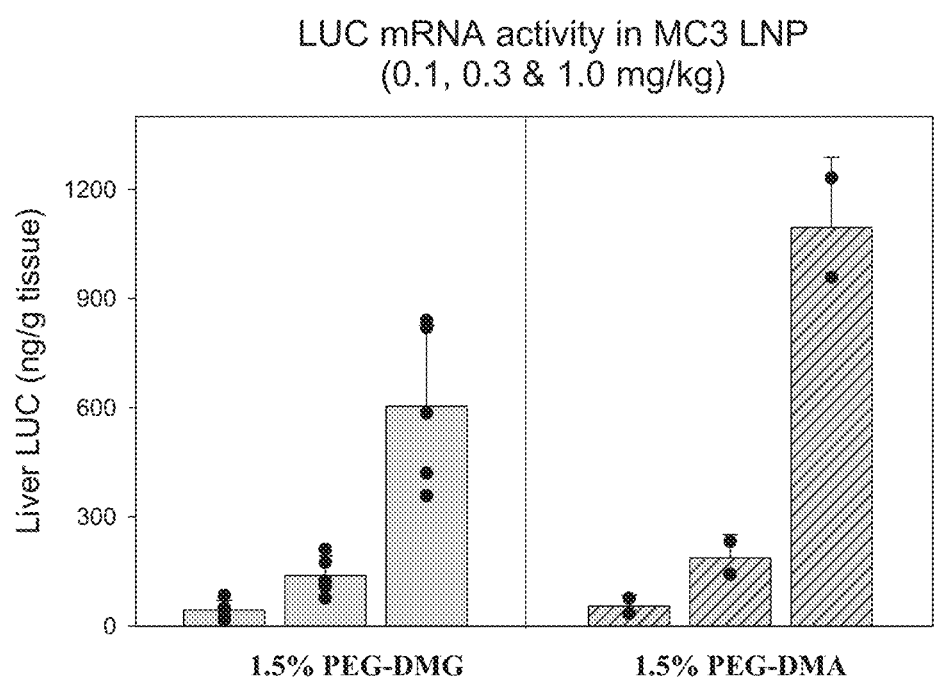
FIG. 4 is a bar graph showing comparative data for compositions comprising two different pegylated lipids.

The comparative activity of PEG-DMG and PEG-DMA lipids is shown in FIG. 4. LNPs were formulated using the following molar ratio: 50% MC3 lipid/10% distearoylphosphatidylcholine (DSPC)/38.5% Cholesterol/1.5% PEG-lipid (PEG-DMG or PEG-DMA). Relative activity was determined by measuring luciferase expression in the liver 4 hours following administration via tail vein injection as described in EXAMPLE 48. The activity was compared at a dose of 0.1, 0.3 and 1.0 mg mRNA/kg and expressed as ng luciferase/g liver measured 4 hours after administration, as described in EXAMPLE 48.

Data is presented in bar graph form in FIG. 4.

EXAMPLE 53

LNP Activity Using a Red Fluorescent Protein Called Cherry Red (CR) mRNA

LNPs using compound 6 are formulated as described in EXAMPLE 47 with mRNA coding for a red fluorescent protein called cherry red (CR, e.g. TriLink Biotechnologies product L-6113). In vivo studies are conducted as described in EXAMPLE 47 and sections of liver tissue are processed and observed by confocal fluorescence microscopy at 4, 6 and 24 hours post administration. Expression levels peaked at around 6 hours and maintained to at least 24 hours. The observed tissue sections demonstrate homogenous expression throughout the liver.

EXAMPLE 54

LNP Delivery of Human FIX mRNA to Hepatocytes in Vivo Results in Therapeutic Levels of hFIX Protein in Mouse Plasma The LNPs with cationic lipids shown in Table 7 are formulated with mRNA coding for human FIX (e.g. TriLink Biotechnologies product L-6110) using the following molar ratio of lipids: 50% lipid/10% distearoylphosphatidylcholine (DSPC)/38.5% Cholesterol/1.5% PEG-lipid as described in EXAMPLE 47. Plasma protein is analyzed by ELISA using a commercially available kit (e.g. Abcam ab108831) as per the suppliers instructions. The measured levels of hFIX expression given in Table 7 for LNPs of compound 5 and compound 6 are clinically relevant and administering these hFIX mRNA LNPs at a dose of 1 mg/kg results in hFIX protein concentrations that would be sufficient to move patients with severe disease into mild disease status. The duration of the hFIX at these levels is ~15 hours or longer.

TABLE 7

Comparative Data

| Compound | Human Factor IX @ 0.3 mg/kg (ng mL in plasma) | Human Factor IX @ 1.0 mg/kg (ng mL in plasma) | Structure |
|---|---|---|---|
| MC3 | 336 ± 21 | 1154 ± 25 | (structure) |

TABLE 7-continued

Comparative Data

| Compound | Human Factor IX @ 0.3 mg/kg (ng mL in plasma) | Human Factor IX @ 1.0 mg/kg (ng mL in plasma) | Structure |
|---|---|---|---|
| 5 | 1097 ± 357 | 4556 ± 686 | 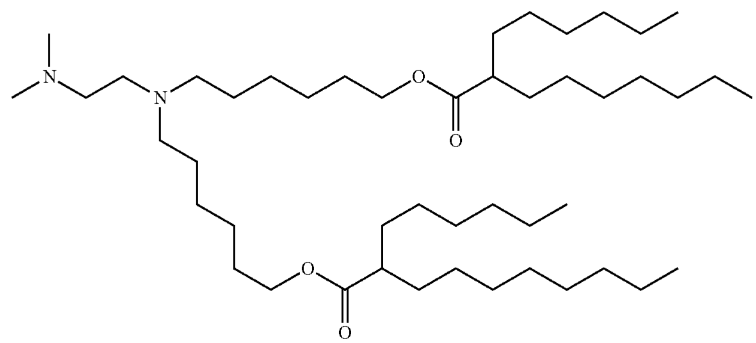 [SMILES: CCCCCCCCC(CCCCCC)C(=O)OCCCCCCN(CCCCCCOC(=O)C(CCCCCC)CCCCCCC)CCN(C)C] |
| 6 | 713 ± 148 | 2697 ± 345 | 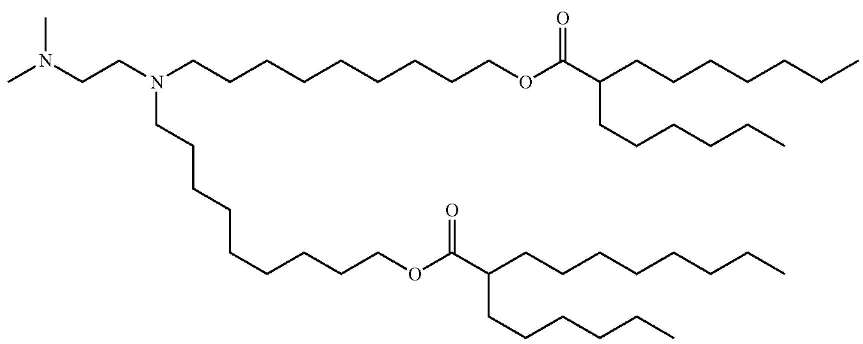 [SMILES: CCCCCCCCC(CCCCCC)C(=O)OCCCCCCCCCN(CCCCCCCCCOC(=O)C(CCCCCC)CCCCCCC)CCN(C)C] |

The various embodiments described above can be combined to provide further embodiments. All of the U.S. Patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having a structure of Formula I:

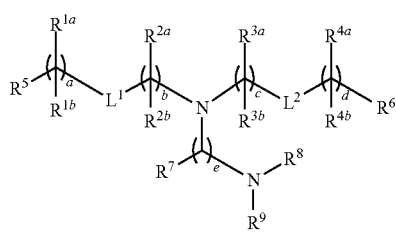

(I)

or a pharmaceutically acceptable salt, tautomer, or stereoisomer thereof, wherein:

$L^1$ and $L^2$ are each independently —O(C=O)— or —(C=O)O—;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, H;

$R^{3a}$ and $R^{3b}$ are, at each occurrence, H;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 4 to 12; and e is 1 or 2, provided that:
$R^{1a}$ and $R^{1b}$ are not isopropyl when a is 6 or n-butyl when a is 8.

2. The compound of claim 1, wherein one of $L^1$ or $L^2$ is —O(C=O)—.

3. The compound of claim 1, wherein one of $L^1$ or $L^2$ is —(C=O)O—.

4. The compound of claim 1, wherein the compound has one of the following structures (Ib) or (Ic):

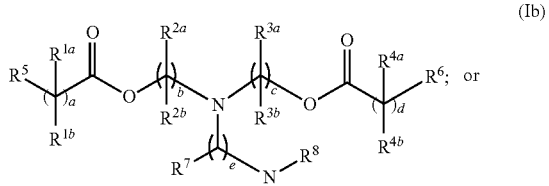

(Ib)

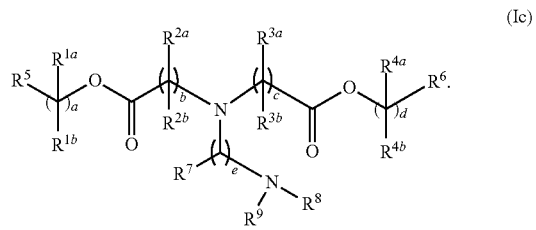

(Ic)

5. The compound of claim 1, wherein a and d are each independently an integer from 2 to 12.

6. The compound of claim 1, wherein a, b, c and d are each independently an integer from 5 to 9.

7. The compound of claim 1, wherein at least one of $R^{1a}$ and $R^{4a}$ is H.

8. The compound of claim 1, wherein $R^{1a}$ and $R^{4a}$ are H at each occurrence.

9. The compound of claim 1, wherein at least one of $R^{1a}$ and $R^{4a}$ is $C_1$-$C_8$ alkyl.

10. The compound of claim 9, wherein $C_1$-$C_8$ alkyl is methyl, ethyl, n-propyl, iso-propyl, n-butyl, iso-butyl, tert-butyl, n-hexyl or n-octyl.

11. The compound of claim 1, wherein at least one of $R^{1b}$ and $R^{4b}$ is H.

12. The compound of claim 1, wherein $R^{1b}$ and $R^{4b}$ are H at each occurrence.

13. The compound of claim 1, wherein $R^{1b}$ together with the carbon atom to which it is bound is taken together with an adjacent $R^{1b}$ and the carbon atom to which it is bound to form a carbon-carbon double bond.

14. The compound of claim 1, wherein $R^{4b}$ together with the carbon atom to which it is bound is taken together with an adjacent $R^{4b}$ and the carbon atom to which it is bound to form a carbon-carbon double bond.

15. The compound of claim 1, wherein one of $R^5$ or $R^6$ is methyl.

16. The compound of claim 1, wherein each of $R^5$ and $R^6$ is methyl.

17. The compound of claim 1, wherein one of $R^5$ or $R^6$ is cycloalkyl.

18. The compound of claim 1, wherein each of $R^5$ and $R^6$ is cycloalkyl.

19. The compound of claim 18, wherein the cycloalkyl is unsubstituted.

20. The compound of claim 17, wherein the cycloalkyl is substituted.

21. The compound of claim 17, wherein the cycloalkyl is substituted with $C_1$-$C_6$alkyl.

22. The compound of claim 21, wherein $C_1$-$C_6$alkyl is tert-butyl.

23. The compound of claim 17, wherein cycloalkyl is cyclohexyl.

24. The compound of claim 1, wherein at least one $R^7$ is H.

25. The compound of claim 24, wherein each $R^7$ is H.

26. The compound of claims 1, wherein at least one $R^7$ is $C_1$-$C_6$ alkyl.

27. The compound of claim 1, wherein e is 2.

28. The compound of claim 1, wherein at least one of $R^8$ or $R^9$ is methyl.

29. The compound of claim 1, wherein each of $R^8$ and $R^9$ is methyl.

30. A compound having one of the following structures:

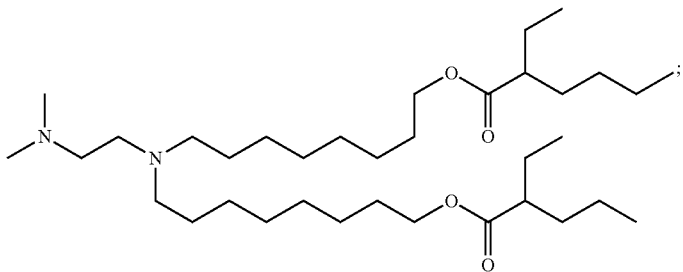

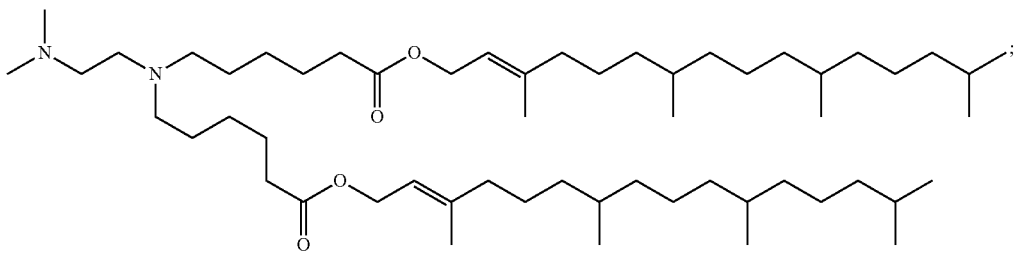

-continued
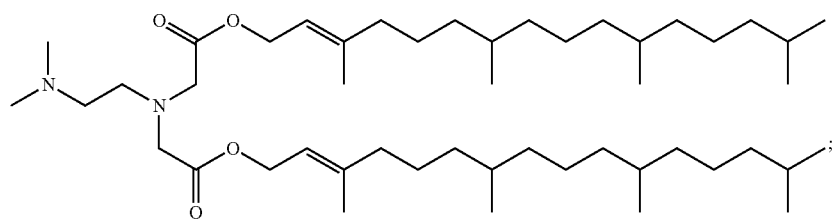
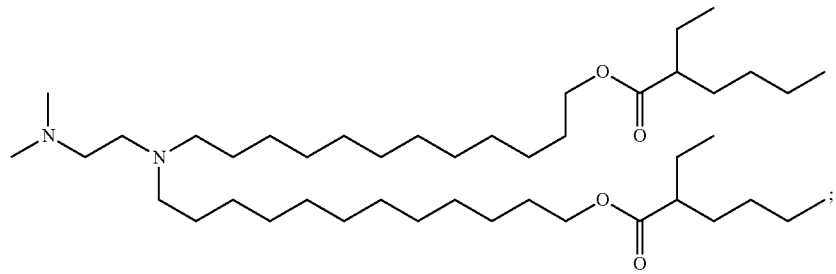
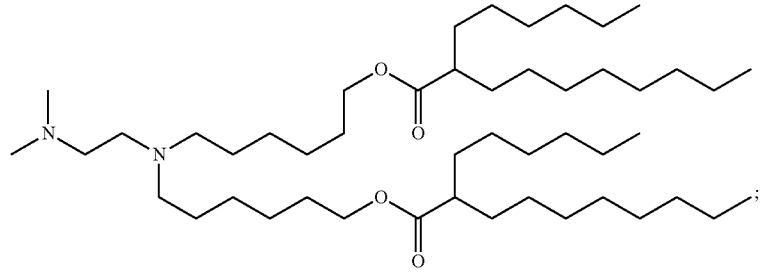
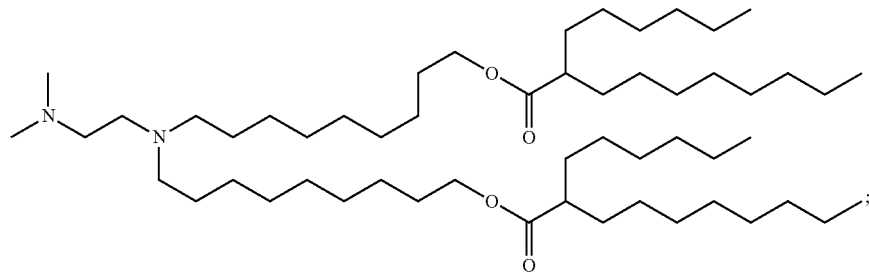
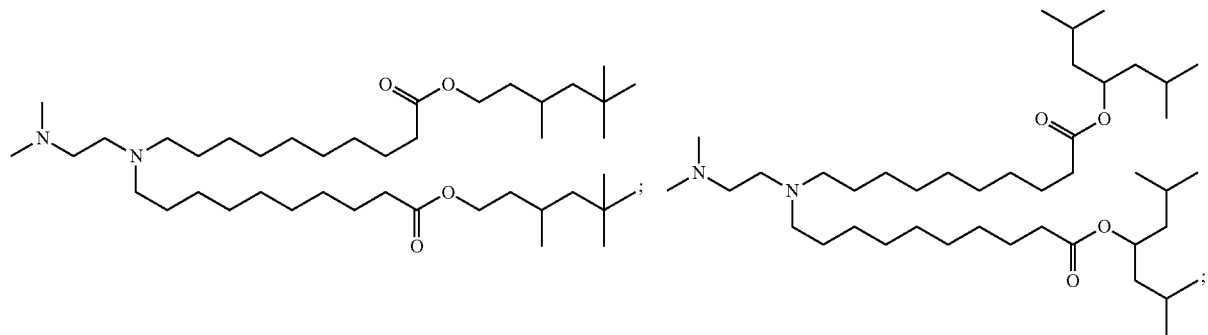
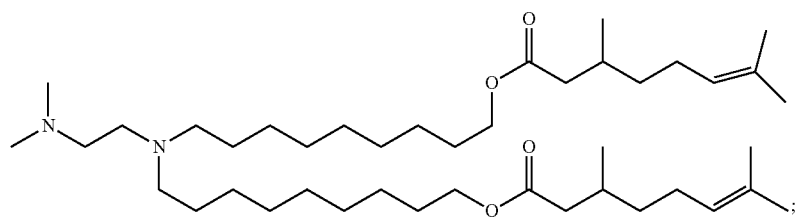

93 94
-continued
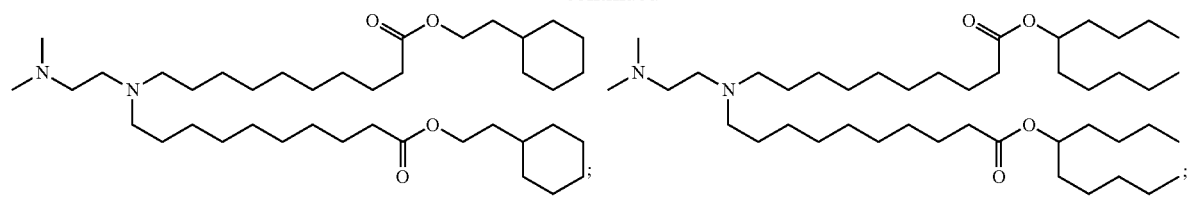
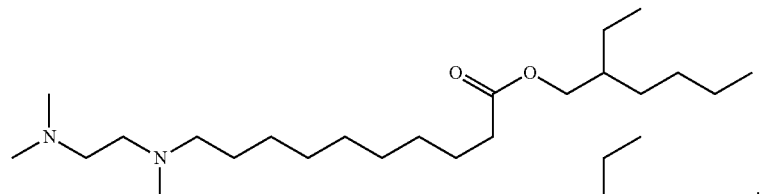
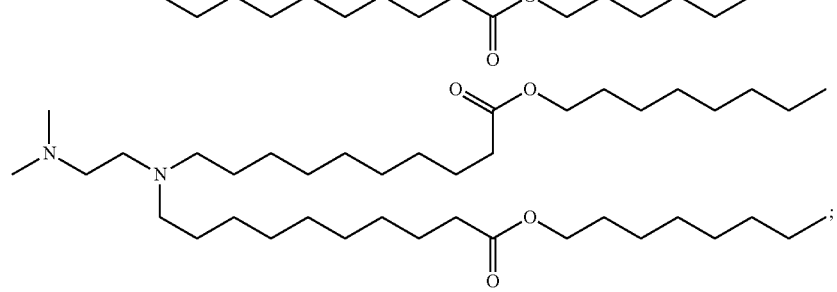
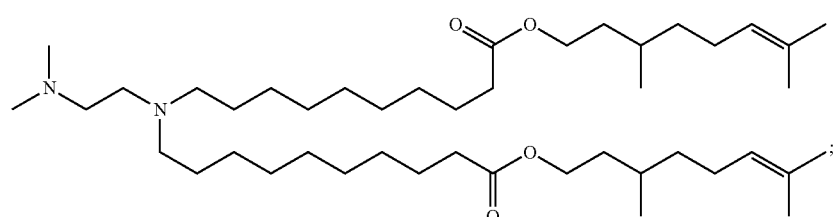
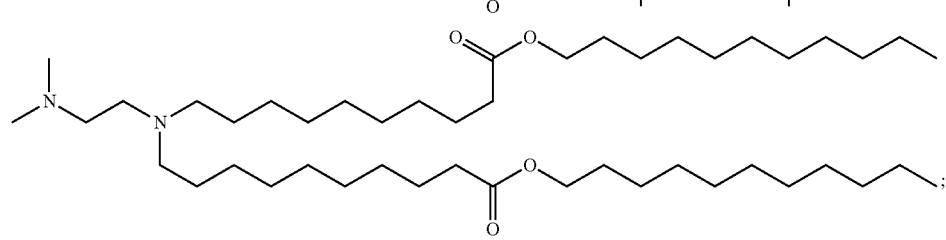
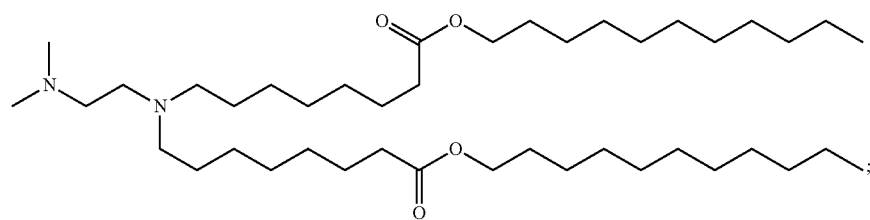
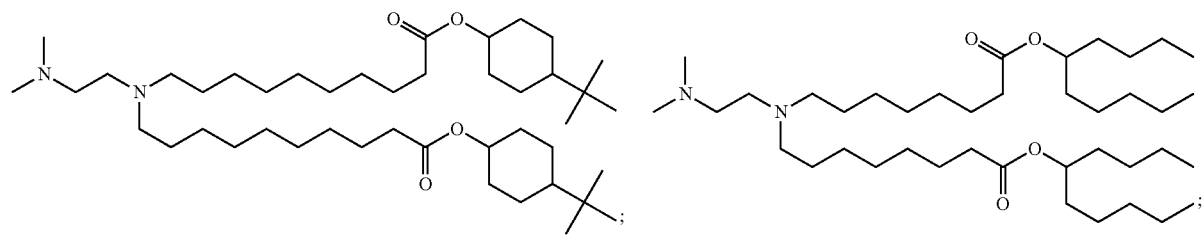

-continued
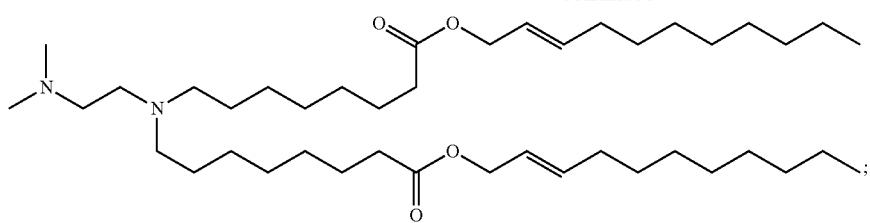
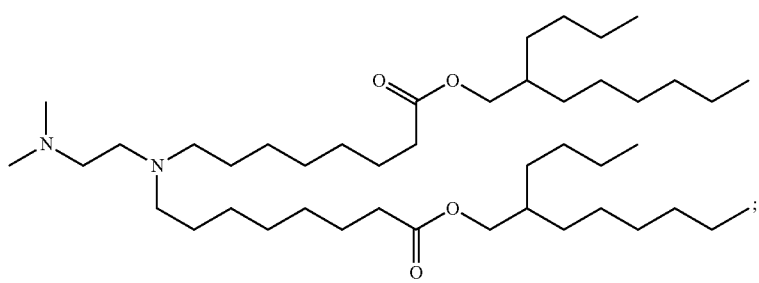
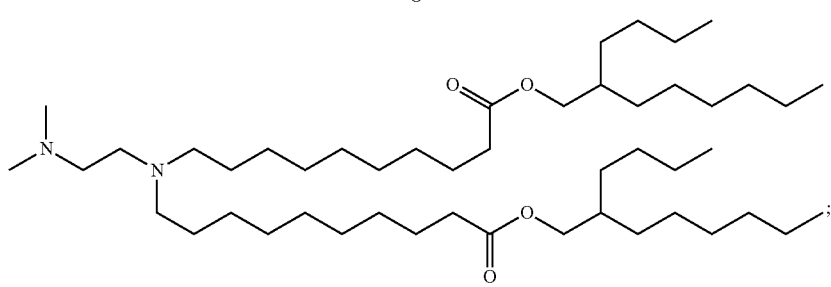
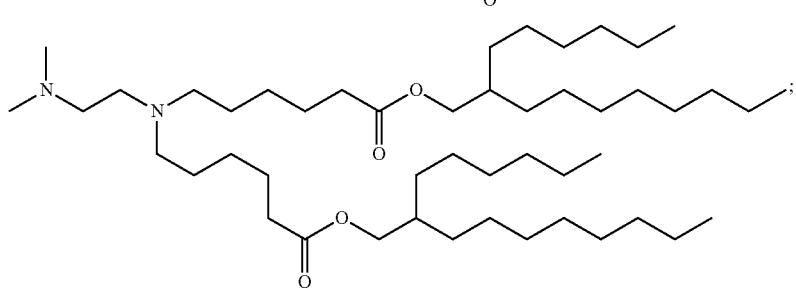
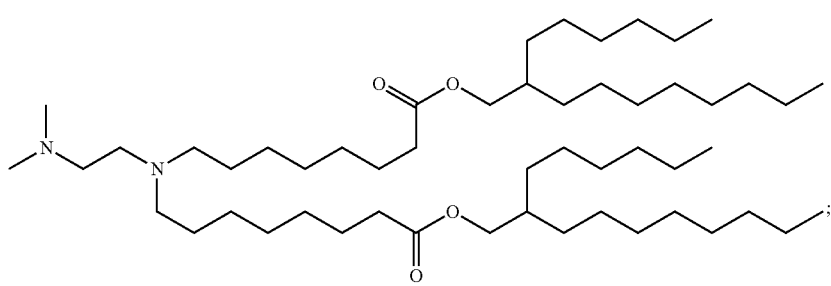
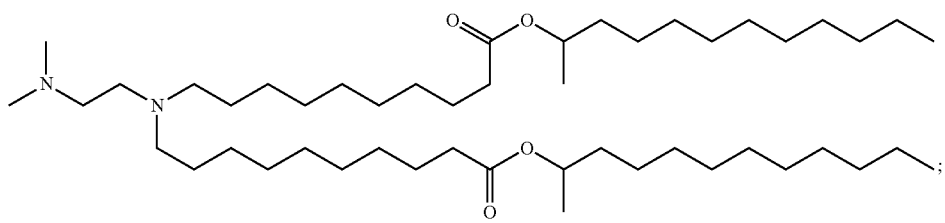

-continued
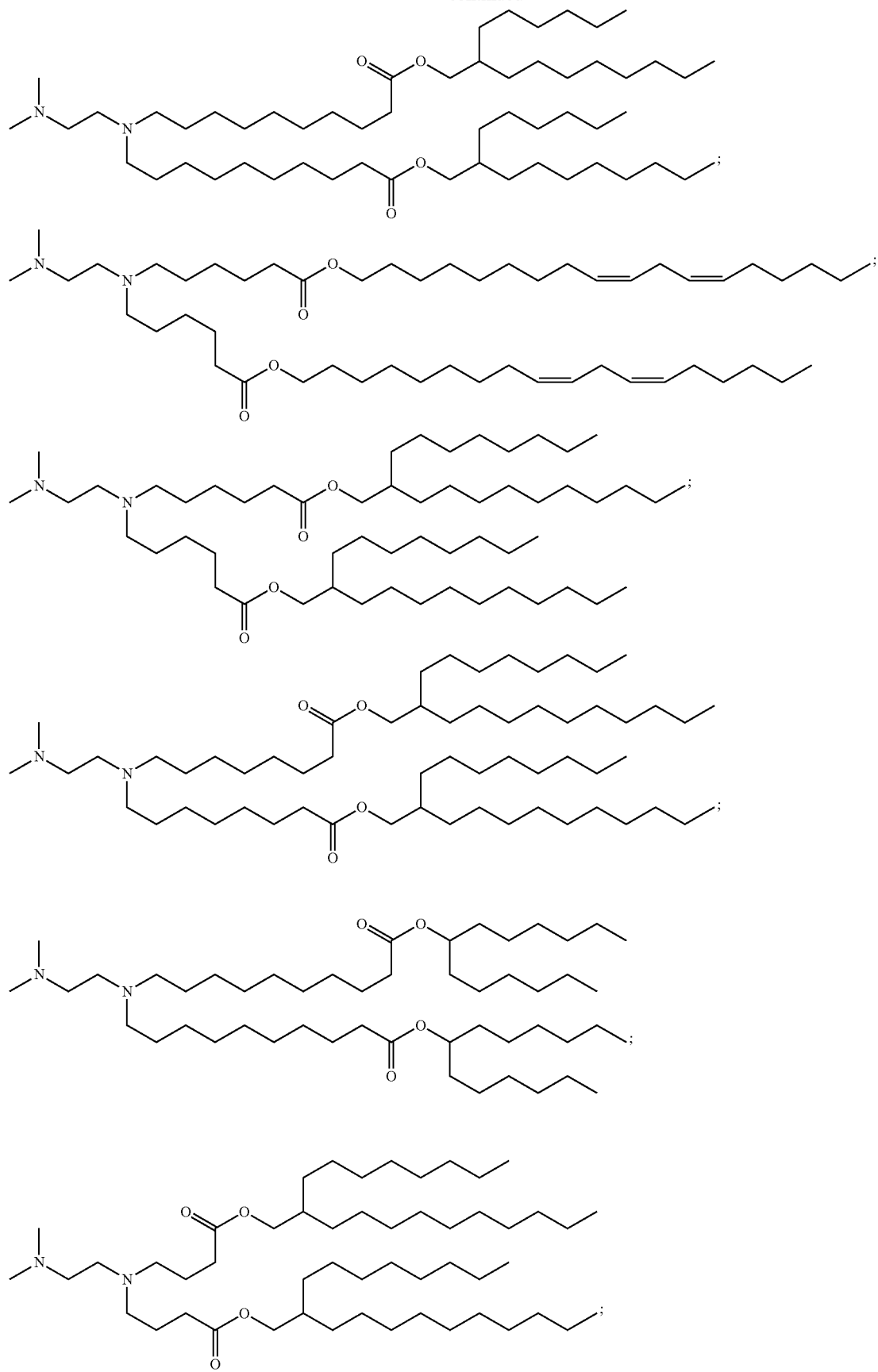

-continued
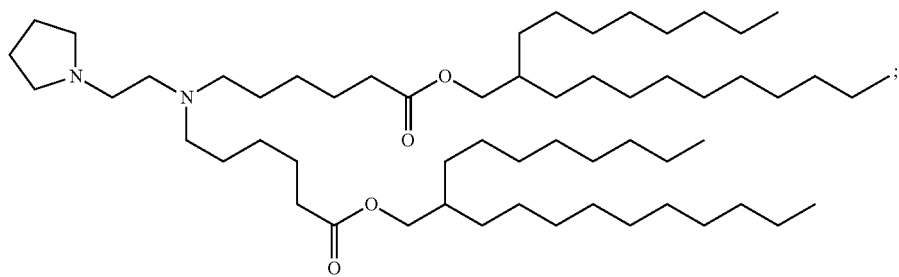
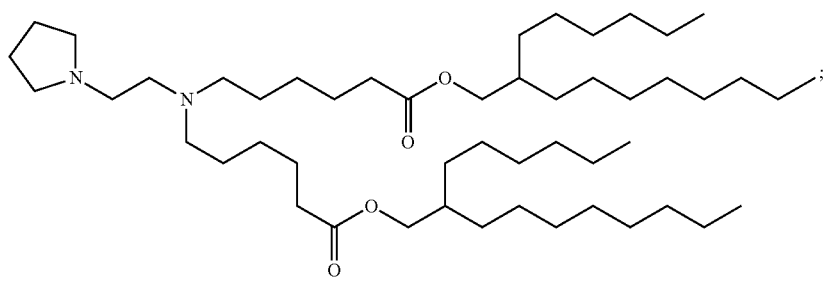
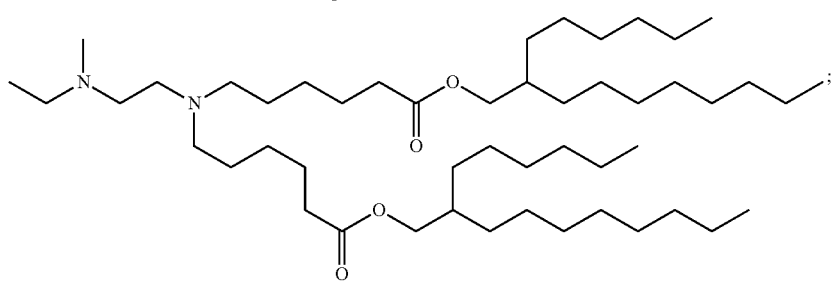
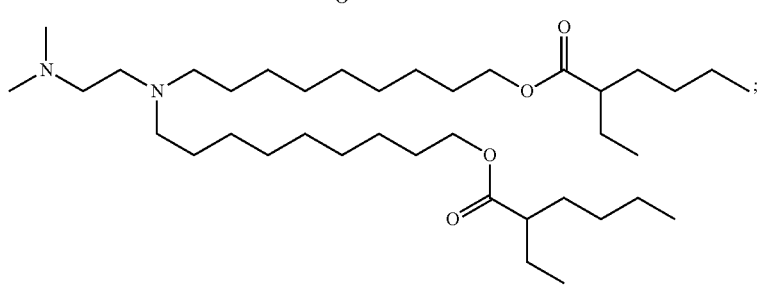
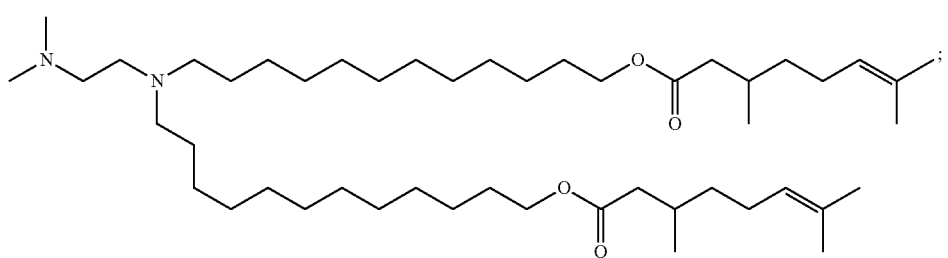
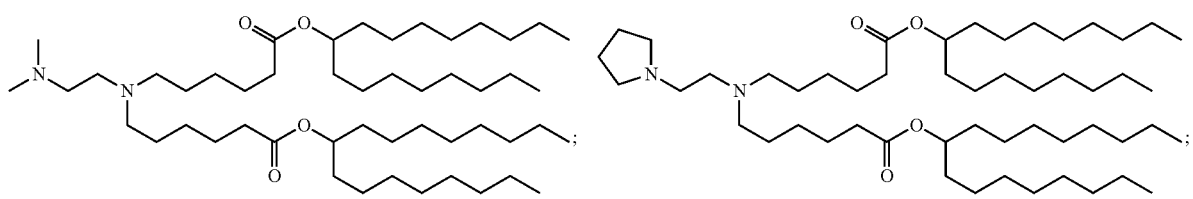

-continued

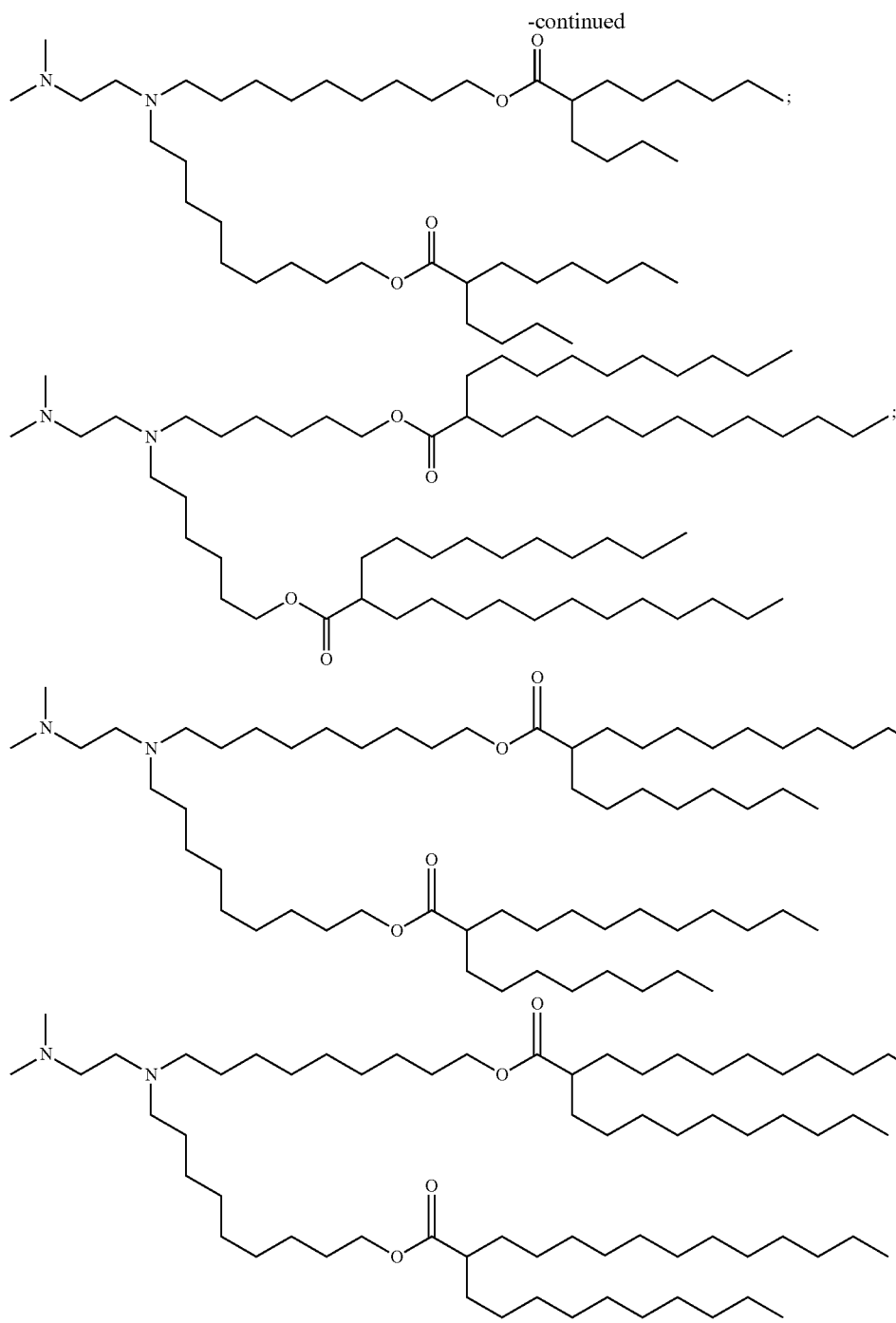

31. A composition comprising the compound of claim 1 and a nucleic acid.

32. A method for administering a nucleic acid to a patient in need thereof, the method comprising preparing or providing the composition of claim 31, and administering the composition to the patient.

33. The composition of claim 31, further comprising one or more excipient selected from the group consisting of neutral lipids, steroids and polymer conjugated lipids.

34. The composition of claim 33, wherein the composition comprises one or more neutral lipids selected from the group consisting of DSPC, DPPC, DMPC, DOPC, POPC, DOPE and SM.

35. The composition of claim 34, wherein the neutral lipid is DSPC.

36. The composition of claim 33, having a molar ratio of the compound to the neutral lipid of from about 2:1 to about 8:1.

37. The composition of claim 33, wherein the steroid is cholesterol.

38. The composition of claim 37, having a molar ratio of the compound to cholesterol of from about 2:1 to 1:1.

39. The composition of claim 33, wherein the polymer conjugated lipid is a pegylated lipid.

40. The composition of claim 39, having a molar ratio of the compound to the pegylated lipid of from about 100:1 to about 25:1.

41. The composition of claim 39, wherein the pegylated lipid is PEG-DMG.

42. The composition of claim 39, wherein the pegylated lipid has the following structure (II):

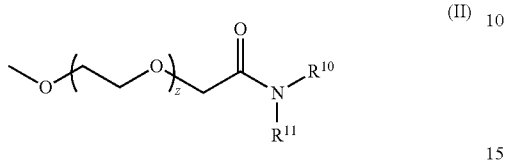

(II)

or a pharmaceutically acceptable salt, tautomer or stereoisomer thereof, wherein:

$R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has a mean value ranging from 30 to 60.

43. The composition of claim 42, wherein $R^{10}$ and $R^{11}$ are each independently straight, saturated alkyl chains containing from 12 to 16 carbon atoms.

44. The composition of claim 42, wherein the average z is about 45.

45. The composition of claim 42, wherein the pegylated lipid has one of the following structures:

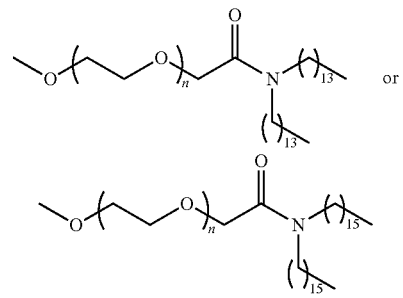

wherein n has a mean value ranging from 40 to 50.

46. The composition of claim 31, wherein the nucleic acid comprises an antisense nucleic acid.

47. The composition of claim 31, wherein the nucleic acid comprises messenger RNA.

* * * * *

UNITED STATES PATENT AND TRADEMARK OFFICE
CERTIFICATE OF CORRECTION

PATENT NO. : 9,738,593 B2
APPLICATION NO. : 14/732218
DATED : August 22, 2017
INVENTOR(S) : Steven M. Ansell et al.

It is certified that error appears in the above-identified patent and that said Letters Patent is hereby corrected as shown below:

In the Specification

Columns 61-62, the reagent above the reaction arrow, used in the conversion of formula 42-5 to formula 42-6:

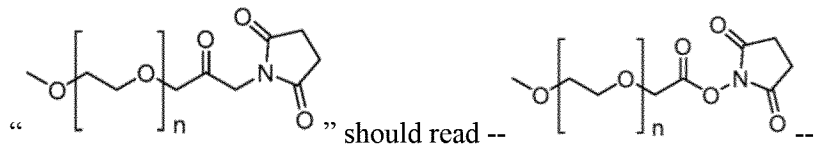 should read --

Columns 87-88, Table 7, Compound 5:

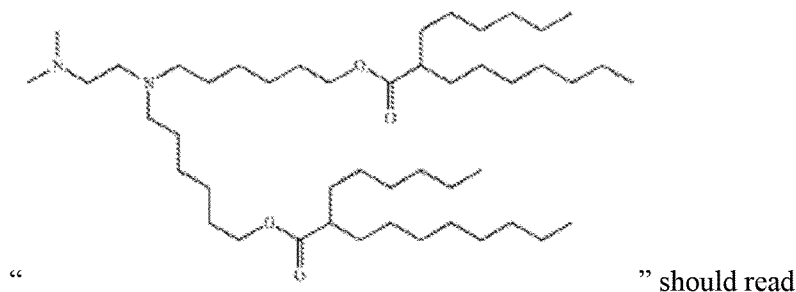 " should read

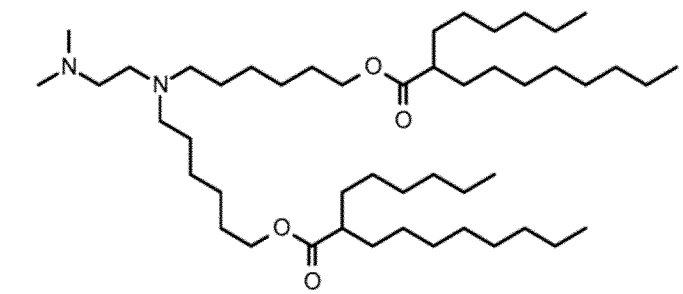

--

Signed and Sealed this
Seventeenth Day of September, 2019

Andrei Iancu
*Director of the United States Patent and Trademark Office*

Columns 87-88, Table 7, Compound 6:
" 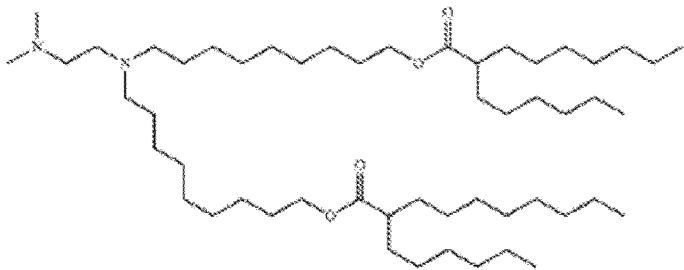 " should read
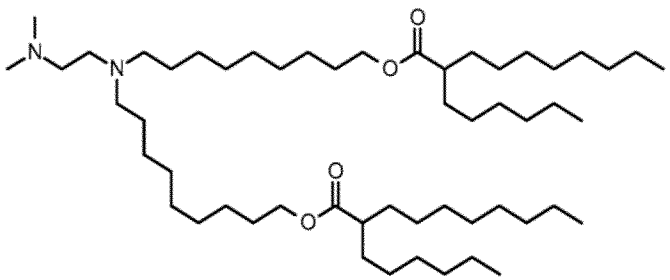
--                    --
In the Claims
Columns 89-90, Claim 30, starting at Line 43:
" 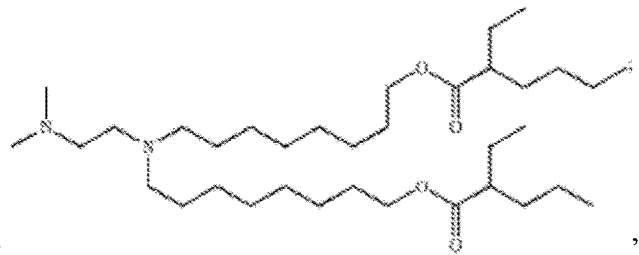 " should read
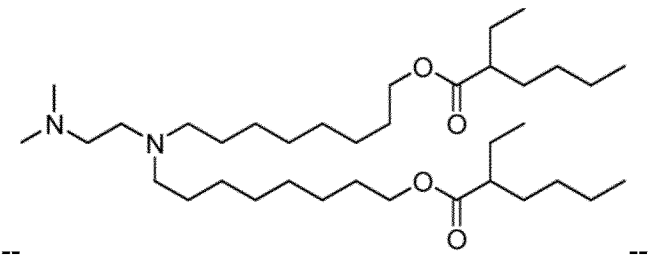
--                    --
Column 90, Claim 26, Line 35:
"The compound of claims, 1 wherein" should read --The compound of claim 1, wherein--